US012685776B2

(12) United States Patent
Qi et al.

(10) Patent No.: US 12,685,776 B2
(45) Date of Patent: Jul. 21, 2026

(54) ARGININE METHYLTRANSFERASE 5 (PRMT5) DEGRADERS AND USES THEREOF

(71) Applicant: DANA-FARBER CANCER INSTITUTE, INC., Boston, MA (US)

(72) Inventors: Jun Qi, Sharon, MA (US); Lei Wu, Allston, MA (US); Paul M. Park, Waltham, MA (US); Logan H. Sigua, North Sutton, NH (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 922 days.

(21) Appl. No.: 17/917,075

(22) PCT Filed: Apr. 5, 2021

(86) PCT No.: PCT/US2021/025726
§ 371 (c)(1),
(2) Date: Oct. 5, 2022

(87) PCT Pub. No.: WO2021/207052
PCT Pub. Date: Oct. 14, 2021

(65) Prior Publication Data

US 2023/0149551 A1 May 18, 2023

Related U.S. Application Data

(60) Provisional application No. 63/005,583, filed on Apr. 6, 2020.

(51) Int. Cl.
*A61K 47/55* (2017.01)
*A61P 11/00* (2006.01)
*A61P 35/00* (2006.01)
*A61P 35/02* (2006.01)

(52) U.S. Cl.
CPC .............. *A61K 47/55* (2017.08); *A61P 11/00* (2018.01); *A61P 35/00* (2018.01); *A61P 35/02* (2018.01)

(58) Field of Classification Search
CPC ...................................................... A61K 47/55
See application file for complete search history.

(56) References Cited

U.S. PATENT DOCUMENTS

2017/0121321 A1 5/2017 Crews et al.

FOREIGN PATENT DOCUMENTS

| | | | |
|---|---|---|---|
| WO | 2014182744 | A1 | 11/2014 |
| WO | 2019/152536 | A1 | 8/2019 |
| WO | 2019/165189 | A1 | 8/2019 |

OTHER PUBLICATIONS

Silverman, R. B., & Holladay, M. W. (2014). The Organic Chemistry of drug design and Drug Action. Academic Press. (Year: 2014).*
Topliss JG. Utilization of operational schemes for analog synthesis in drug design. J Med Chem. Oct. 1972;15(10):1006-11. doi: 10.1021/jm00280a002. PMID: 5069767. (Year: 1972).*
Vinet M, et al. Protein arginine methyltransferase 5: A novel therapeutic target for triple-negative breast cancers. Cancer Med. May 2019;8(5):2414-2428. doi: 10.1002/cam4.2114. Epub Apr. 8, 2019. PMID: 30957988; PMCID: PMC6537044 (Year: 2019).*
Janse, et al., "Localization to the proteasome is sufficient for degradation," J. Biol. Chem., 2004, vol. 279, No. 20, pp. 21415-21420.
Song, et al., "Targeting proteasome ubiquitin receptor Rpn13 in multiple myeloma," Leukemia, 2016, vol. 30, pp. 1877-1886.
Lai, et al., "Modular PROTAC Design for the Degradation of Oncogenic BCR-ABL", Angew. Chem. Int. Ed., 2016, vol. 55, pp. 807-810.
Bekes, M. et al., "PROTAC targeted protein degraders: the past is prologue", Nature Reviews, 2022, vol. 21, pp. 181-200.
Li, X. et al., "Proteolysis-targeting chimera (PROTAC) for targeted protein degradation and cancer therapy", J. Hematol. Oncol., 2020, vol. 13, No. 50, 14 pages.
Tan, L. et al., "When Kinases Meet PROTACS", Chin. J. Chem., 2018, vol. 36, pp. 971-977.

* cited by examiner

*Primary Examiner* — Andrew D Kosar
*Assistant Examiner* — Connor K English
(74) *Attorney, Agent, or Firm* — ArentFox Schiff LLP; Daniel W. Clarke; Shawn P. Foley

(57) ABSTRACT

Disclosed are to bifunctional compounds that target PRMT5 for degradation, compositions, and methods for treating diseases or conditions mediated by aberrant arginine methyltransferase 5 (PRMT5) activity.

24 Claims, 8 Drawing Sheets

ARGININE METHYLTRANSFERASE 5 (PRMT5) DEGRADERS AND USES THEREOF

RELATED APPLICATIONS

This application is a national stage application, filed under 35 U.S.C. § 371, of International Application No. PCT/US2021/025726, filed Apr. 5, 2021, which claims the benefit of priority under 35 U.S.C. § 119 (e) to U.S. Provisional Application No. 63/005,583, filed on Apr. 6, 2020, each of which is incorporated herein by reference in its entirety.

BACKGROUND OF THE INVENTION

Protein arginine methyltransferases (PRMTs) catalyze post-translational methylation of specific arginine residues in a wide variety of cellular proteins such as histones and transcription factors. This modification of cellular proteins enables PRMTs to regulate many diverse cellular processes such as gene transcription, mRNA splicing, DNA repair, signal transduction, protein subcellular localization, and cell cycle progression (Stouth et al., Front. Physiol. 8:870 (2017)).

PRMTs are classified into three main classes or types based on the type of modification they catalyze: Type I (PRMT 1, 2, 3, 4, 6 and 8) catalyzes monomethylation and asymmetric demethylation; type II (PRMT5 and PRMT9) catalyzes monomethylation and symmetric demethylation; and type III (PRMT7) only catalyzes monomethylation (Shailesh et al., Oncotarget 9(94):36705-36718 (2018)).

Increasing evidence has shown that PRMT5 is overexpressed in many malignant tumors, including B and T cell lymphoma, metastatic melanoma, neuroblastoma; glioblastoma, germ cell tumors, ovarian cancer, nasopharyngeal cancer, breast cancer, colorectal cancer, and gastric cancer (Xiao et al., Biomed. Pharmacother. 114:108790 (2019); Shailesh et al., Oncotarget 9(94):36705-36718)). As an oncogene, PRMT5 is believed to play an indispensable regulatory role in the pathological progression of several human cancers by promoting the proliferation, invasion, and migration of cancer cells (Xiao et al., supra.). These findings have suggested that PRMT5 may serve as a potential biomarker or therapeutic target of cancer (Xiao and Shailesh, supra.).

SUMMARY OF THE INVENTION

A first aspect of the present invention is directed to a bifunctional compound having a structure represented by formula (I):

(I)

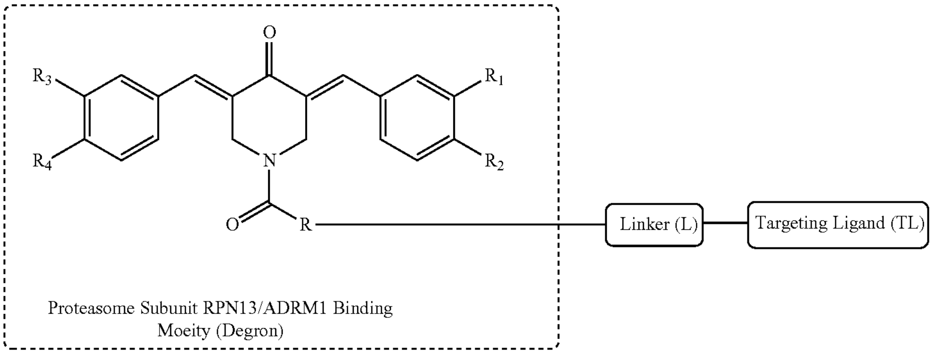

, wherein

R represents

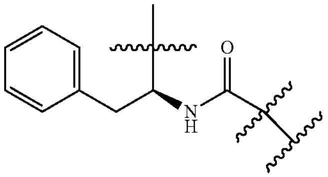

or

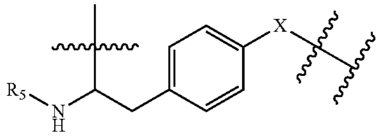

, wherein the squiggle ( ) represents the attachment point to the carbonyl group (C(O)) and the double-squiggle ( ) represents the attachment point to

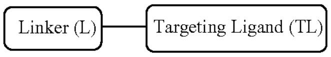

;

X represents $CH_2$, NH or O;

$R_1$ and $R_3$ each independently represents hydrogen, halo, methoxy, $NO_2$, CN, —C(O)OR'$_1$ or —C(O)NR'$_1$R'$_2$; $R_2$ and $R_4$ each independently represents halo, methoxy, $NO_2$, CN, —C(O)OR'$_1$ or —C(O)NR'$_1$R'$_2$, wherein R'$_1$ and R'$_2$ are independently H or optionally substituted $C_1$-$C_6$ alkyl;

$R_5$ represents H, biotinyl, or a solubility enhancing group; and the targeting ligand represents a moiety that binds arginine methyltransferase 5 (PRMT5), or a pharmaceutically acceptable salt or stereoisomer thereof.

Another aspect of the present invention is directed to a pharmaceutical composition containing a therapeutically effective amount of a bifunctional compound of formula (I) or a pharmaceutically acceptable salt or stereoisomer thereof, and a pharmaceutically acceptable carrier.

In another aspect of the present invention, methods of making the bifunctional compounds are provided.

A further aspect of the present invention is directed to a method of treating a disease or disorder characterized or mediated by aberrant PRMT5 activity, that includes administering a therapeutically effective amount of a bifunctional compound of formula (I) or a pharmaceutically acceptable salt or stereoisomer thereof, to a subject in need thereof.

In some embodiments, the disease or disorder is cancer. In some embodiments, the cancer is breast cancer (e.g., triple-negative breast cancer), colorectal cancer, gastric cancer, lung cancer, nasopharyngeal cancer, ovarian cancer, germ cell tumors, B and T cell lymphoma, metastatic melanoma, neuroblastoma or glioblastoma. In some embodiments, the cancer is myelodysplastic syndrome (MDS) or acute myeloid leukemia (AML).

Without intending to be bound by any particular theory of operation, the bifunctional compounds of the present invention are believed to degrade aberrant PRMT5 proteins that are involved in the genesis and/or progression of disease via the cell's ubiquitin/proteasome system, whose function is to routinely identify and remove damaged proteins. The bifunctional compounds of the present invention tag PRMT5 (which is bound by the targeting ligand functionality) and proteosome subunit RPN13/adhesion regulating molecule 1 (ADRM1) for PRMT5 degradation via proteosome proximity. After destruction of a PRMT5 molecule, the degrader is released and continues to be active. Thus, by engaging and exploiting the body's own natural protein disposal system, the bifunctional compounds of the present invention may represent a potential improvement over traditional small molecule inhibitors of aberrant proteins in the treatment of cancers and other disease that have proven difficult to treat.

The bifunctional compounds of the present invention may serve as a set of new chemical tools for PRMT5 knockdown and may provide effective treatments for PRMT5-mediated diseases and disorders such as cancer.

DETAILED DESCRIPTION

Figure 1:
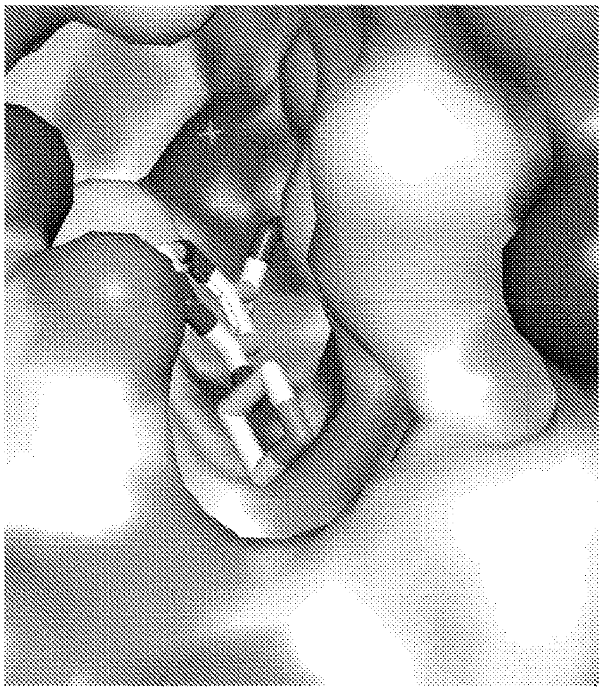
FIG. 1 is an image of the crystal structure of the targeting ligand TL-1 binding PRMT5.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "alkoxylene" refers to a saturated monovalent aliphatic radicals of the general formula ($—O—C_nH_{2n}—$) where n represents an integer (e.g., 1, 2, 3, 4, 5, 6, or 7) and is inclusive of both straight-chain and branched-chain radicals. The alkoxylene chain may be attached to the rest of the molecule through a single bond and to the radical group through a single bond. In some embodiments, the alkoxylene group contains one to 3 carbon atoms (—O—$C_1$-$C_3$ alkoxylene). In other embodiments, an alkoxylene group contains one to 5 carbon atoms (—O—$C_1$-$C_5$ alkoxylene).

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring. The structure of any aryl group that is capable of having double bonds positioned differently is considered so as to embrace any and all such resonance structures.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur and oxygen. In some embodiments, heterocyclyl includes 4- to 6-membered monocycles having one or more heteroatoms selected from nitrogen, sulfur and oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$— heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring. The structure of any heteroaryl group that is capable of having double bonds positioned differently is considered so as to embrace any and all such resonance structures.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Unless stated otherwise, and to the extent not further defined for any particular group(s), any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

To the extent not disclosed otherwise for any particular group(s), representative examples of substituents may thus include alkyl, substituted alkyl (e.g., $C_1$-$C_6$, $C_1$-$C_5$, $C_1$-$C_4$, $C_1$-$C_3$, $C_1$-$C_2$, $C_1$), alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, $C_1$), haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

The term "solubility enhancing group" as used herein refers to a moiety that enhances solubility of a compound in aqueous, physiologically acceptable fluids that has relatively low solubility therein. Examples of solubilizing groups include substituents containing a group susceptible to being ionized in water at a pH range from 0 to 14, ionizable groups capable of forming salts, and highly polar substituents having a high dipolar moment and capable of forming strong interaction with water molecules. In some embodiments, the solubility enhancing group is alpha-chloro acetyl.

The term "binding" as it relates to interaction between the targeting ligand and the targeted protein, which in this invention is arginine methyltransferase 5 (PRMT5), typically refers to an inter-molecular interaction that is preferential (also referred to herein as "selective") in that binding of the targeting ligand with other proteins present in the cell, is substantially less and functionally insignificant.

The term "binding" as it relates to interaction between the proteosome subunit RPN13/adhesion regulating molecule 1 (ADRM1) binding moiety (also referred to herein as degron) and ADRM1, typically refers to an inter-molecular interaction that may or may not exhibit an affinity level that equals or exceeds that affinity between the targeting ligand and the target protein, but nonetheless wherein the affinity is sufficient to achieve recruitment of RPN13/ADRM1 to the targeted degradation and the selective degradation of the targeted protein.

Broadly, the bifunctional compounds have a structure represented by formula (I):

(I)

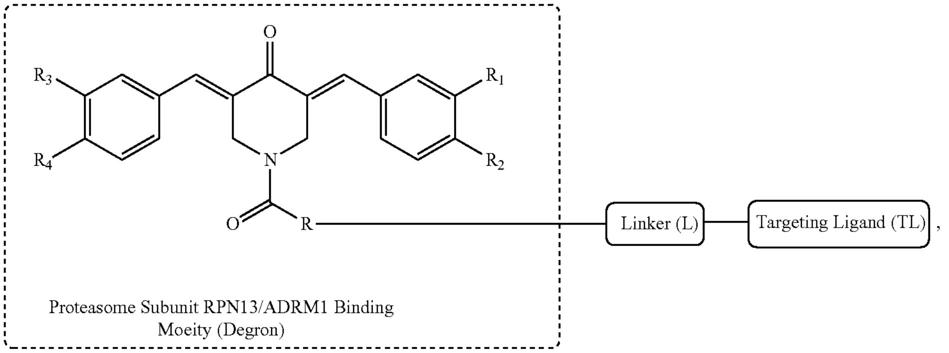

, wherein

R represents

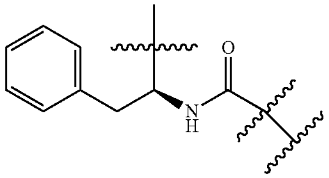

or

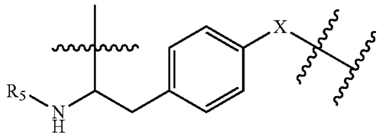

, wherein the squiggle ( ) represents the attachment point to the carbonyl group (C(O)) and the double-squiggle ( ) represents the attachment point to

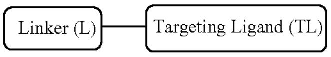

;

X represents $CH_2$, NH or O;

$R_1$ and $R_3$ each independently represents hydrogen, halo, methoxy, $NO_2$, CN, —C(O)OR'$_1$ or —C(O)NR'$_1$R'$_2$, and $R_2$ and $R_4$ each independently represents halo, methoxy, $NO_2$, CN, —C(O)OR'$_1$ or —C(O)NR'$_1$R'$_2$, wherein R'$_1$ and R'$_2$ are independently H or optionally substituted $C_1$-$C_6$ alkyl; $R_5$ represents H, biotinyl, or a solubility enhancing group; and the targeting ligand represents a moiety that binds arginine methyltransferase 5 (PRMT5), or a pharmaceutically acceptable salt or stereoisomer thereof.

In some embodiments, each of $R_1$, $R_2$, $R_3$ and $R_4$ independently represents Cl.

In some embodiments, each of $R_1$ and $R_3$ represents CN, and each of $R_2$ and $R_4$ represents Cl.

In some embodiments, each of $R_1$ and $R_3$ represents Cl, and each of $R_2$ and $R_4$ represents methoxy.

In some embodiments, each of $R_1$ and $R_3$ represents H, and each of $R_2$ and $R_4$ represents $NO_2$.

In some embodiments, $R_5$ is H. In some embodiments, $R_5$ is biotinyl. In some embodiments, $R_5$ is a solubility enhancing group. In some embodiments, the solubility enhancing group is alpha-chloro acetyl. Yet other solubility enhancing groups which may be suitable for use in the present invention are described in U.S. Patent Application Publication Nos. 2010/0081653 and 2011/0065698, and U.S. Pat. Nos. 5,268,486, 5,714,386, and 7,781,229. Representative examples of solubility enhancing groups include substituted alkyl amines, substituted alkyl alcohols, alkyl ethers, aryl amines, pyridines, phenols, carboxylic acids, tetrazoles, sulfonamides, amides, sulfonylamides, sulfonic acids, sulfinic acids, phosphates, sulfonylureas.

PRMT5 Targeting Ligands

The bifunctional compounds (degraders) of the present invention target PRMT5 for degradation.

In some embodiments, the PRMT5 targeting ligand is represented by any one structures TL1 and TL2:

(TL1)

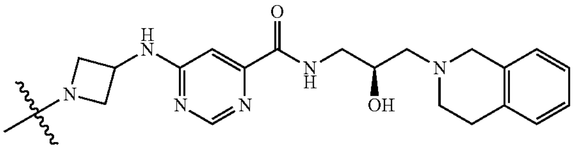

and (TL2)

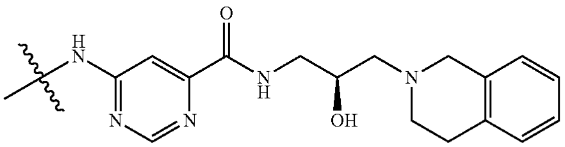

.

An image of a crystal structure of targeting ligand TL1 binding PRMT5 is shown in FIG. 1.

Yet other moieties which may be suitable for use in the present invention as PRMT5-targeting ligands are described in U.S. Patent Application Publication Nos. 2017/0334861 and 2018/0098987, and U.S. Pat. Nos. 8,993,555, 9,365,519, and 9,675,614.

In some embodiments, the bifunctional compounds of the present invention are represented by any one of structures (I-1) to (I-4):

(I-1)
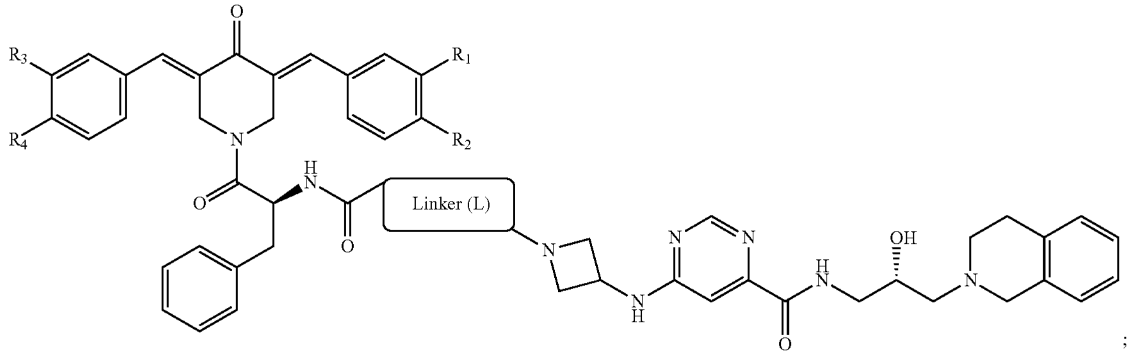
;
(I-2)
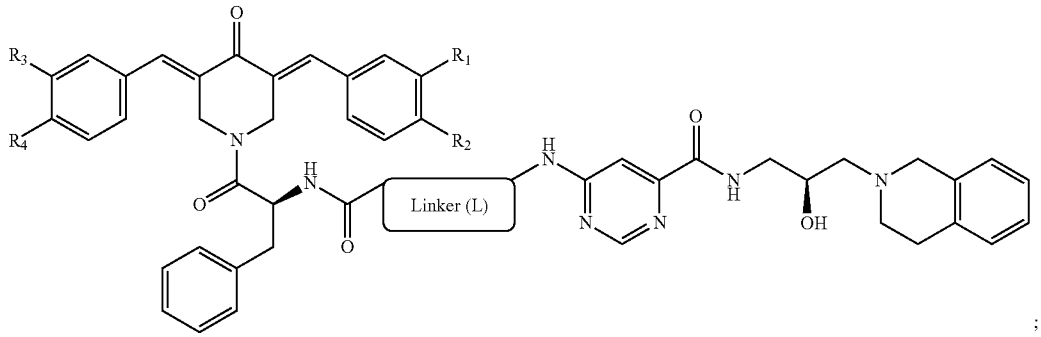
;
(I-3)
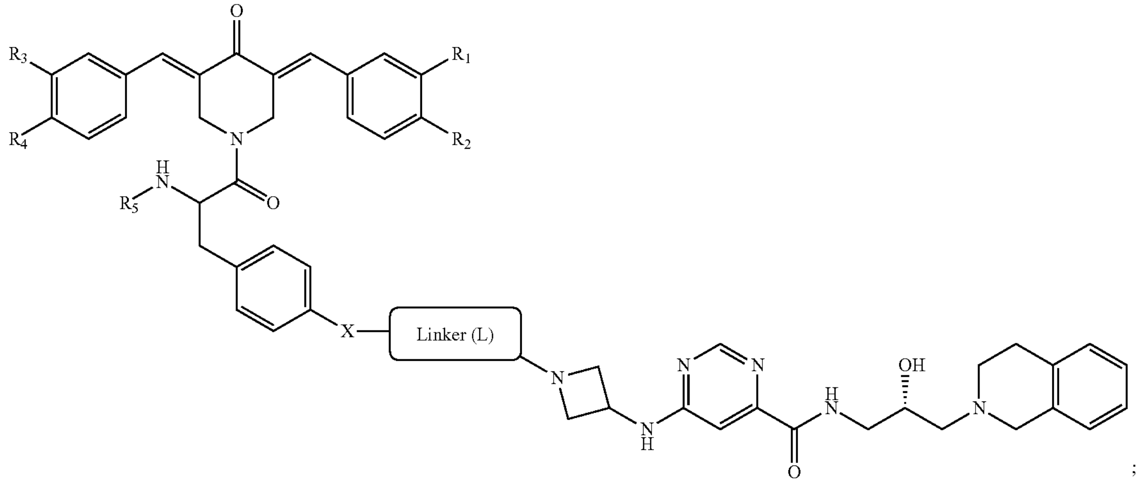
;

-continued
and
(I-4)
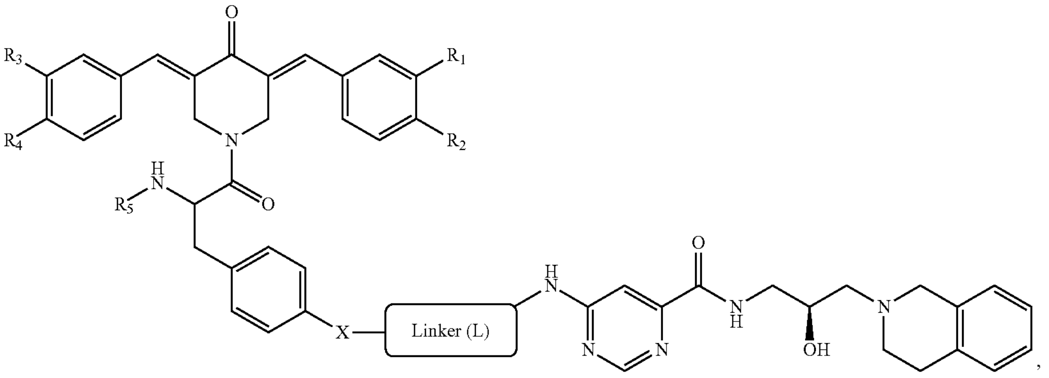
or a pharmaceutically acceptable salt or stereoisomer thereof.
In some embodiments, the bifunctional compounds of the present invention are represented by any one of structures (I-1a) to (I-4c):
(I-1a)
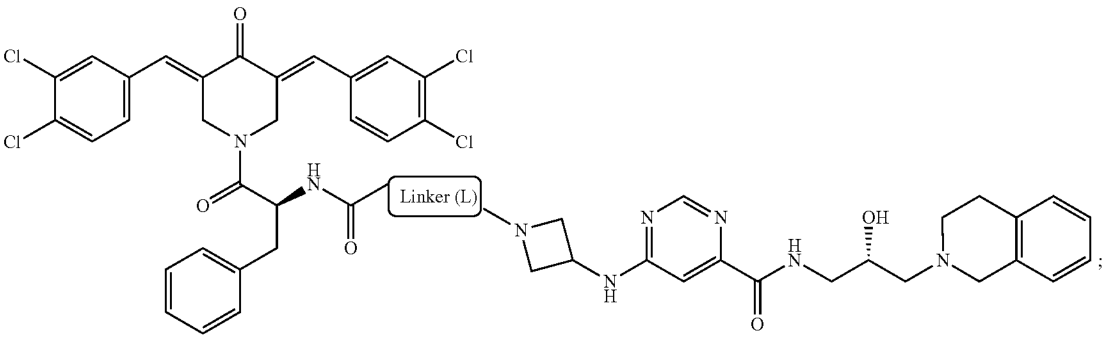
(I-1b)
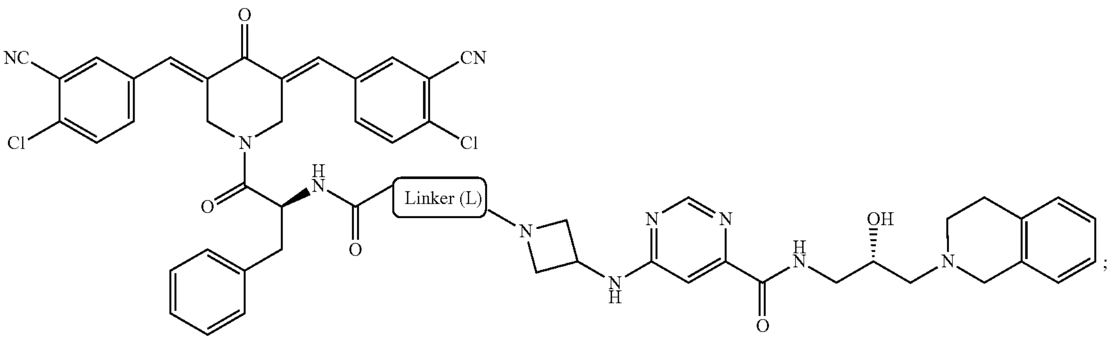

-continued
(I-1c)
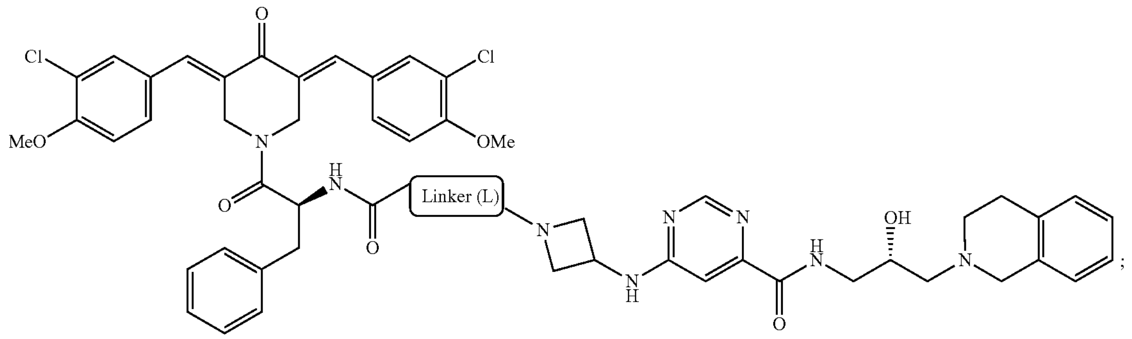
(I-2a)
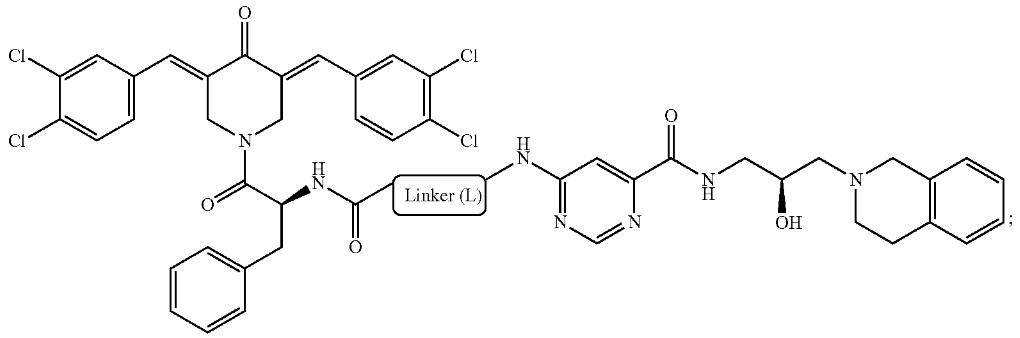
(I-2b)
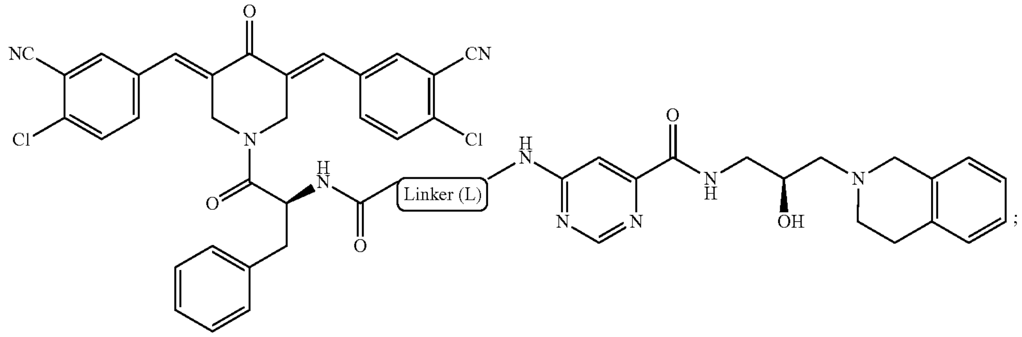
(I-2c)
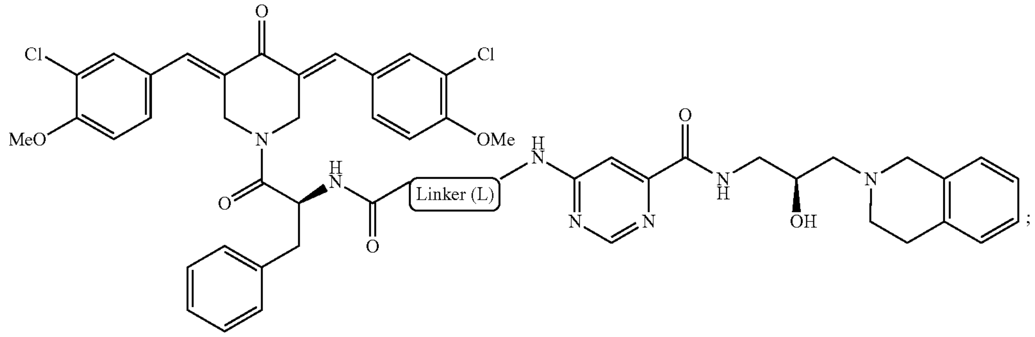

-continued
(I-3a)
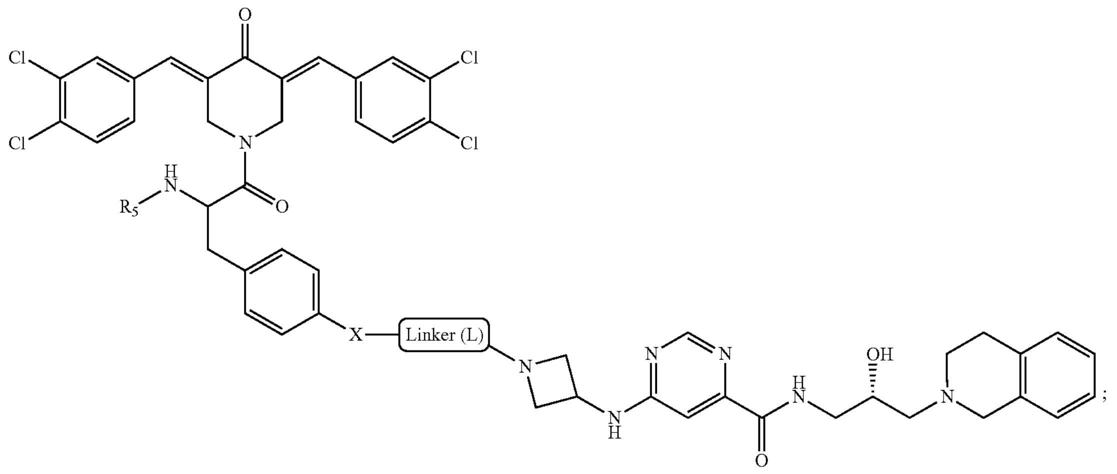
(I-3b)
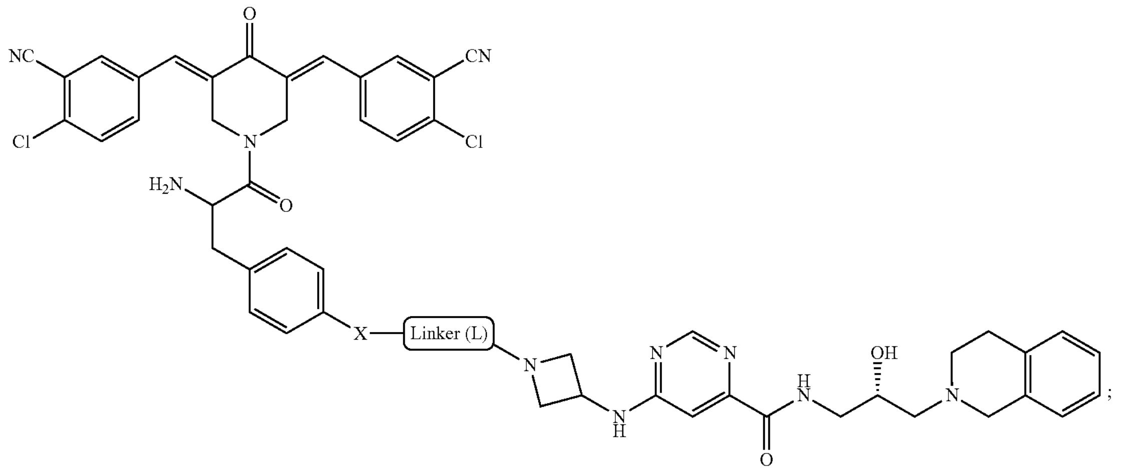
(I-3c)
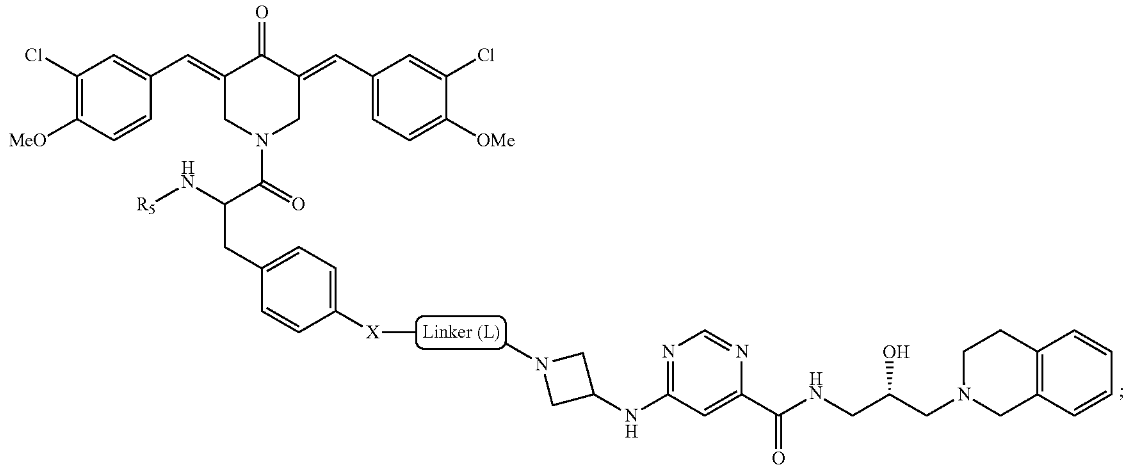

-continued
(I-4a)
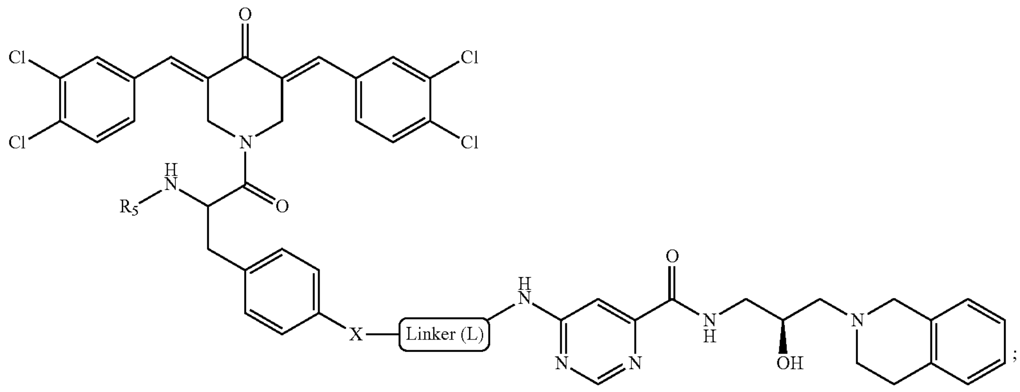
;
(I-4b)
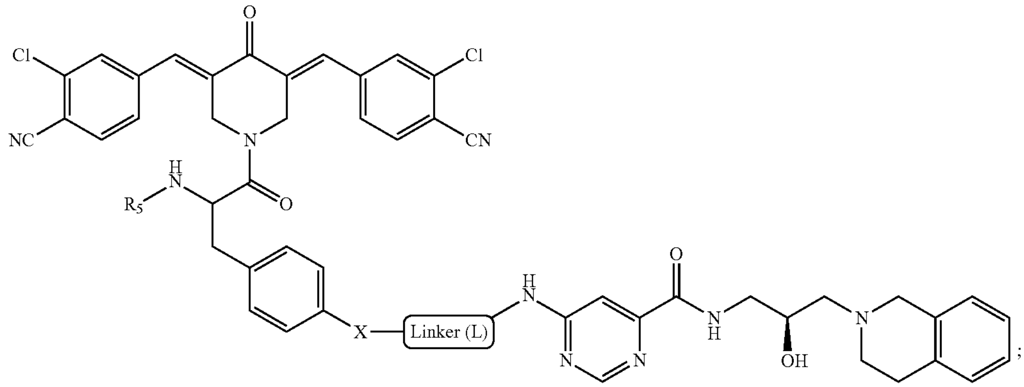
;
(I-4c)
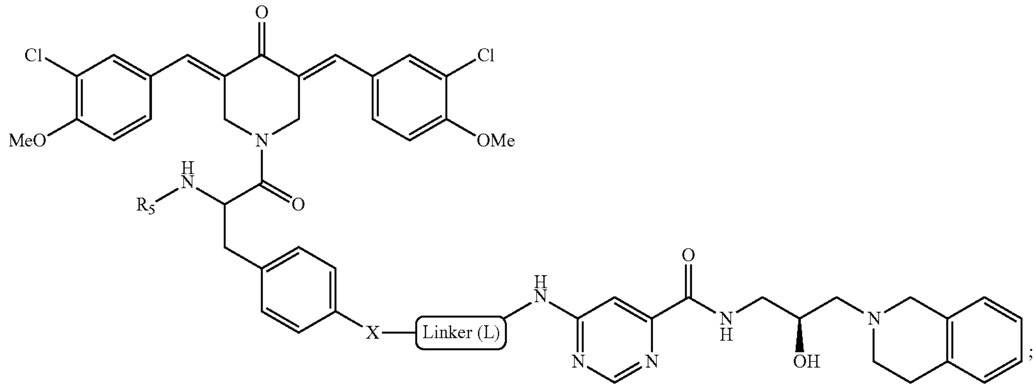
;
(I-5a)
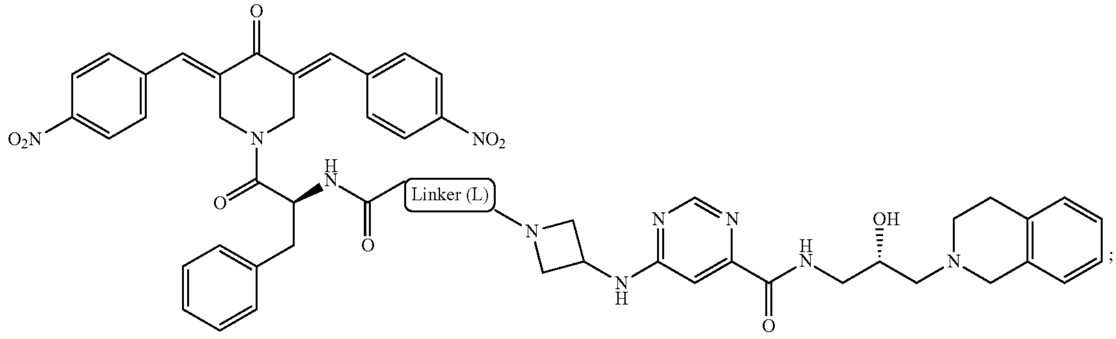
;

-continued (I-5b)

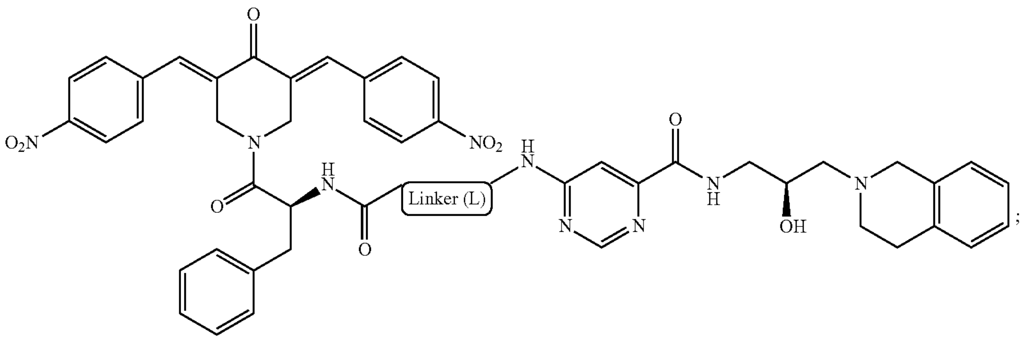

(I-5c)

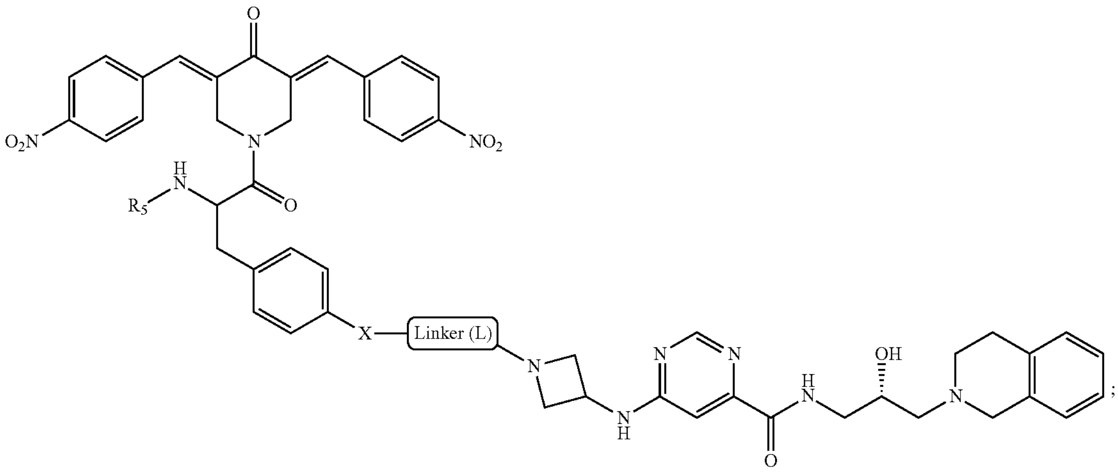

; and (I-5d)

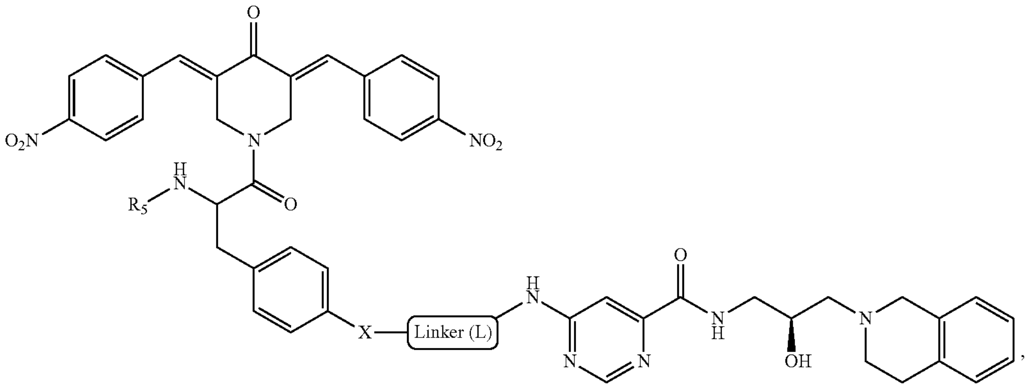

or a pharmaceutically acceptable salt or stereoisomer thereof.

Linkers

The linker ("L") provides a covalent attachment the targeting ligand and the degron. In some embodiments, the linker includes an alkylene chain (e.g., having 2-20 alkylene units). In some embodiments, the linker may include an alkylene chain or a bivalent alkylene chain, either of which may be interrupted by, and/or terminate (at either or both termini) with at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker may include a $C_1$-$C_{12}$ alkylene chain terminating in an NH— group wherein the nitrogen is also bound to the degron.

In some embodiments, the linker includes an alkylene chain having 1-10 alkylene units and is interrupted by or terminates in

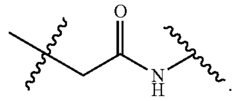 [SMILES: *CC(=O)N*]

.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of alkylene linkers that may be suitable for use in the present invention include the following:

(L1)

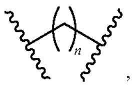

, wherein n is an integer of 1-12 ("of" meaning inclusive), e.g., 1-12, 1-11, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

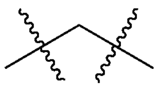

;

(L1-b)

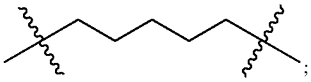

;

(L1-c)

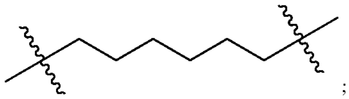

;

(L1-d)

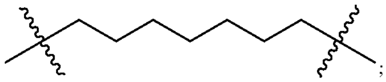

; and (L1-e)

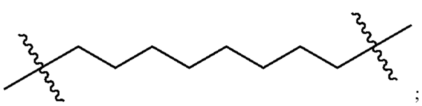

;

alkylene chains terminating in a functional group (as described above), examples of which are as follows:

(L2-a)

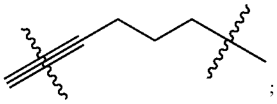

;

-continued (L2-b)

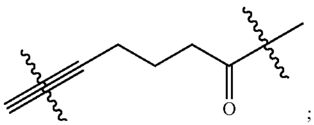

;

(L2-c)

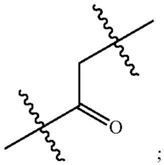

;

(L2-d)

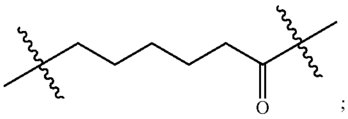

;

(L2-e)

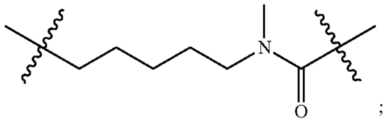

;

(L2-f)

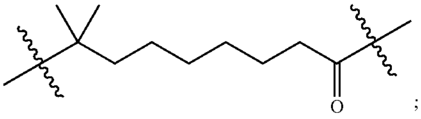

; and (L2-g)

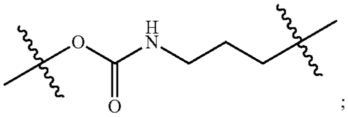

;

alkylene chains interrupted by a functional group (as described above), examples of which are as follows:

(L3-a)

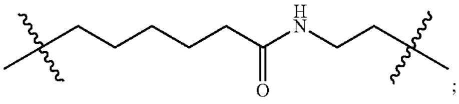

;

(L3-b)

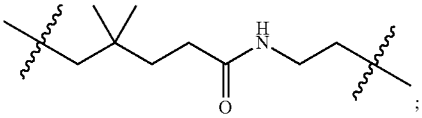

;

(L3-c)

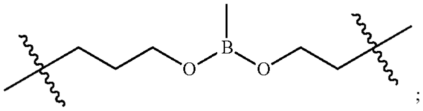

; and (L3-d)

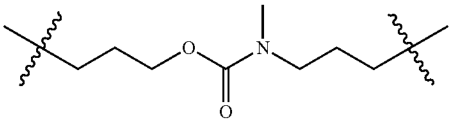

;

alkylene chains interrupted by or terminating with a heterocyclene group, e.g., (L4)

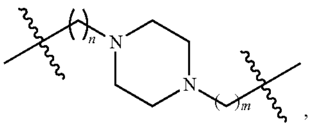

(L4), wherein m and n are independently integers of 0-10, representative examples of which include:

(L4-a)

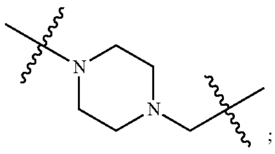

;

(L4-b)

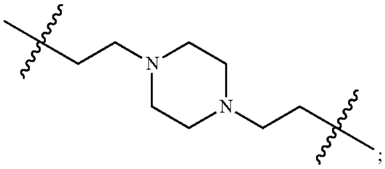

;

(L4-c)

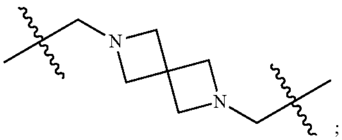

;

(L4-d)

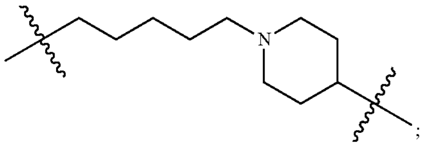

; and (L4-e)

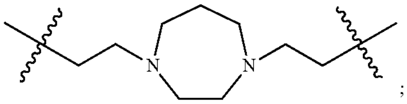

;

alkylene chains interrupted by amide, heterocyclene and/or aryl groups, examples of which include:

(L5-a)

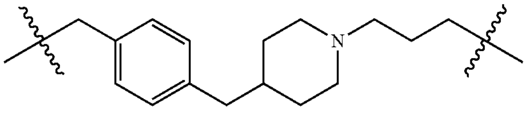

; and (L5-b)

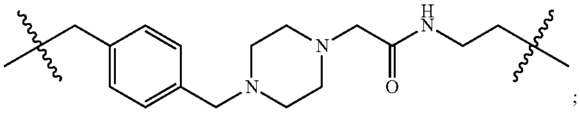

;

alkylene chains interrupted by heterocyclene and aryl groups, and a heteroatom, examples of which include:

(L6-a)

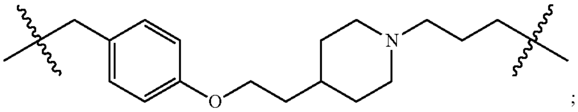

;

(L6-b)

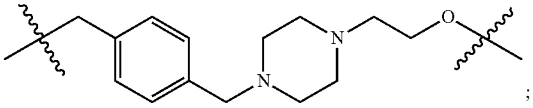

; and (L6-c)

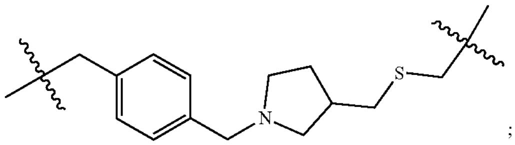

;

and alkylene chains interrupted by a heteroatom such as N, O or B, e.g., (L7)

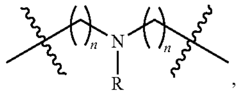

, wherein each n is independently an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is (L7-a)

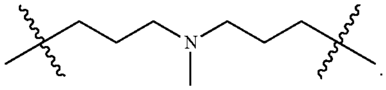

.

In some embodiments, the linker may include a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In some embodiments, the linker includes a polyethylene glycol chain having 2-8 PEG units and terminating in H

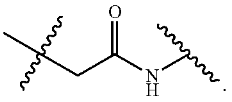 [SMILES: *CC(=O)N*]

Representative examples of linkers that include a polyethylene glycol chain include:

(L8)

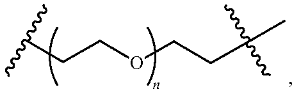

, wherein n is an integer of 2-10, examples of which include:

(L8-a)

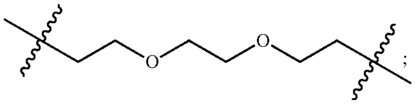

;

(L8-b)

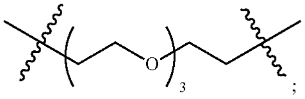

;

(L8-c)

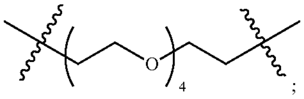

; and (L8-d)

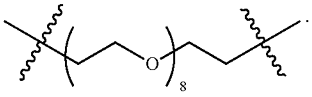

In some embodiments, the polyethylene glycol linker may terminate in a functional group, representative examples of which are as follows:

(L9-a)

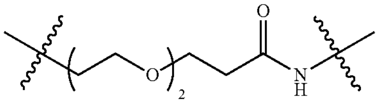

;

(L9-b)

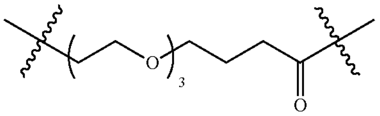

;

(L9-c)

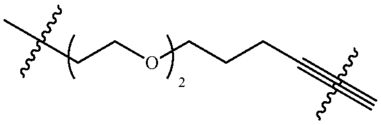

;

(L9-d)

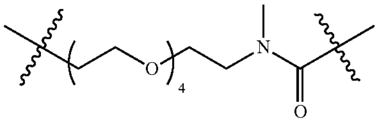

; and (L9-e)

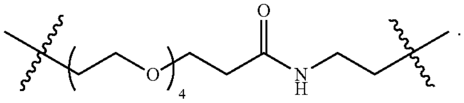

In other embodiments, the linker is represented by any one of structures:

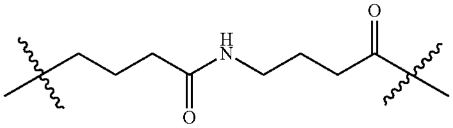

;

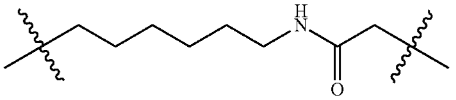

;

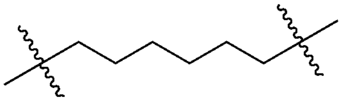

;

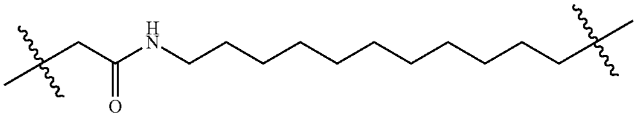

;

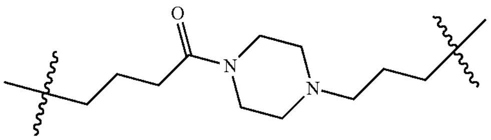

;

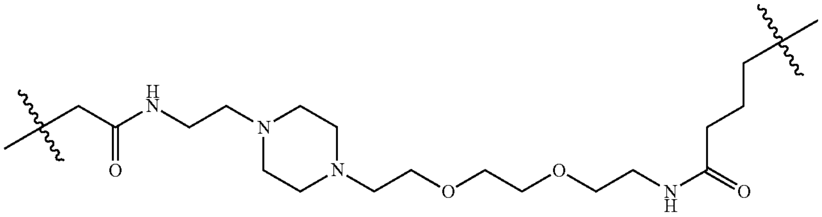

;

-continued
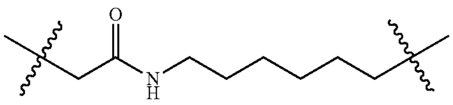
;
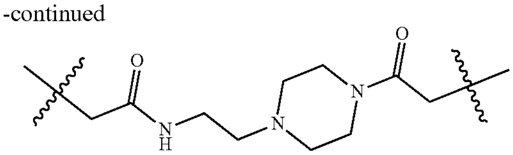
;
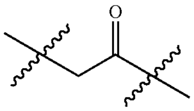
;
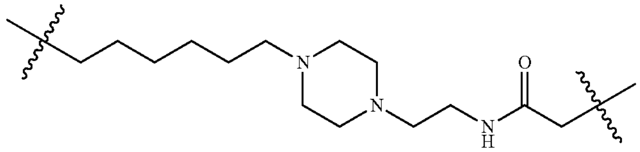
; and
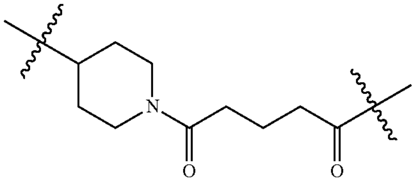
.
In some embodiments, the bifunctional compounds of the present invention have the following structures:
(1)
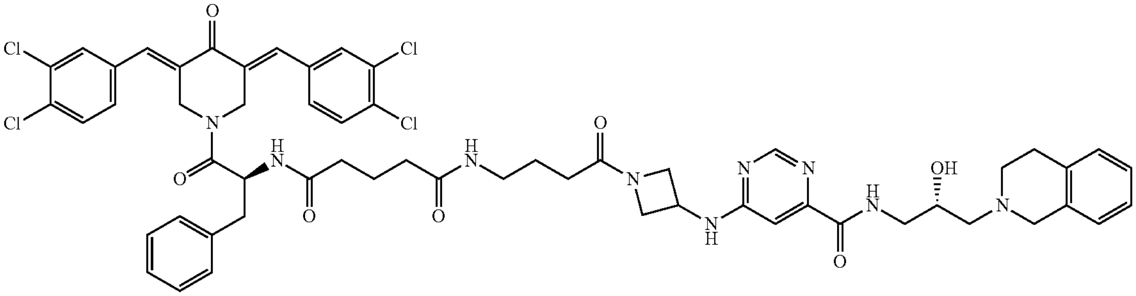
;
(2)
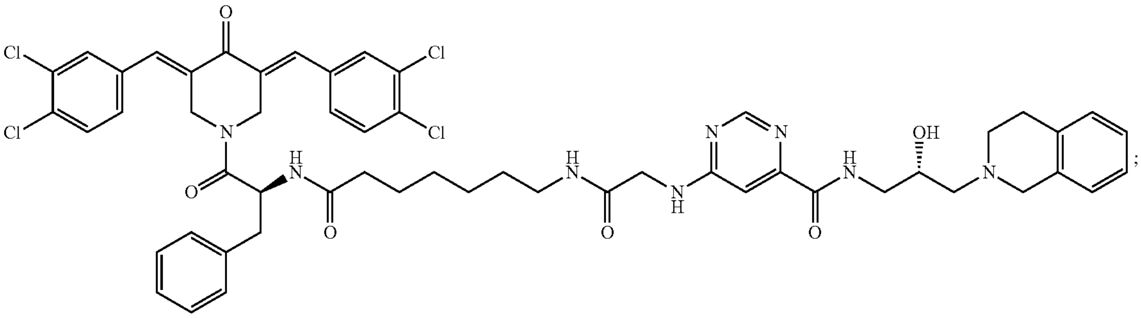
;

-continued
(3)
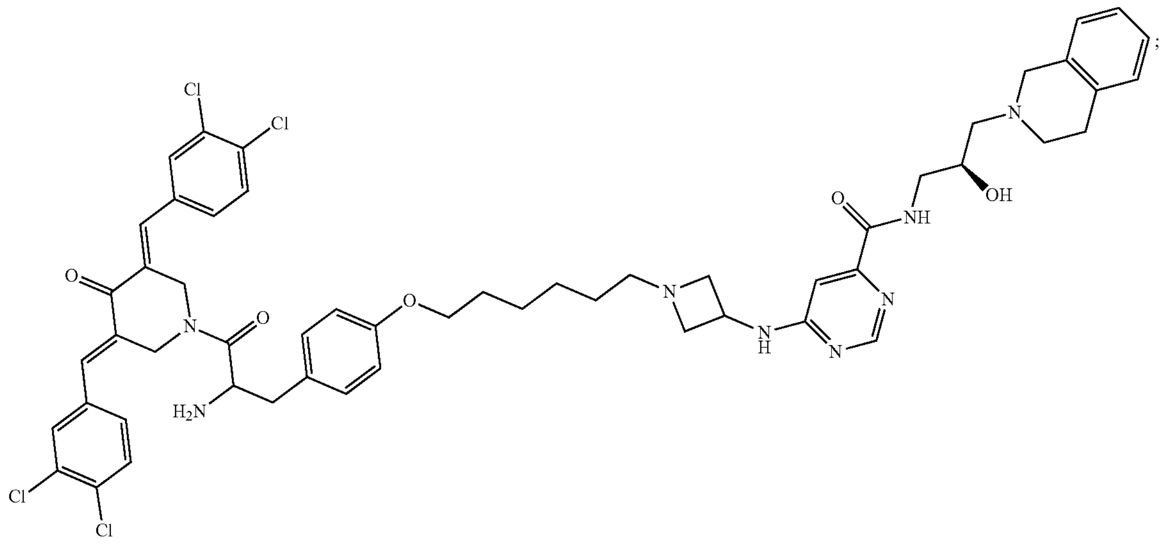
(4)
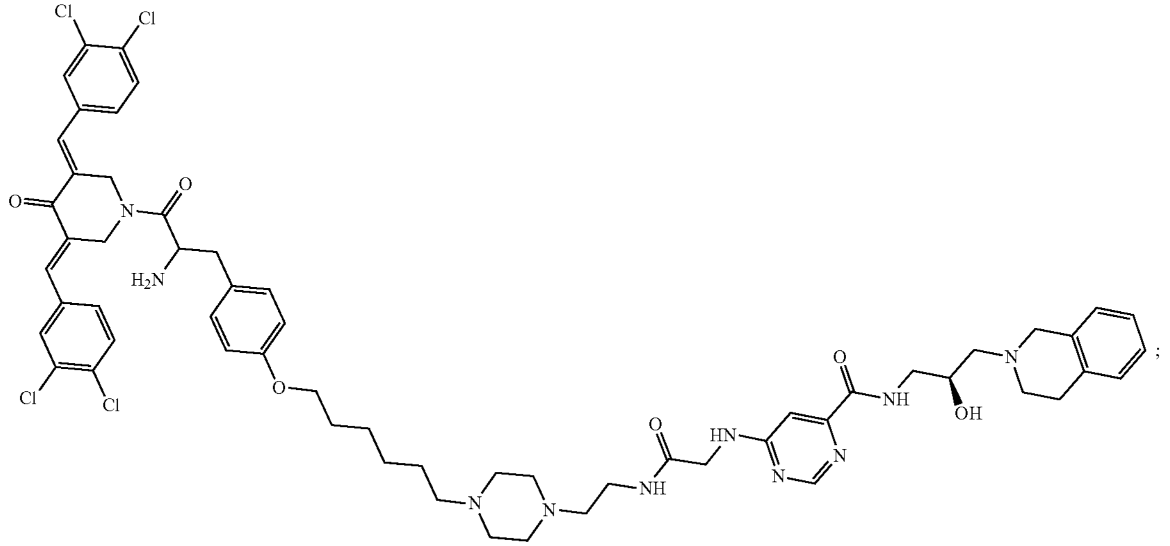
(5)
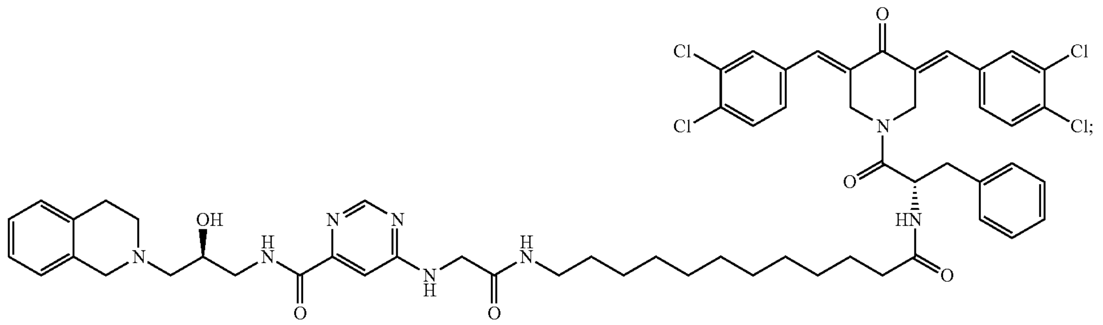

-continued
(6)
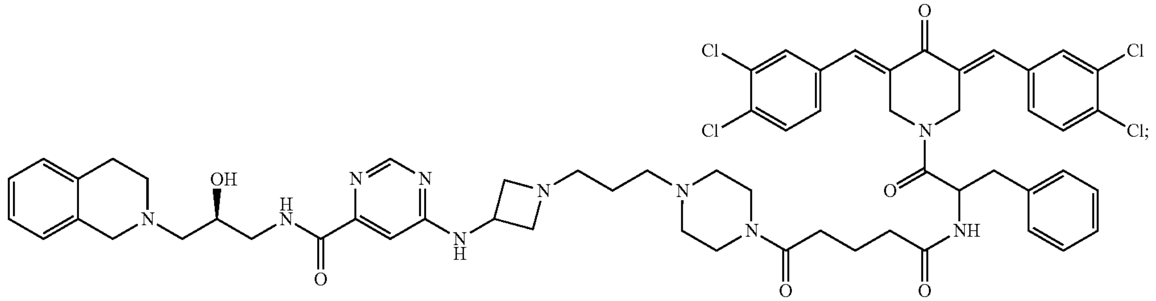
(7)
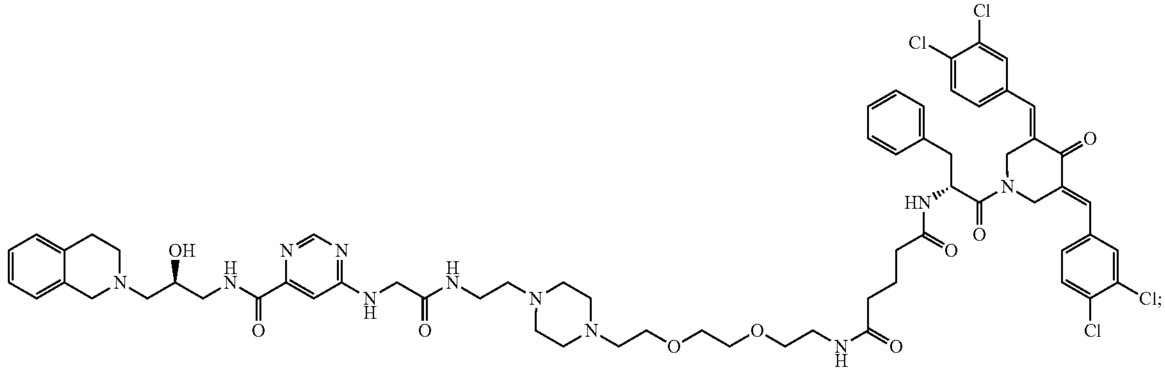
(8)
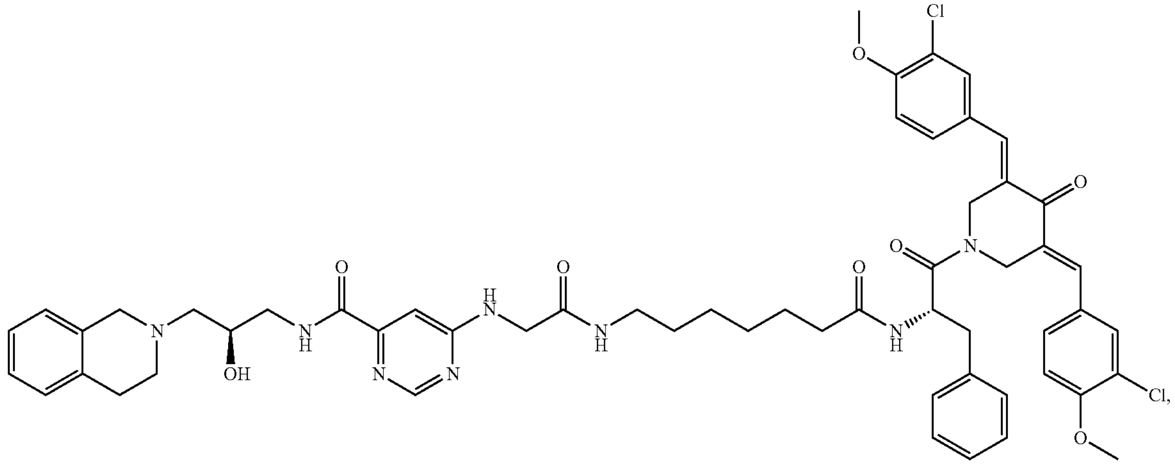
(9)
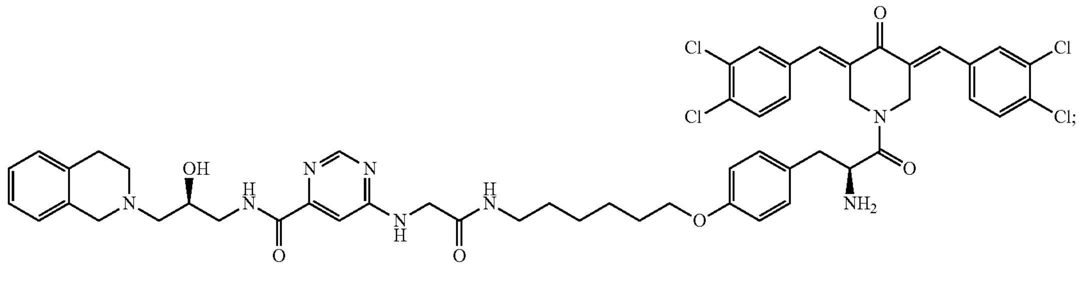

-continued
(10)
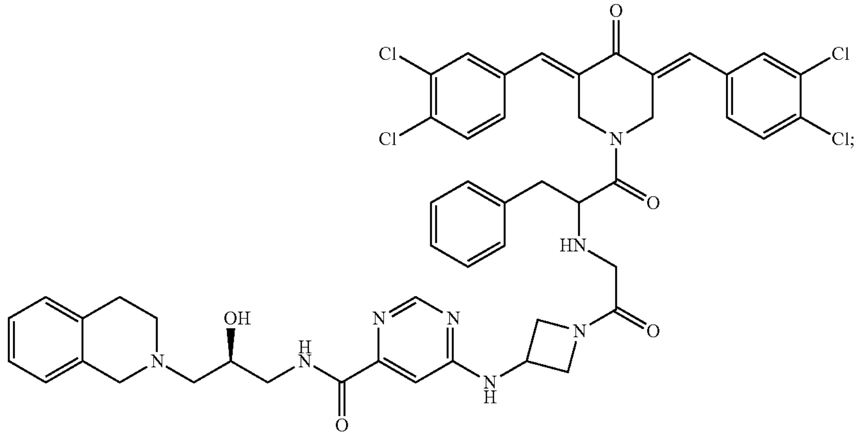
(11)
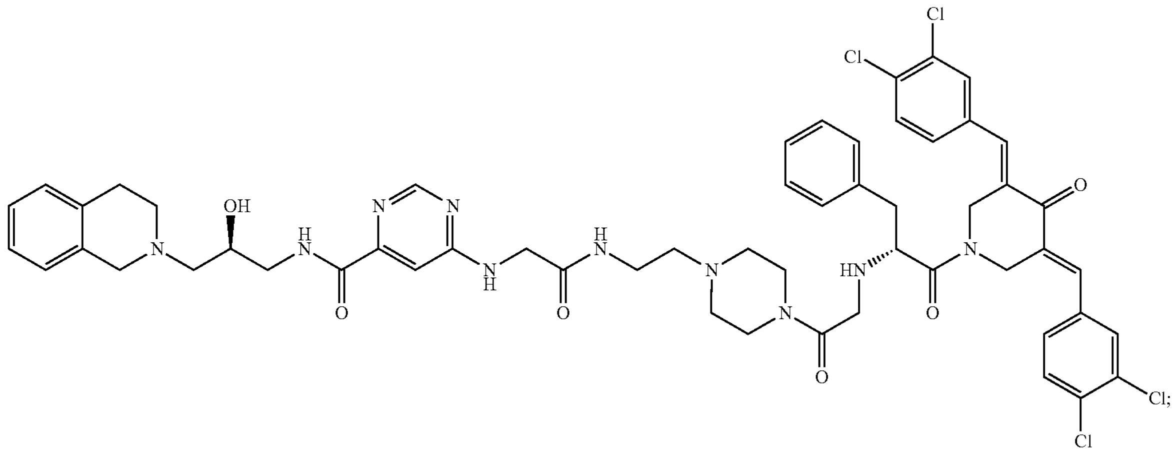
(12)
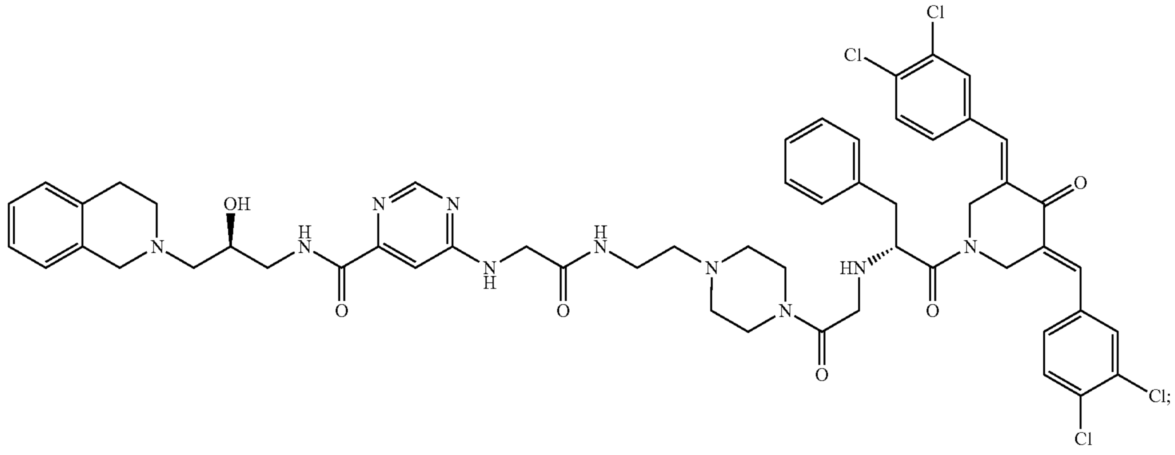

-continued (13)

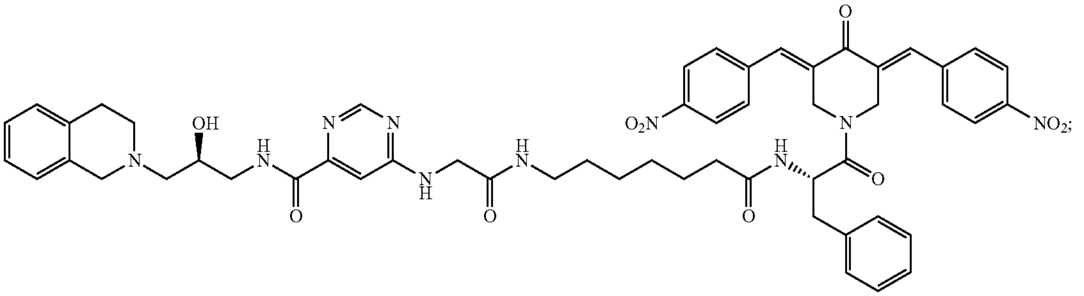

and (14)

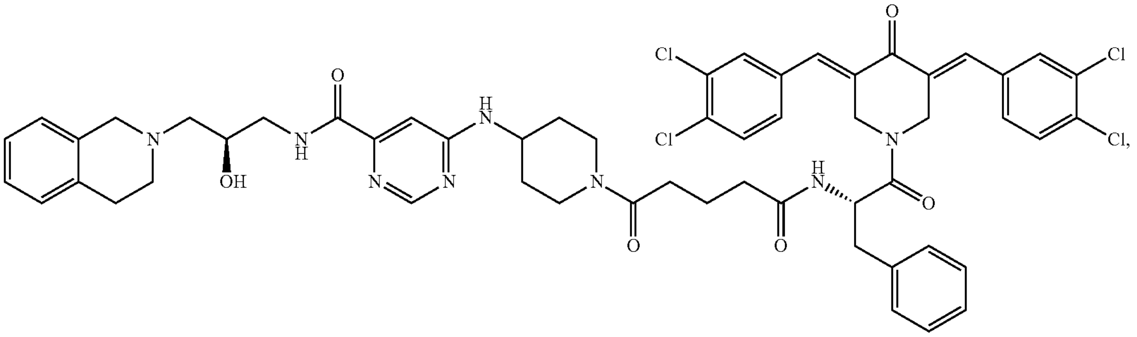

, or a pharmaceutically acceptable salt, or stereoisomer thereof.

Bifunctional compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Bifunctional compounds of formula (I) may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In some embodiments, the bifunctional compound of formula (I) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

In addition, bifunctional compounds of formula (I) embrace N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds.

Methods of Synthesis

In some embodiments, the present invention is directed to a method for making a bifunctional compound of formula (I) or a pharmaceutically acceptable salt or stereoisomer thereof. Broadly, the inventive compounds or pharmaceutically acceptable salts or stereoisomers thereof, may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of a bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may further include one or more pharmaceutically acceptable excipients.

Broadly, bifunctional compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrastemal injection, or infusion techniques, intraocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the bifunctional compound may be administered relatively quickly such as in the case of a single-dose treatment and/or an acute condition.

In some embodiments, the bifunctional compounds are formulated for oral or intravenous administration (e.g., systemic intravenous injection).

Accordingly, bifunctional compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipient such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bifunctional compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The bifunctional compounds may be formulated for buccal or sublingual administration, examples of which include tablets, lozenges and gels.

The bifunctional compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum comeum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or a pharmaceutically acceptable salt or a stereoisomer thereof, or a composition including a bifunctional compound of formula (I) or a pharmaceutically acceptable salt or a stereoisomer thereof, effective in producing the desired therapeutic response in a particular patient suffering from a disease or disorder characterized or mediated by aberrant PRMT5 activity. The term "therapeutically effective amount" thus includes the amount of a bifunctional compound of the invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amount of PRMT5 in diseased cells.

The total daily dosage of the bifunctional compounds and usage thereof may be decided in accordance with standard medical practice, e.g., by the attending physician using sound medical judgment. The specific therapeutically effective dose for any particular subject may depend upon one or more of a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the bifunctional compound; and like factors well known in the medical arts (see, for example, *Goodman and Gilman's, The Pharmacological Basis of Therapeutics,* 10th Edition, A. Gilman, J. Hardman and L. Limbird, eds., McGraw-Hill Press, 155-173, 2001).

Bifunctional compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of a bifunctional compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving aberrant (e.g., dysfunctional or dysregulated) PRMT5 activity, e.g., elevated levels of PRMT5 or otherwise functionally abnormal PRMT5 relative to a non-pathological state, that entails administration of a therapeutically effective amount of a bifunctional compound formula (I) or a pharmaceutically acceptable salt or stereoisomer thereof to a subject in need thereof.

A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g., hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus *foliaceus*, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In other embodiments, the methods are directed to treating subjects having cancer. Broadly, the bifunctional compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers include adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with the bifunctional compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), adenocarcinoma, small cell carcinoma, large cell carcinoma, squamous cell carcinoma, and mesothelioma. Lung cancer includes "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 rearrangement, lung adenocarcinoma, and squamous cell lung carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the cancer is breast cancer (e.g., triple-negative breast cancer), colorectal cancer, gastric cancer, lung cancer, nasopharyngeal cancer, ovarian cancer, a germ cell tumor, B-cell lymphoma, T-cell lymphoma, metastatic melanoma, neuroblastoma or glioblastoma. In some embodiments, the cancer is myelodysplastic syndrome (MDS) or acute myeloid leukemia (AML).

The bifunctional compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became intolerant to the particular treatment. Therapy may also be given as an adjuvant treatment, i.e., to prevent reoccurrence of cancer in patients with no currently detectable disease or after surgical removal of a tumor. Thus, in some embodiments, the bifunctional compounds may be administered to a patient who has received another therapy, such as chemotherapy, radioimmunotherapy, surgical therapy, immunotherapy, radiation therapy, targeted therapy or any combination thereof.

The methods of the present invention may entail administration of bifunctional compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days) followed by a 7-day "off" period. In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of five days.

Combination Therapy

Bifunctional compounds of formula (I) may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bifunctional compound of formula (I) in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be suitable for use in combination with the inventive bifunctional compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bifunctional antibodies) and CAR-T therapy.

In some embodiments, a bifunctional compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

In some embodiments involving cancer treatment, the bifunctional compound of formula (I) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, the bifunctional compound of formula (I) may be used in combination with at least one other anti-cancer agent, examples of which include poly ADP-ribose polymerase (PARP) inhibitors, such as Lynparza® (olaparib) and Talzenna® (talazoparib)(e.g., to treat triple-negative breast cancer and advanced-stage HER2-negative breast cancer in people with a BRCA1 or BRCA2 mutation), Tecentriq® (atezolizumab) in combination with Abraxane® (albumin-bound paclitaxel or nab-paclitaxel) (e.g., to treat unresectable locally advanced or metastatic triple-negative, PD-L1-positive breast cancer), lenalidomide and antithymocyte-globulin (ATG) (e.g., to treat myelodysplastic syndromes (MDS)), azacitidine and decitabine (5-aza-2'-deoxycytidine) (e.g., to treat MDS, chronic myelomonocytic leukemia (CMML), and acute myeloid leukemia (AML)), cytarabine, daunorubicin (daunomycin) and idarubicin (e.g., to treat AML).

Pharmaceutical Kits

The present bifunctional compounds and/or compositions containing them may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a bifunctional compound of formula (I) or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of N1-((S)-1-(3,5-bis((E)-3,4-dichlorobenzylidene)-4-oxopiperidin-1-yl)-1-oxo-3-phenylpropan-2-yl)-N5-(4-(3-((6-(((S)-3-(3,4-dihydroisoquinolin-2(1H)-yl)-2-hydroxypropyl)carbamoyl)pyrimidin-4-yl)amino)azetidin-1-yl)-4-oxobutyl)glutaramide (1)

(1)

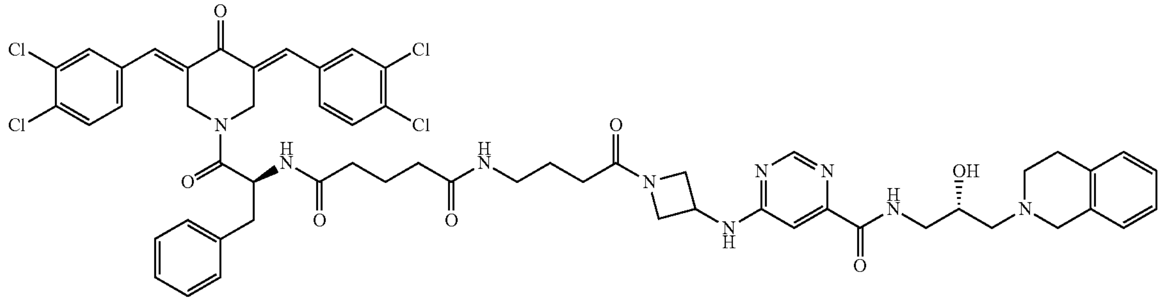

Compound 1 was prepared in an analogous manner to compound 10 in Example 10 (below) from 5-(((R)-1-(3,5-bis((E)-3,4-dichlorobenzylidene)-4-oxopiperidin-1-yl)-1-oxo-3-phenylpropan-2-yl)amino)-5-oxopentanoic acid (45% yield).

Example 2: Synthesis of 6-((2-((7-(((S)-1-(3,5-bis((E)-3,4-dichlorobenzylidene)-4-oxopiperidin-1-yl)-1-oxo-3-phenylpropan-2-yl)amino)-7-oxoheptyl)amino)-2-oxoethyl)amino)-N-((R)-3-(3,4-dihydroisoquinolin-2(1H)-yl)-2-hydroxypropyl)pyrimidine-4-carboxamide (2)

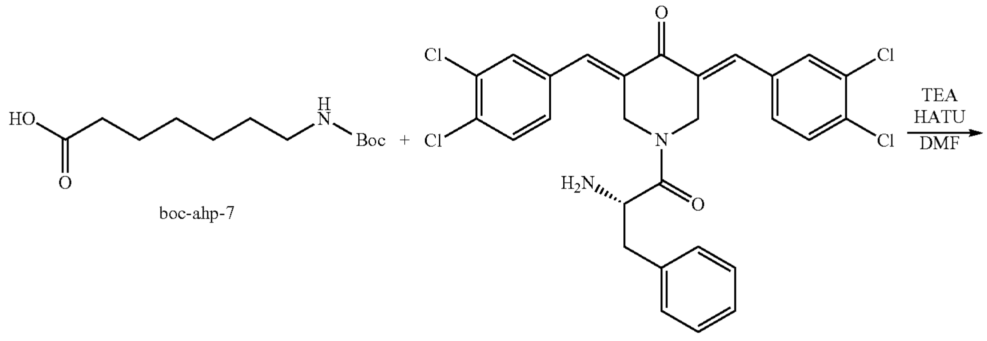

boc-ahp-7

RA190

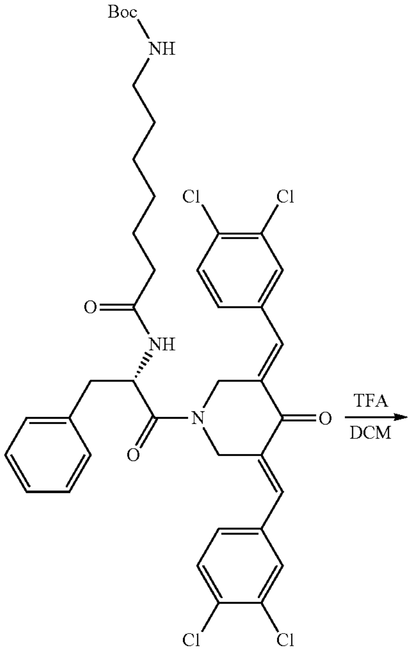

-continued

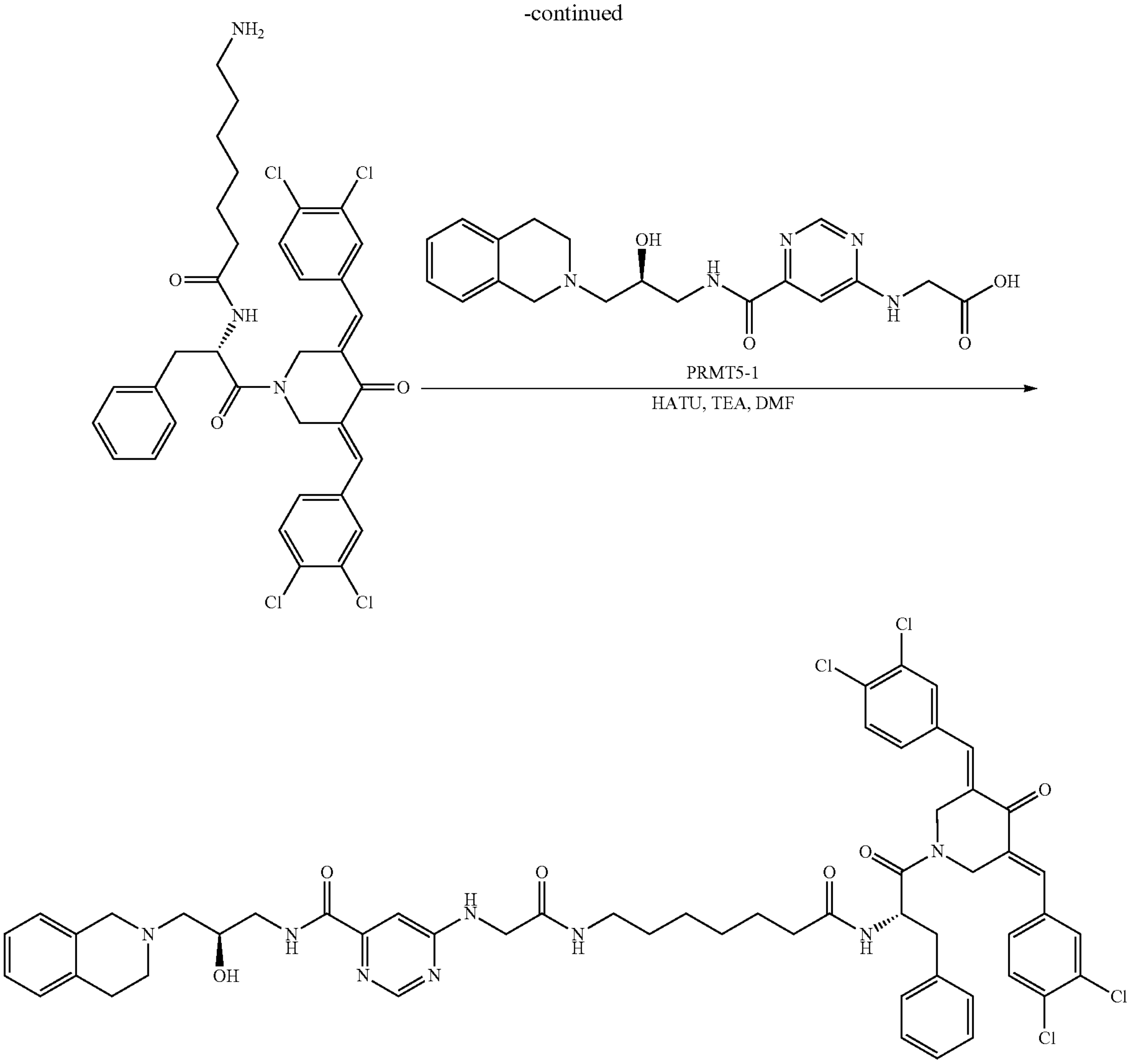

2

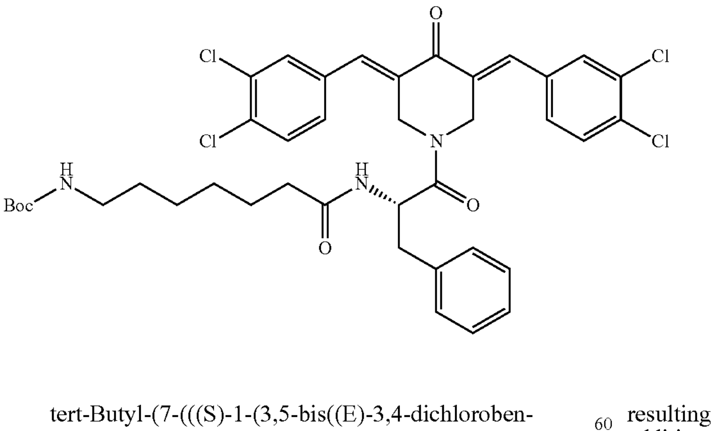

tert-Butyl-(7-(((S)-1-(3,5-bis((E)-3,4-dichlorobenzylidene)-4-oxopiperidin-1-yl)-1-oxo-3-phenylpropan-2-yl)amino)-7-oxoheptyl)carbamate To a 25-mL round bottom flask containing a solution of RA190 (50.0 mg, 89.0 μmol, 1.0 eq) and boc-ahp-7 (26.3 mg, 107.1 μmol, 1.2 eq) in DMF (300 μL), triethylamine (62.0 μL, 446.1 μmol, 5 eq) was added dropwise. The resulting mixture was stirred for 5 minutes before the addition of 1-[bis(dimethylamino)methylene]-1H-1,2,3-triazolo[4,5-b]pyridinium 3-oxide hexafluorophosphate (HATU) (33.9 mg, 89.0 μmol, 1.0 eq). The reaction was stirred for 30 minutes (until the starting material was depleted as determined by by mass spectrometry (MS)). The reaction mixture was purified by preparative high-performance liquid chromatography (prep-HPLC) to afford tert-butyl-(7-(((S)-1-(3,5-bis((E)-3,4-dichlorobenzylidene)-4- oxopiperidin-1-yl)-1-oxo-3-phenylpropan-2-yl)amino)-7-oxoheptyl)carbamate (34.2 mg, 43.2 μmol, 48.5%).

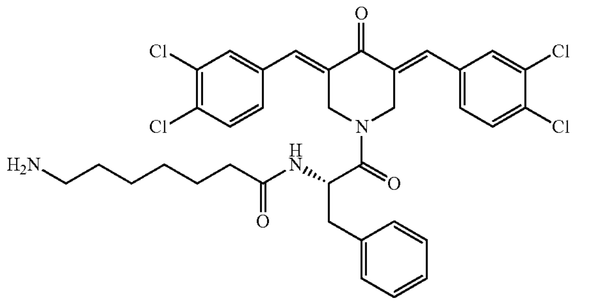 [SMILES: NCCCCCCC(=O)N[C@@H](Cc1ccccc1)C(=O)N1C/C(=C\c2ccc(Cl)c(Cl)c2)C(=O)/C(=C/c2ccc(Cl)c(Cl)c2)C1]

7-Amino-N-((S)-1-(3,5-bis((E)-3-chloro-4-methoxy-benzylidene)-4-oxopiperidin-1-yl)-1-oxo-3-phenyl-propan-2-yl)heptanamide To a 25-mL round bottom flask containing a solution of tert-butyl-(7-(((S)-1-(3,5-bis((E)-3,4-dichlorobenzylidene)-4-oxopiperidin-1-yl)-1-oxo-3-phenylpropan-2-yl)amino)-7-oxoheptyl)carbamate (70 mg, 88.9 μmol, 1 eq) in DCM (4 mL) at 0° C., TFA (1 mL) was added dropwise. The resulting mixture was stirred for 2 hours. The reaction was then diluted with water and was lipolyzed to afford 7-amino-N-((S)-1-(3,5-bis((E)-3-chloro-4-methoxybenzylidene)-4-oxopiperidin-1-yl)-1-oxo-3-phenylpropan-2-yl)heptanamide. The crude product was used directly in the next reaction.

(2)

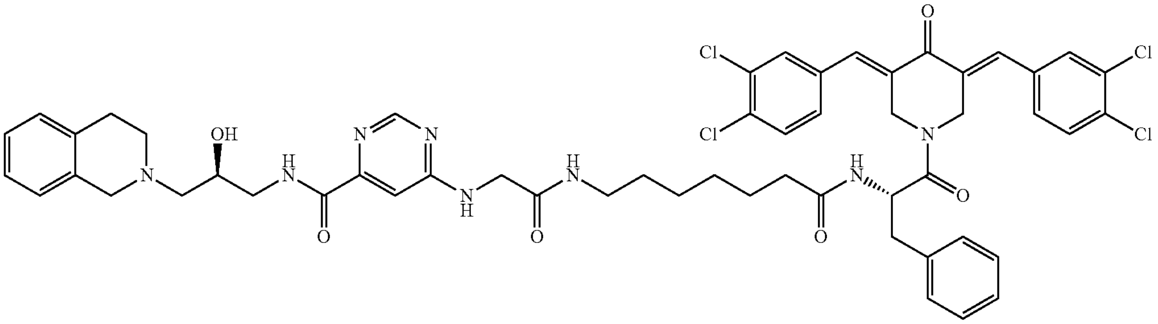

To a 25-mL round bottom flask containing a solution of PRMT5-1 (11.2 mg, 24.1 μmol, 1.0 eq) and 7-amino-N-((S)-1-(3,5-bis((E)-3-chloro-4-methoxybenzylidene)-4-oxopiperidin-1-yl)-1-oxo-3-phenylpropan-2-yl)heptanamide (20.0 mg, 24.1 μmol, 1.0 eq) in DMF (300 μL), triethylamine (16.8 μL, 120.1 μmol, 5.0 eq) was added dropwise. The resulting mixture was stirred for 5 minutes before the addition of hexafluorophosphate azabenzotriazole tetramethyl uranium (HATU) (11.06 mg, 24.1 μmol, 1.0 eq). The reaction was stirred for 30 minutes (until the starting material was depleted as determined by MS). The reaction was concentrated under a stream of nitrogen and was purified by flash chromatography (0-15% gradient MeOH:DCM) to afford impure compound 2 (21.51 mg 20.4, 84.7% yield). The isolated product was dissolved in 300 μL DCM and was further purified to yield compound 2 (2.73 mg, 2.6 μmol, 10.7% yield).

Example 3: Synthesis of 6-((1-(6-(4-(2-amino-3-(3,5-bis((E)-3,4-dichlorobenzylidene)-4-oxopiperidin-1-yl)-3-oxopropyl)phenoxy)hexyl)azetidin-3-yl)amino)-N-((S)-3-(3,4-dihydroisoquinolin-2(1H)-yl)-2-hydroxypropyl)pyrimidine-4-carboxamide (3)

(3)

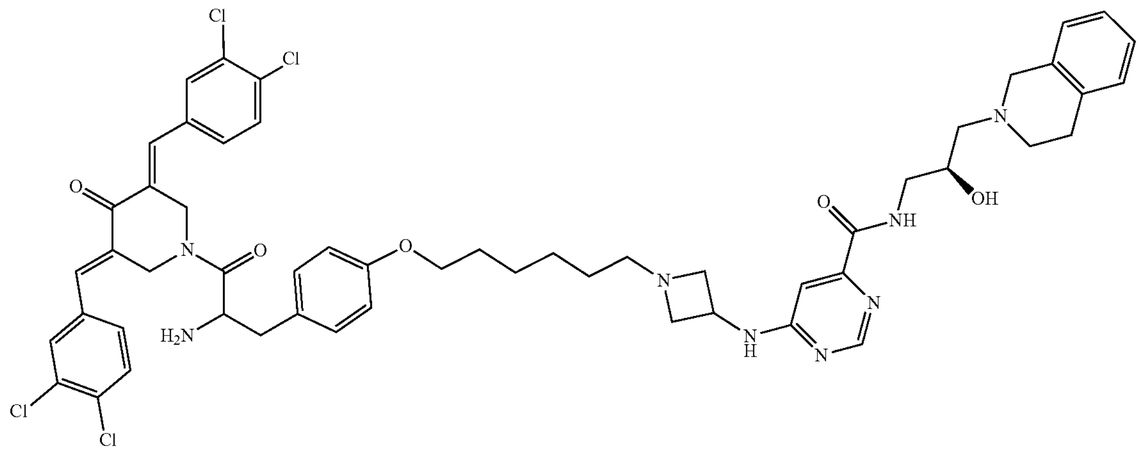

Compound 3 was prepared in an analogous manner to compound 9 in Example 9 (below) from PRMT5-46 (40% yield).

Example 4: Synthesis of 6-((2-((2-(4-(6-(4-(2-amino-3-(3,5-bis((E)-3,4-dichlorobenzylidene)-4-oxopiperidin-1-yl)-3-oxopropyl)phenoxy)hexyl)piperazin-1-yl)ethyl)amino)-2-oxoethyl)amino)-N-((S)-3-(3,4-dihydroisoquinolin-2(1H)-yl)-2-hydroxypropyl)pyrimidine-4-carboxamide (4)

(4)

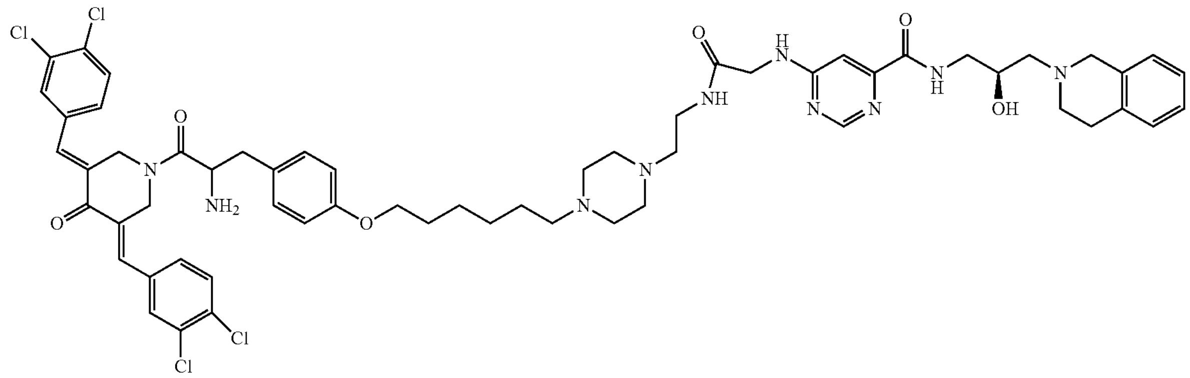

Compound 4 was prepared in an analogous manner to compound 9 in Example 9 from PRMT5-46 (40% yield).

Example 5: Synthesis of 6-((2-((12-(((S)-1-(3,5-bis((E)-3,4-dichlorobenzylidene)-4-oxopiperidin-1-yl)-1-oxo-3-phenylpropan-2-yl)amino)-12-oxododecyl)amino)-2-oxoethyl)amino)-N-((S)-3-(3,4-dihydroisoquinolin-2(1H)-yl)-2-hydroxypropyl)pyrimidine-4-carboxamide (5)

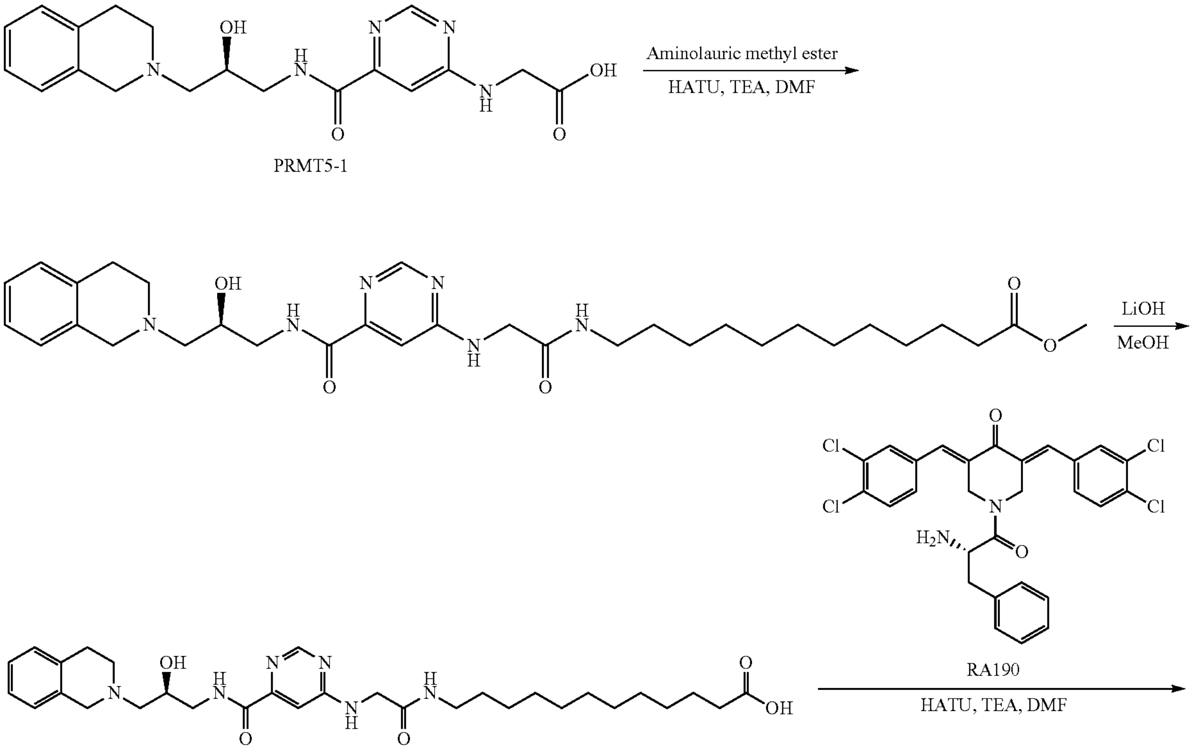

PRMT5-1

RA190

-continued

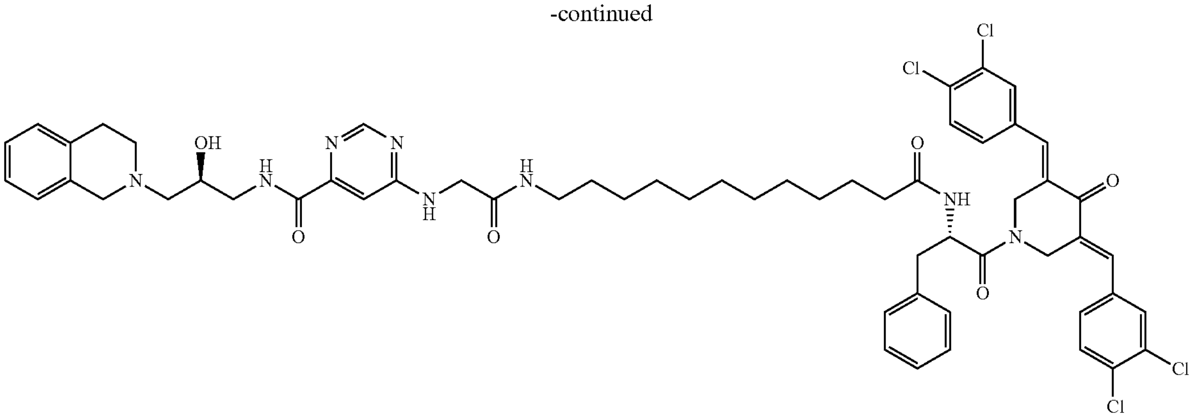

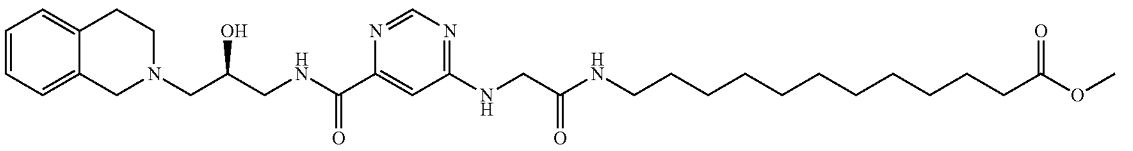

Methyl-(S)-12-(2-((6-((3-(3,4-dihydroisoquinolin-2(1H)-yl)-2-hydroxypropyl)carbamoyl)pyrimidin-4-yl)amino)acetamido)dodecanoate To a 25-mL round bottom flask containing a solution of PRMT5-1 (4.2 mg, 10.9 μmol, 1.0 eq) and 12-aminolauric methyl ester (2.89 mg, 10.9 μmol, 1.0 eq) in DMF (50 μL), triethylamine was added dropwise. The resulting mixture was stirred for 5 minutes before the addition of HATU (4.1 mg, 10.9 μmol, 1.0 eq). The reaction was stirred for 30 minutes (until the starting material was depleted by MS). The reaction was concentrated under a stream of nitrogen and was purified by flash chromatography (0-10% gradient MeOH:DCM) to afford methyl-(S)-12-(2-((6-((3-(3,4-dihydroisoquinolin-2(1H)-yl)-2-hydroxypropyl)carbamoyl)pyrimidin-4-yl)amino)acetamido)dodecanoate) as a relatively pure yellow oil (7.0 mg, 11.7 μmol).

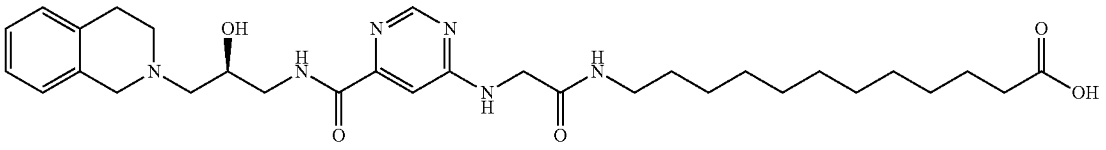 [SMILES: O=C(O)CCCCCCCCCCCNC(=O)CNc1cc(C(=O)NC[C@H](O)CN2CCc3ccccc3C2)ncn1]

(S)-12-(2-((6-((3-(3,4-Dihydroisoquinolin-2(1H)-yl)-2-hydroxypropyl)carbamoyl)pyrimidin-4-yl)amino)acetamido)dodecanoic Acid To a 25-mL round bottom flask containing a solution of methyl-(S)-12-(2-((6-((3-(3,4-dihydroisoquinolin-2(1H)-yl)-2hydroxypropyl)carbamoyl)pyrimidin-4-yl)amino)acetamido)dodecanoate) (3.5 mg, 5.9 μmol, 1.0 eq) in methanol (300 μL), aqueous LiOH (60 μL, 2 M) was added dropwise. The reaction was stirred for 3 hours (until the starting material was depleted as determined by MS). The reaction was concentrated under reduced pressure to afford (S)-12-(2-((6-((3-(3,4-dihydroisoquinolin-2(1H)-yl)-2-hydroxypropyl)carbamoyl)pyrimidin-4-yl)amino)acetamido)dodecanoic acid. The crude product was used directly in the next reaction.

(5)

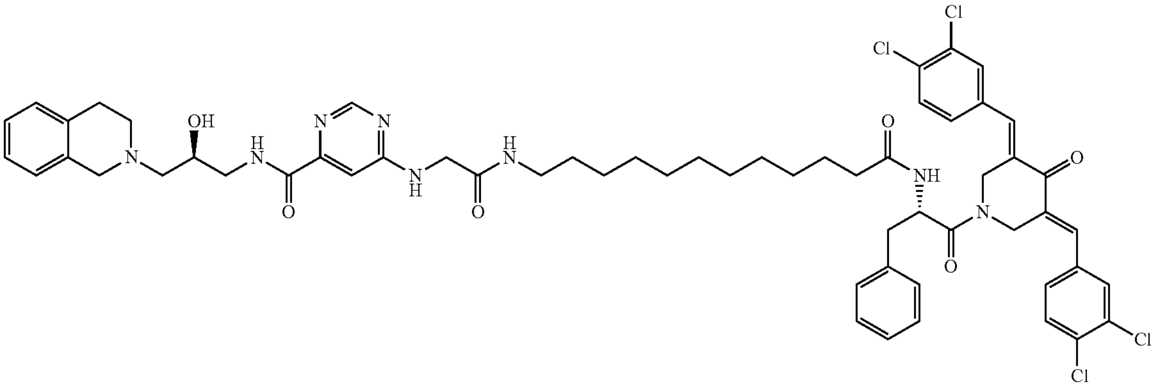

To a 25-mL round bottom flask containing a solution of (S)-12-(2-((6-((3-(3,4-dihydroisoquinolin-2(1H)-yl)-2-hydroxypropyl)carbamoyl)pyrimidin-4-yl)amino)acetamido) dodecanoic acid (3.5 mg, 5.9 μmol, 1.0 eq) and RA190 in DMF (100 μL), triethylamine was added dropwise. The mixture was stirred for 5 minutes before the addition of HATU (2.7 mg, 5.9 μmol, 1.0 eq). The resulting reaction mixture was stirred for 1 hour. The reaction mixture was diluted with DMF (200 μL) and was purified by HPLC to afford compound 5 (0.69 mg, 613 nM, 10% yield).

Example 6: Synthesis of 6-((1-(3-(4-(5-(((R)-1-(3,5-bis((E)-3,4-dichlorobenzylidene)-4-oxopiperidin-1-yl)-1-oxo-3-phenylpropan-2-yl)amino)-5-oxopentanoyl)piperazin-1-yl)propyl)azetidin-3-yl)amino)-N-((R)-3-(3,4-dihydroisoquinolin-2(1H)-yl)-2-hydroxypropyl)pyrimidine-4-carboxamide (6)

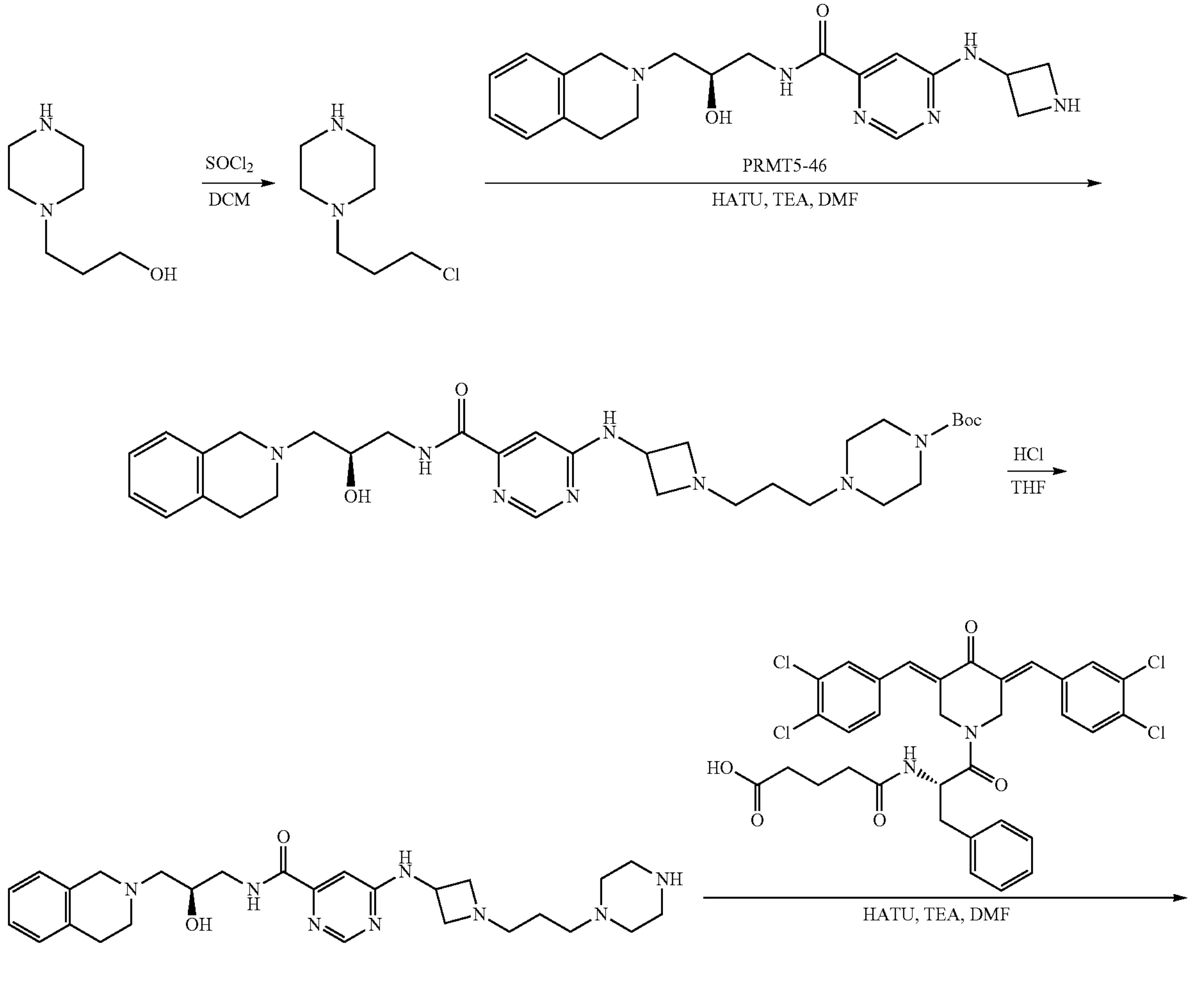

-continued

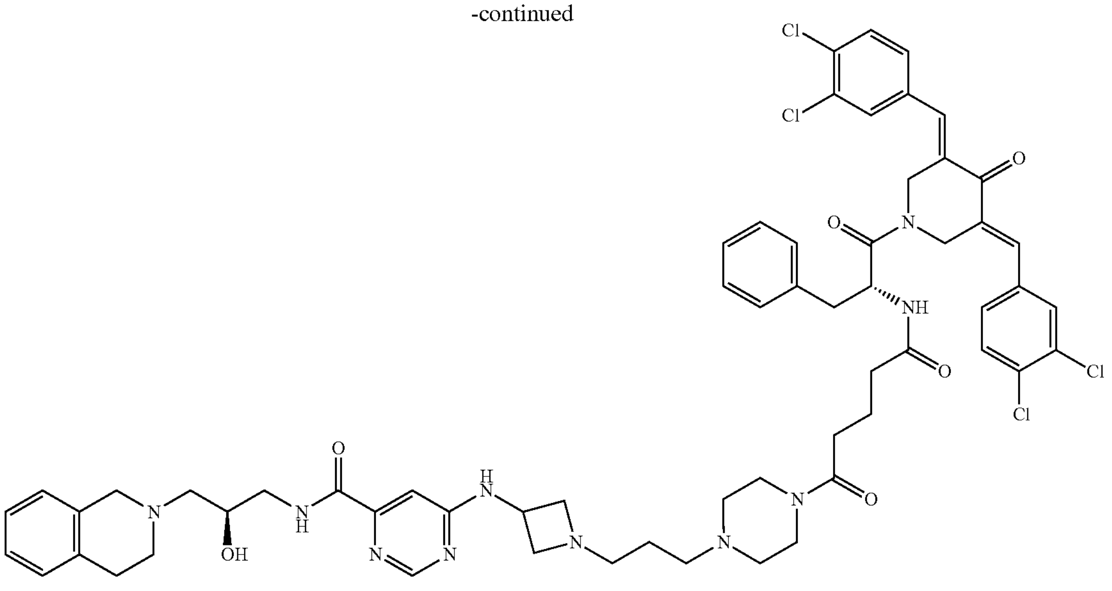

6

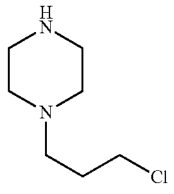

1-(3-Chloropropyl)piperazine

To a 25-mL round bottom flask containing a solution of 3-(piperazin-1-yl)propan-1-ol (77.2 mg, 316.4 μmol, 1.0 eq) in DCM (700 μL), thionyl chloride (34.1 μL, 474.6 μmol, 1.5 eq) was added dropwise. The resulting mixture was stirred at 23° C. for 2.5 hours. The reaction was then concentrated under reduced pressure and was purified by flash chromatography (0-10% DCM:MeOH gradient) to afford 1-(3-chloropropyl)piperazine (30.2 mg, 197.9 μmol, 63% yield).

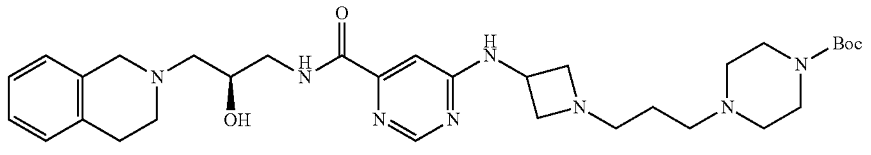 [SMILES: CC(C)(C)OC(=O)N1CCN(CCCN2CC(Nc3cc(C(=O)NC[C@@H](O)CN4CCc5ccccc5C4)ncn3)C2)CC1]

tert-Butyl-(R)-4-(3-(3-((6-((3-(3,4-dihydroisoquinolin-2(1H)-yl)-2-hydroxypropyl)carbamoyl)pyrimidin-4-yl)amino)azetidin-1-yl)propyl)piperazine-1-carboxylate To a 25-mL round bottom flask containing PRMT5-46 (10.5 mg, 27.4 μmol, 1.0 eq), 1-(3-chloropropyl)piperazine (8.66 mg, 32.9 μmol, 1.2 eq), potassium carbonate (7.58 mg, 54.9 μmol, 2.0 eq) and sodium iodide (1.23 mg, 13 μmol, 0.5 eq), DMF (100 μL) was added. The resulting solution was heated to 60° C. for 16 hours. The reaction temperature was increased to 70° C., and the reaction was heated at that temperature for 4 hours. The reaction mixture was allowed to cool to room temperature and then was purified by HPLC to afford tert-butyl-(R)-4-(3-(3-((6-((3-(3,4-dihydroisoquinolin-2(1H)-yl)-2-hydroxypropyl)carbamoyl)pyrimidin-4-yl)amino)azetidin-1-yl)propyl)piperazine-1-carboxylate (6.8 mg, 11.1 μmol, 41% yield).

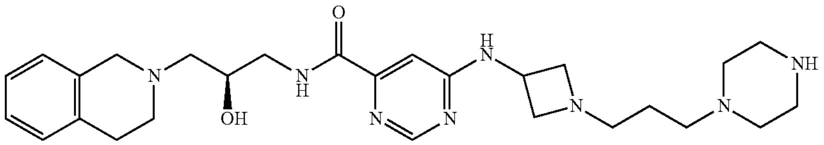 [SMILES: O=C(NC[C@@H](O)CN1CCc2ccccc2C1)c1cc(NC2CN(CCCN3CCNCC3)C2)ncn1]

(R)—N-(3-(3,4-Dihydroisoquinolin-2(1H)-yl)-2-hydroxypropyl)-6-((1-(3-(piperazin-1-yl)propyl)azetidin-3-yl)amino)pyrimidine-4-carboxamide To a 25-mL round bottom flask containing a solution of tert-butyl-(R)-4-(3-(3-((6-((3-(3,4-dihydroisoquinolin-2(1H)-yl)-2-hydroxypropyl)carbamoyl)pyrimidin-4-yl)amino)azetidin-1-yl)propyl)piperazine-1-carboxylate (4.2 mg, 6.9 μmol, 1.0 eq) in THF (1 mL), a solution of HCl in 1,4-dioxane (1 mL, 4.0 M) was added. The resulting mixture was stirred for 3 hours. The reaction mixture was then concentrated under reduced pressure and was used directly in the next reaction.

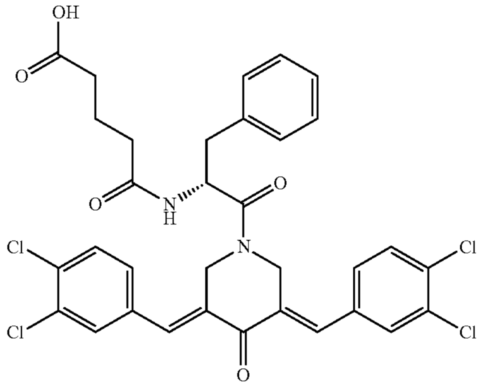 [SMILES: O=C(O)CCCC(=O)N[C@H](Cc1ccccc1)C(=O)N1C/C(=C\c2ccc(Cl)c(Cl)c2)C(=O)/C(=C/c2ccc(Cl)c(Cl)c2)C1]

5-(((R)-1-(3,5-Bis((E)-3,4-dichlorobenzylidene)-4-oxopiperidin-1-yl)-1-oxo-3-phenylpropan-2-yl)amino)-5-oxopentanoic Acid To a 25-mL round bottom flask containing a solution of RA190 (30 mg, 53.8 μmol, 1.0 eq) and glutaric anhydride (6.15 mg, 80.7 μmol, 1.5 eq) in MeCN (400 μL), triethylamine (29.9 μL, 215.2 μmol, 4.0 eq) was added. The reaction was stirred for 3 hours. The reaction mixture was concentrated under reduced pressure to afford 5-(((R)-1-(3,5-bis((E)-3,4-dichlorobenzylidene)-4-oxopiperidin-1-yl)-1-oxo-3-phenylpropan-2-yl)amino)-5-oxopentanoic acid. The crude product was directly used in the next step.

(6)

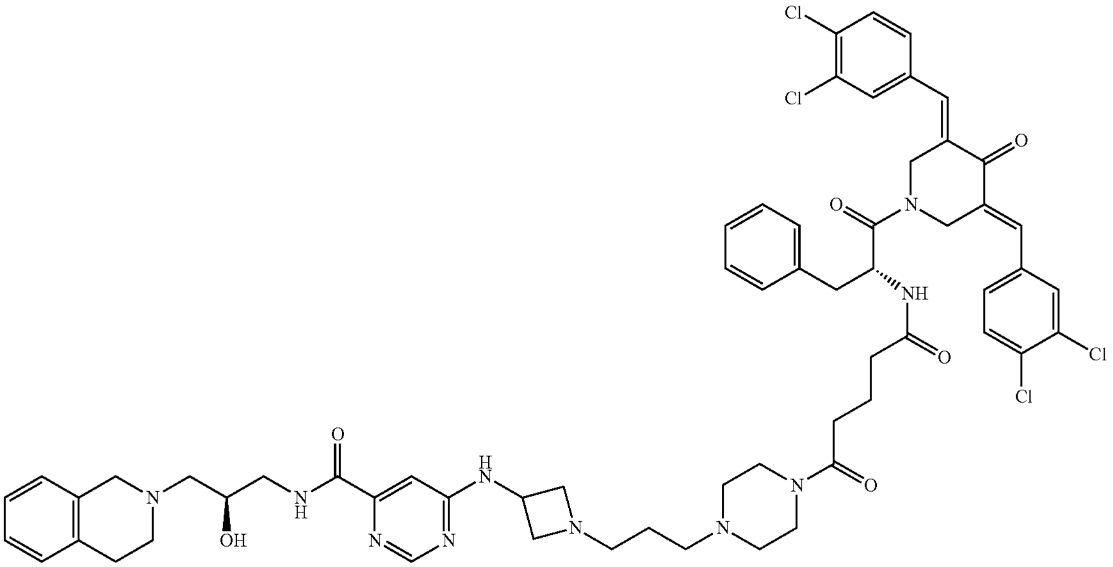

To a 25-mL round bottom flask containing a solution of (R)—N-(3-(3,4-dihydroisoquinolin-2(1H)-yl)-2-hydroxypropyl)-6-((1-(3-(piperazin-1-yl)propyl)azetidin-3-yl)amino)pyrimidine-4-carboxamide (4.2 mg, 8.2 μmol, 1.0 eq) and 5-(((R)-1-(3,5-bis((E)-3,4-dichlorobenzylidene)-4-oxopiperidin-1-yl)-1-oxo-3-phenylpropan-2-yl)amino)-5-oxopentanoic acid (5.5 mg, 8.2 μmol, 1.0 eq) in DMF (100 μL), triethylamine (5.75 μL, 41.2 μmol, 5.0 eq) was added dropwise. The resulting mixture was stirred for 5 minutes before the addition of HATU (3.1 mg, 8.2 μmol, 1.0 eq). The reaction was stirred for 1 hour. The reaction mixture was concentrated under a stream of nitrogen and was purified by flash chromatography to afford compound 6 (2.48 mg, 2.12 μmol, 26% yield).

Example 7: Synthesis of N1-((R)-1-(3,5-bis((E)-3,4-dichlorobenzylidene)-4-oxopiperidin-1-yl)-1-oxo-3-2-yl)-N5-(2-(2-(2-(4-(2-(2-((6-(((S)-3-(3,4-dihydroisoquinolin-2(1H)-yl)-2-hydroxypropyl)carbamoyl)pyrimidin-4-yl)amino)acetamido)ethyl)piperazin-1-yl)-2-oxoethoxy)ethoxy)ethyl)glutarimide (7)

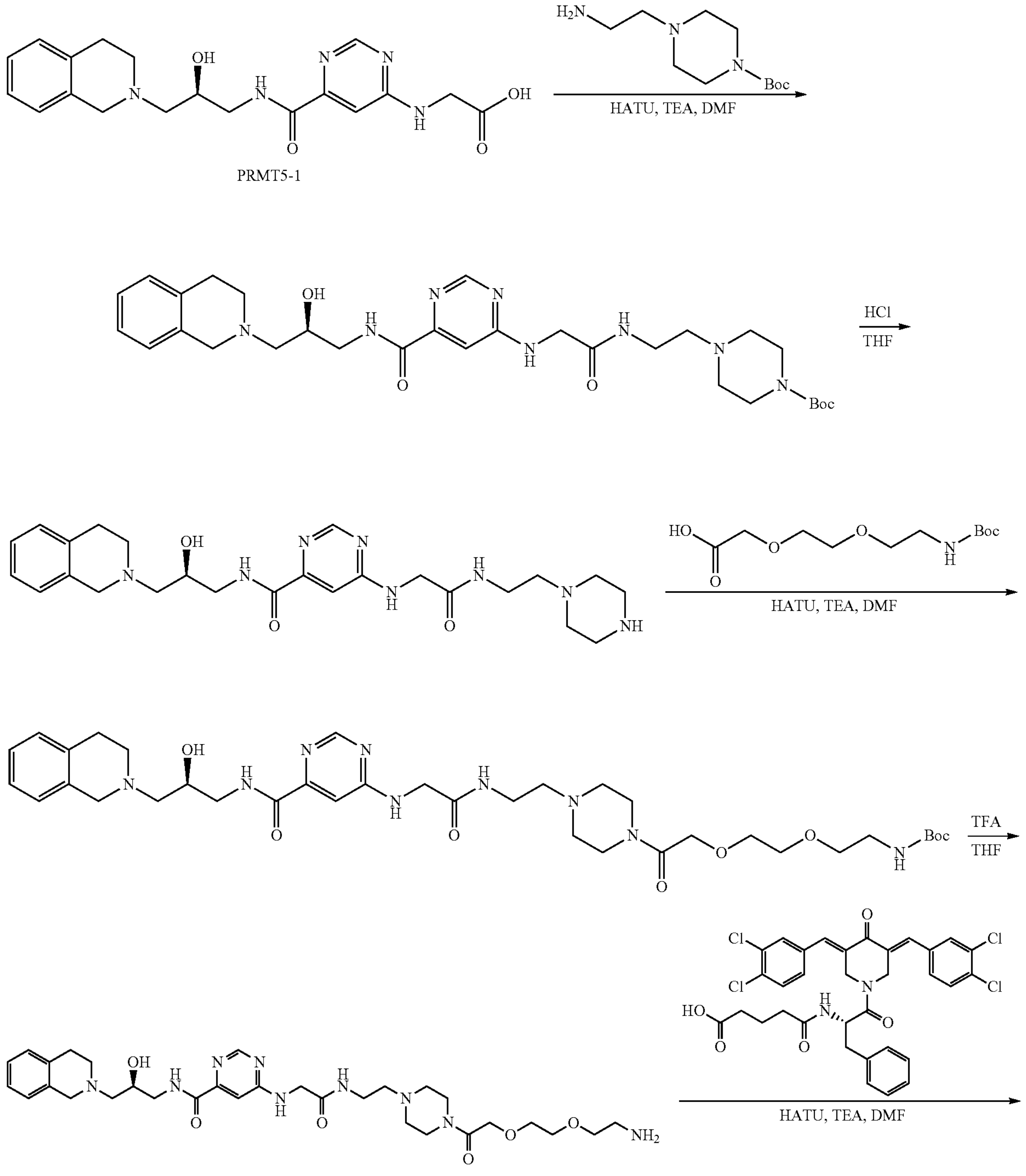

-continued

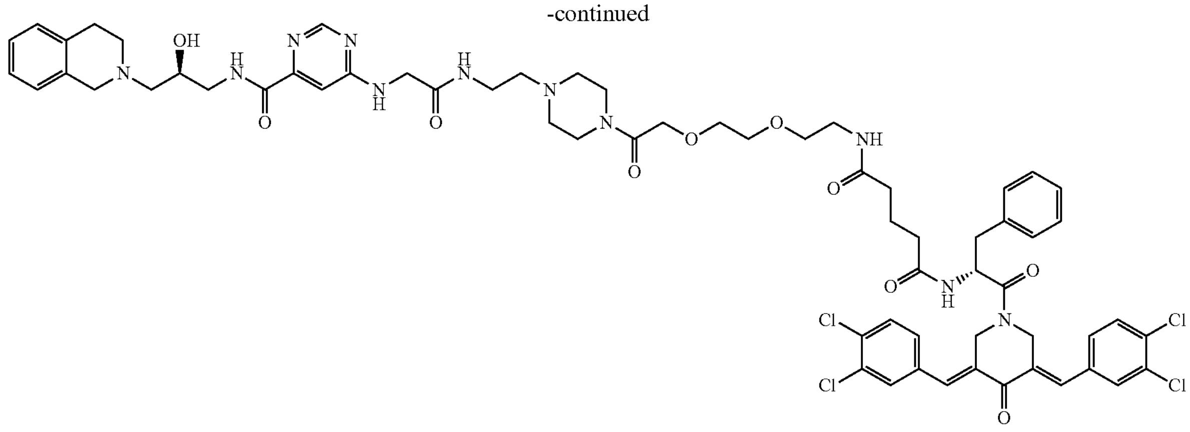

7

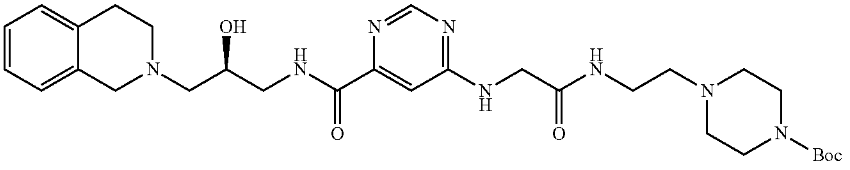 [SMILES: CC(C)(C)OC(=O)N1CCN(CCNC(=O)CNc2cc(C(=O)NC[C@H](O)CN3CCc4ccccc4C3)ncn2)CC1]

tert-Butyl-(S)-4-(2-(2-((6-((3-(3,4-dihydroisoquinolin-2(1H)-yl)-2-hydroxypropyl)carbamoyl)pyrimidin-4-yl)amino)acetamido)ethyl)piperazine-1-carboxylate To a 25-mL round bottom flask containing a solution of PRMT5-1 (6.2 mg, 16.1 μmol, 1.0 eq) and tert-butyl 4-(2-aminoethyl)piperazine-1-carboxylate (3.7 mg, 16.1 μmol, 1.0 eq) DMF (100 μL), triethylamine (11.3 μL, 80.9 μmol, 5 eq) was added dropwise. The resulting solution was stirred for 5 minutes before the addition of HATU (6.6 mg, 16.1 μmol, 1.0 eq). The reaction was stirred for 30 minutes (until the starting material was depleted as determined by MS). The reaction mixture was concentrated under a stream of nitrogen and was purified by flash chromatography (0-10% gradient MeOH:DCM) to afford tert-butyl-(S)-4-(2-(2-((6-((3-(3,4-dihydroisoquinolin-2(1H)-yl)-2-hydroxypropyl)carbamoyl)pyrimidin-4-yl)amino)acetamido)ethyl)piperazine-1-carboxylate). (9.0 mg, 11.7 μmol, 94% yield).

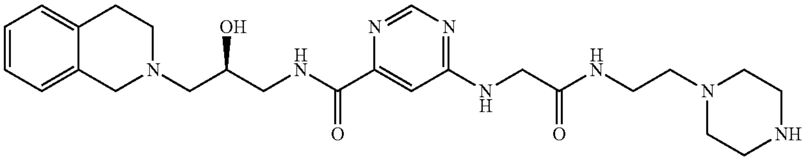 [SMILES: O=C(CNc1cc(C(=O)NC[C@H](O)CN2CCc3ccccc3C2)ncn1)NCCN1CCNCC1]

(S)-N-(3-(3,4-Dihydroisoquinolin-2(1H)-yl)-2-hydroxypropyl)-6-((2-oxo-2-((2-(piperazin-1-yl)ethyl)amino)ethyl)amino)pyrimidine-4-carboxamide To a 25-mL round bottom flask containing a solution of tert-butyl-(S)-4-(2-(2-((6-((3-(3,4-dihydroisoquinolin-2(1H)-yl)-2-hydroxypropyl)carbamoyl)pyrimidin-4-yl)amino)acetamido)ethyl)piperazine-1-carboxylate) (9.0 mg, 11.7 μmol, 1.0 eq) in THF (1 mL), a solution HCl in 1,4-dioxane (1 mL, 4.0 M) was added. The resulting mixture was stirred for 2 hours. The reaction mixture was then concentrated under reduced pressure and was used directly in the next reaction.

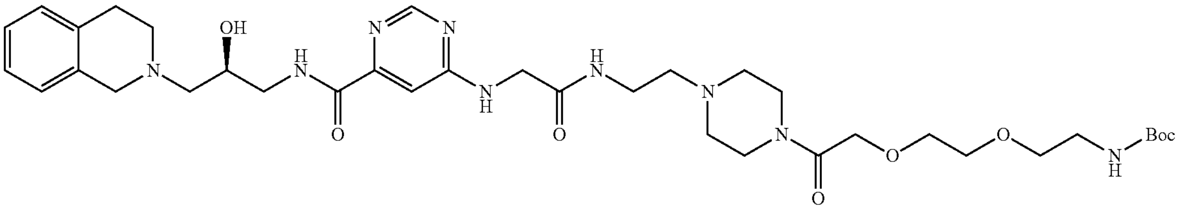 [SMILES: CC(C)(C)OC(=O)NCCOCCOCC(=O)N1CCN(CCNC(=O)CNc2cc(C(=O)NC[C@H](O)CN3CCc4ccccc4C3)ncn2)CC1]

tert-Butyl-(S)-(2-(2-(2-(4-(2-(2-((6-((3-(3,4-dihydroisoquinolin-2(1H)-yl)-2-hydroxypropyl)carbamoyl)pyrimidin-4-yl)amino)acetamido)ethyl)piperazin-1-yl)-2-oxoethoxy)ethoxy)ethyl)carbamate To a 25-mL round bottom flask containing a solution of (S)-N-(3-(3,4-dihydroisoquinolin-2(1H)-yl)-2-hydroxypropyl)-6-((2-oxo-2-((2-(piperazin-1-yl)ethyl)amino)ethyl)amino)pyrimidine-4-carboxamide (11.7 μmol, 1 eq) and 2,2-dimethyl-4-oxo-3,8,11-trioxa-5-azatridecan-13-oic acid (3.1 mg, 11.7 μmol, 1.0 eq) in DMF (100 μL), triethylamine (8.13 μL, 58.5 μmol, 5.0 eq) was added dropwise. The resulting mixture was stirred for 5 minutes before the addition of HATU (4.4 mg, 11.7 μmol, 1.0 eq). The resulting reaction mixture was stirred for 30 minutes (until the starting material was depleted as determined by MS). The reaction mixture was concentrated under a stream of nitrogen and was purified by flash chromatography (0-10% gradient MeOH:DCM) to afford tert-butyl (S)-(2-(2-(2-(4-(2-(2-((6-((3-(3,4-dihydroisoquinolin-2(1H)-yl)-2-hydroxypropyl)carbamoyl)pyrimidin-4-yl)amino)acetamido)ethyl)piperazin-1-yl)-2-oxoethoxy)ethoxy)ethyl)carbamate (7.1 mg, 9.5 μmol, 81% yield).

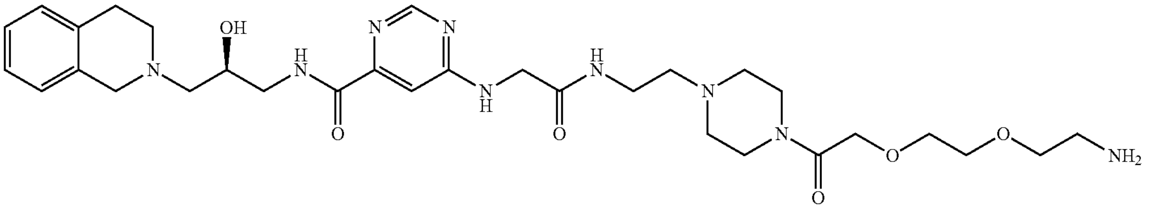 [SMILES: NCCOCCOCC(=O)N1CCN(CCNC(=O)CNc2cc(C(=O)NC[C@H](O)CN3CCc4ccccc4C3)ncn2)CC1]

(S)-6-((2-((2-(4-(2-(2-(2-aminoethoxy)ethoxy)acetyl)piperazin-1-yl)ethyl)amino)-2-oxoethyl)amino)-N-(3-(3,4-dihydroisoquinolin-2(1H)-yl)-2-hydroxypropyl)pyrimidine-4-carboxamide To a 25-mL round bottom flask containing a solution of tert-butyl (S)-(2-(2-(2-(4-(2-(2-((6-((3-(3,4-dihydroisoquinolin-2(1H)-yl)-2-hydroxypropyl)carbamoyl)pyrimidin-4-yl)amino)acetamido)ethyl)piperazin-1-yl)-2-oxoethoxy)ethoxy)ethyl)carbamate (7.1 mg, 9.5 μmol, 1.0 eq) in DCM (200 μL), TFA (25 μL) was added dropwise. The resulting mixture was stirred for 2 hours. The reaction mixture was then concentrated under reduced pressure and was used directly in the next reaction.

(7)

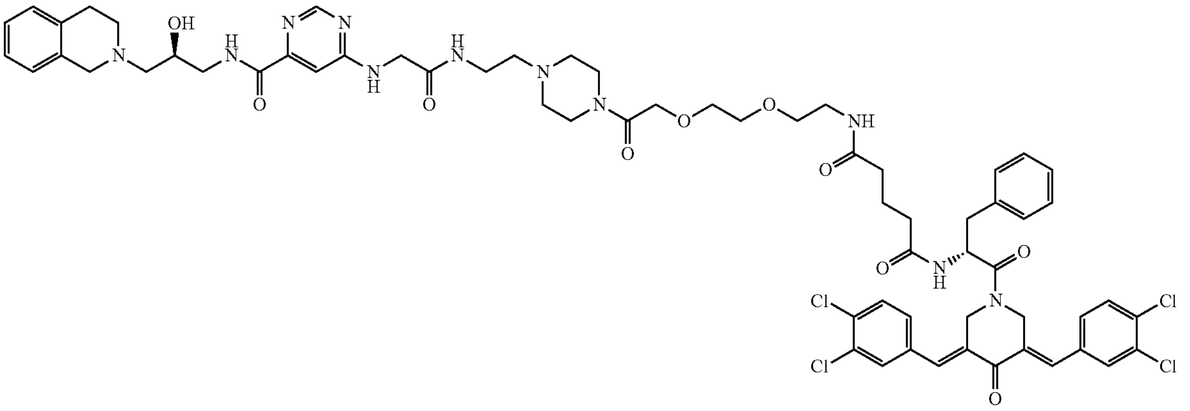

To a 25-mL round bottom flask containing a solution of (S)-6-((2-((2-(4-(2-(2-(2-aminoethoxy)ethoxy)acetyl)piperazin-1-yl)ethyl)amino)-2-oxoethyl)amino)-N-(3-(3,4-dihydroisoquinolin-2(1H)-yl)-2-hydroxypropyl)pyrimidine-4-carboxamide (11.7 μmol, 1.0 eq) and 5-(((R)-1-(3,5-bis((E)-3,4-dichlorobenzylidene)-4-oxopiperidin-1-yl)-1-oxo-3-phenylpropan-2-yl)amino)-5-oxopentanoic acid (11.7 μmol, 1.0 eq) in DMF (100 μL), triethylamine (8.13 μL, 58.5 μmol, 5.0 eq) was added dropwise. The resulting mixture was stirred for 5 minutes before the addition of HATU (4.4 mg, 11.7 μmol, 1.0 eq). The reaction was stirred for 30 minutes (until the starting material was depleted as determined by MS). The reaction mixture was then concentrated under a stream of nitrogen and was purified by flash chromatography. (0-10% gradient MeOH:DCM) to afford tert-butyl (S)-(2-(2-(2-(4-(2-(2-((6-((3-(3,4-dihydroisoquinolin-2(1H)-yl)-2-hydroxypropyl)carbamoyl)pyrimidin-4-yl)amino)acetamido)ethyl)piperazin-1-yl)-2-oxoethoxy)ethoxy)ethyl)carbamate (12.3 mg, 9.5 μmol, 81% yield).

Example 8: Synthesis of 6-((2-((7-(((S)-1-(3,5-bis((E)-3-chloro-4-methoxybenzylidene)-4-oxopiperidin-1-yl)-1-oxo-3-phenylpropan-2-yl)amino)-7-oxoheptyl)amino)-2-oxoethyl)amino)-N-((S)-3-(3,4-dihydroisoquinolin-2(1H)-yl)-2-hydroxypropyl)pyrimidine-4-carboxamide (8)

(8)

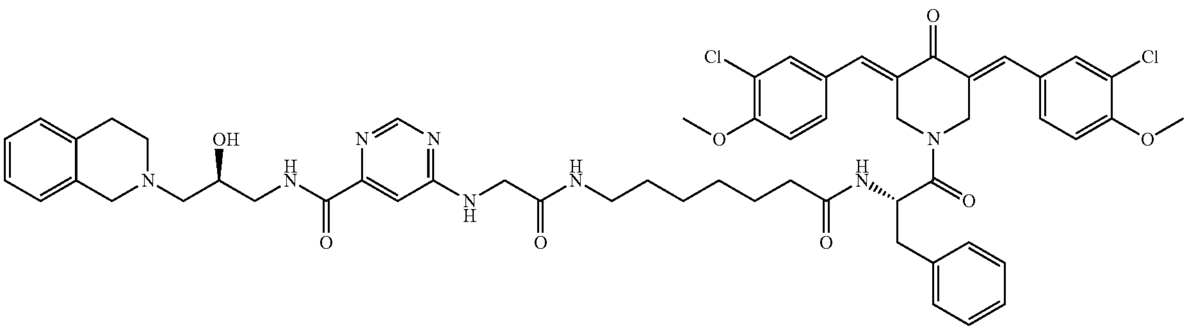

Compound 8 was prepared in an analogous manner to compound 2 in Example 2 from RA190-2 (5.0 mg, 4.8 μmol, 65% yield). The structure for RA190-2, also known as 1-(L-phenylalanyl)-3,5-bis((E)-3-chloro-4-methoxybenzylidene)piperidin-4-one, is set forth below:

(RA190-2)

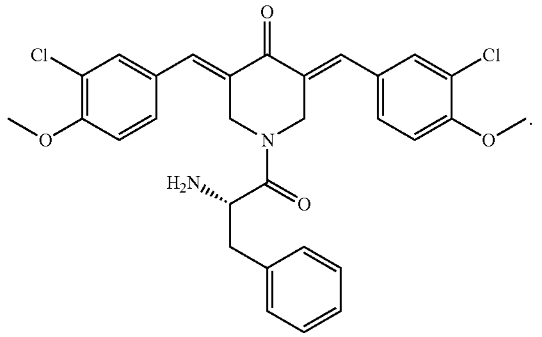

Example 9: Synthesis of 6-((2-((6-(4-((R)-2-amino-3-(3,5-bis((E)-3,4-dichlorobenzylidene)-4-oxopiperidin-1-yl)-3-oxopropyl)phenoxy)hexyl)amino)-2-oxoethyl)amino)-N-((S)-3-(3,4-dihydroisoquinolin-2(1H)-yl)-2-hydroxypropyl)pyrimidine-4-carboxamide (9)

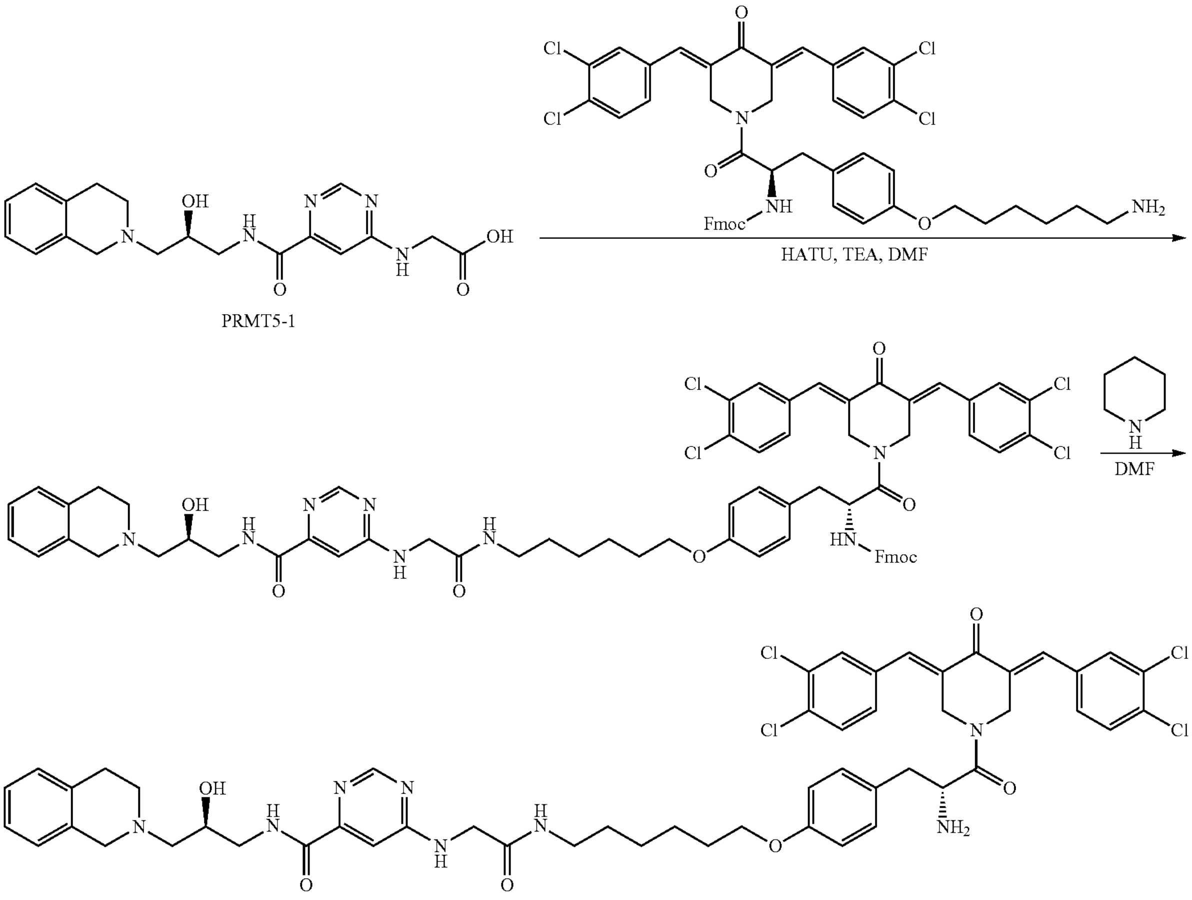

PRMT5-1

9

-continued

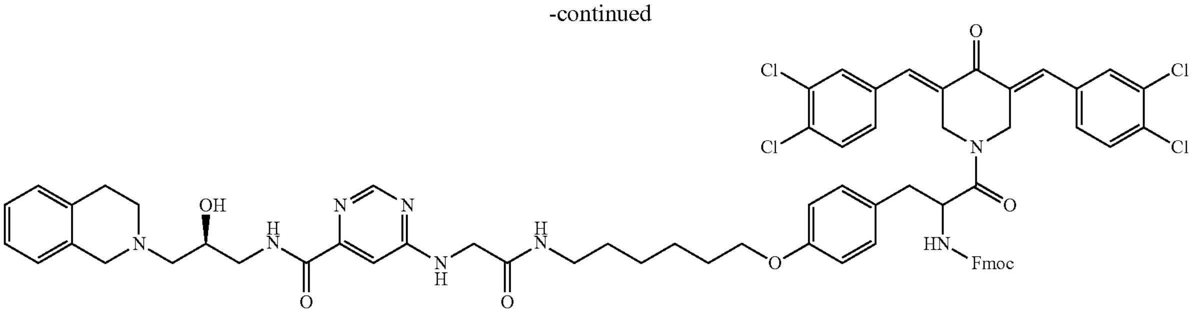

(9H-fluoren-9-yl)methyl (1-(3,5-bis((E)-3,4-dichlorobenzylidene)-4-oxopiperidin-1-yl)-3-(4-((6-(2-((6-(((S)-3-(3,4-dihydroisoquinolin-2(1H)-yl)-2-hydroxypropyl)carbamoyl)pyrimidin-4-yl)amino)acetamido)hexyl)oxy)phenyl)-1-oxopropan-2-yl)carbamate To a 25-mL round bottom flask containing a solution of PRMT5-1 (3.7 mg, 4.5 μmol, 1.0 eq) and (9H-fluoren-9-yl)methyl (3-(4-((6-aminohexyl)oxy)phenyl)-1-(3,5-bis((E)-3,4-dichlorobenzylidene)-4-oxopiperidin-1-yl)-1-oxopropan-2-yl)carbamate (8.53 mg, 4.5 μmol, 1.0 eq) in DMF (50 μL), triethylamine (6.6 μL, 22.5 μmol, 5.0 eq) was added dropwise. The resulting mixture was stirred for 5 minutes before the addition of HATU (3.6 mg, 10.9 μmol, 1.0 eq). The resulting reaction mixture was stirred for 30 minutes (until the starting material was depleted as determined by MS). The reaction mixture was concentrated under a stream of nitrogen and was purified by flash chromatography (0-10% gradient MeOH:DCM) to afford (9H-fluoren-9-yl)methyl (1-(3,5-bis((E)-3,4-dichlorobenzylidene)-4-oxopiperidin-1-yl)-3-(4-((6-(2-((6-(((S)-3-(3,4-dihydroisoquinolin-2(1H)-yl)-2-hydroxypropyl)carbamoyl)pyrimidin-4-yl)amino)acetamido)hexyl)oxy)phenyl)-1-oxopropan-2-yl)carbamate (3.4 mg, 3.1 μmol, 69%).

(9)

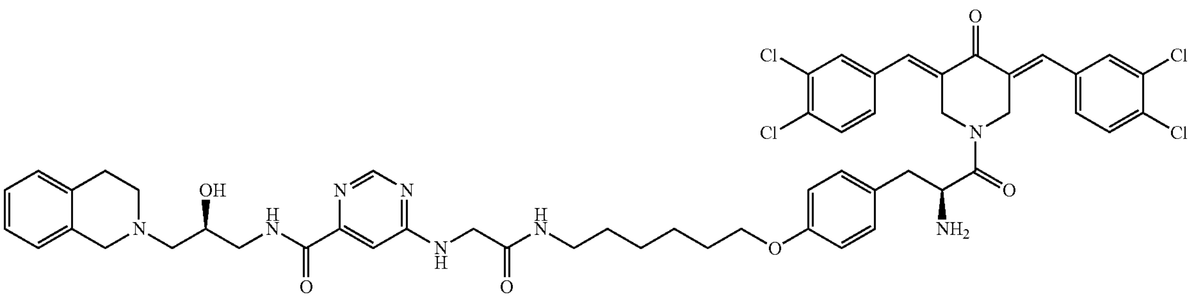

To a 25-mL round bottom flask containing a solution (9H-fluoren-9-yl)methyl (1-(3,5-bis((E)-3,4-dichlorobenzylidene)-4-oxopiperidin-1-yl)-3-(4-((6-(2-((6-(((S)-3-(3,4-dihydroisoquinolin-2(1H)-yl)-2-hydroxypropyl)carbamoyl)pyrimidin-4-yl)amino)acetamido)hexyl)oxy)phenyl)-1-oxopropan-2-yl)carbamate (7.1 mg, 9.5 μmol, 1.0 eq) in DMF (600 μL), piperidine (120 μL) was added. The reaction mixture was stirred for 30 minutes. The reaction mixture was then concentrated under reduced pressure and was purified by prep-HPLC to afford compound 9.

Example 10: Synthesis of 6-((1-((1-(3,5-bis((E)-3,4-dichlorobenzylidene)-4-oxopiperidin-1-yl)-1-oxo-3-phenylpropan-2-yl)glycyl)azetidin-3-yl)amino)-N-((S)-3-(3,4-dihydroisoquinolin-2(1H)-yl)-2-hydroxypropyl)pyrimidine-4-carboxamide (10)

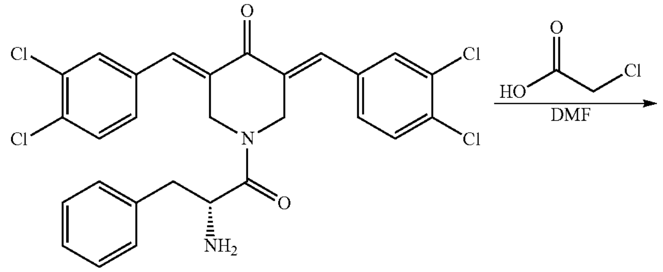

RA190

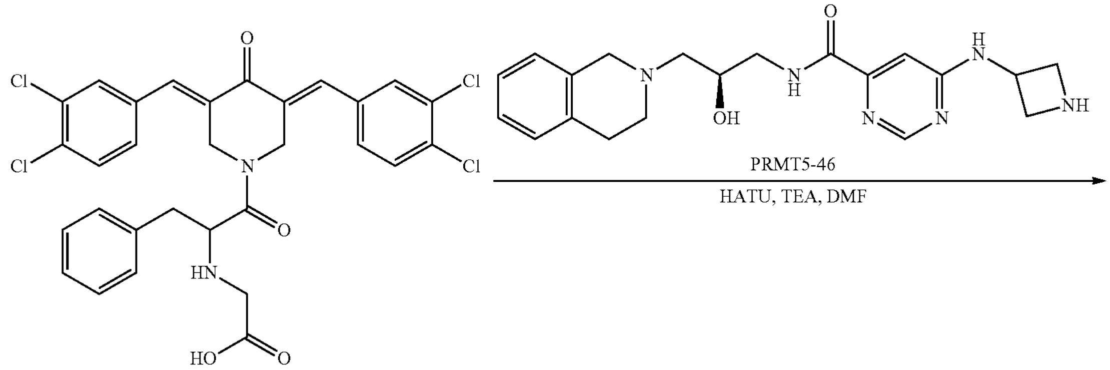

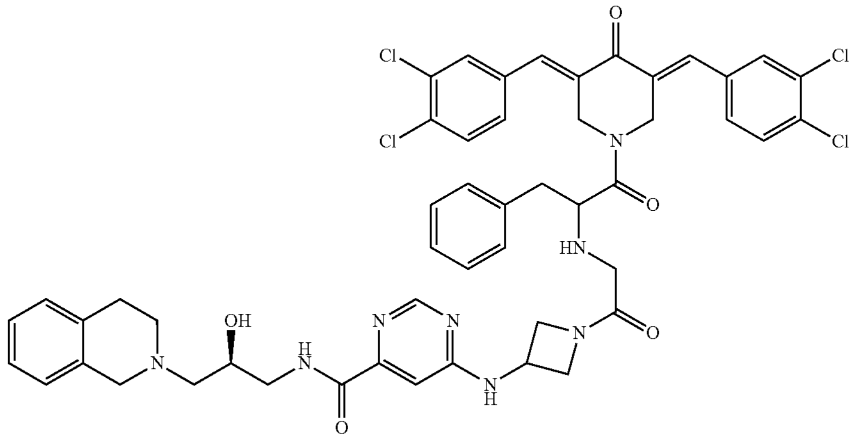

10

-continued

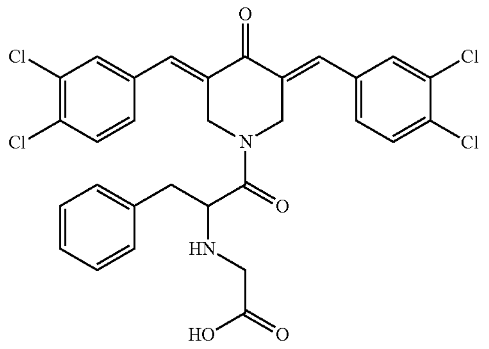

(1-(3,5-bis((E)-3,4-dichlorobenzylidene)-4-oxopiperidin-1-yl)-1-oxo-3-phenylpropan-2-yl)glycine To a 25-mL round bottom flask containing a solution of RA190 (10 mg, 17.8 μmol, 1.0 eq) and chloroacetic acid (3.3 mg, 35.7 μmol, 2.0 eq) in DMF (100 μL), triethylamine (12.4 μL, 89.2 μmol, 5.0 eq) was added. The reaction mixture was heated to 60° C. and stirred for 20 hours. The reaction mixture was concentrated under a stream of nitrogen and purified by flash chromatography (0-10% gradient MeOH:DCM) to afford (1-(3,5-bis((E)-3,4-dichlorobenzylidene)-4-oxopiperidin-1-yl)-1-oxo-3-phenylpropan-2-yl)glycine (10.64 mg, 17.2 μmol, 96% yield).

(10)

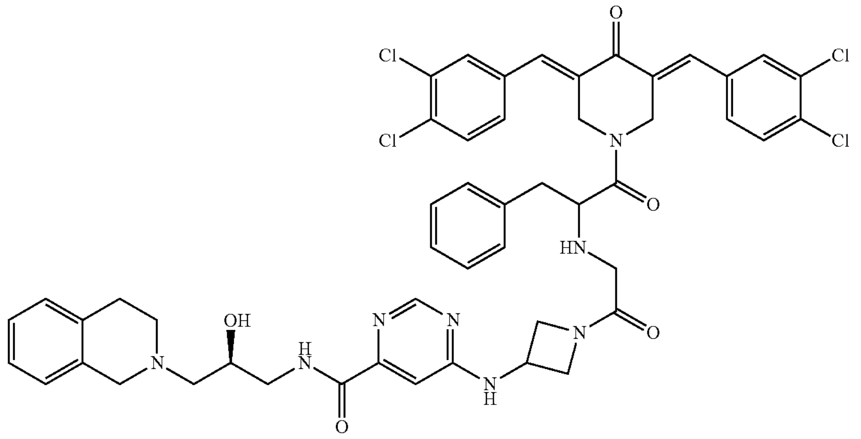

To a 25-mL round bottom flask containing a solution of PRMT5-46 (3.0 mg, 8.1 μmol, 1.0 eq) and (1-(3,5-bis((E)-3,4-dichlorobenzylidene)-4-oxopiperidin-1-yl)-1-oxo-3-phenylpropan-2-yl)glycine (5.0 mg, 8.1 μmol, 1.0 eq) in DMF (100 μL), triethylamine (7.0 μL, 40.5 μmol, 5 eq) was added dropwise. The reaction was stirred for 5 minutes before the addition of HATU (3.1 mg, 8.1 μmol, 1.0 eq). The reaction mixture was directly purified by prep-HPLC to afford compound 10. (1.1 mg, 1.1 μmol, 13.8% yield).

Example 11: Synthesis of 6-((2-((2-(4-((1-(3,5-bis((E)-3,4-dichlorobenzylidene)-4-oxopiperidin-1-yl)-1-oxo-3-phenylpropan-2-yl)glycyl)piperazin-1-yl)ethyl)amino)-2-oxoethyl)amino)-N-((S)-3-(3,4-dihydroisoquinolin-2(1H)-yl)-2-hydroxypropyl)pyrimidine-4-carboxamide (11)

(11)

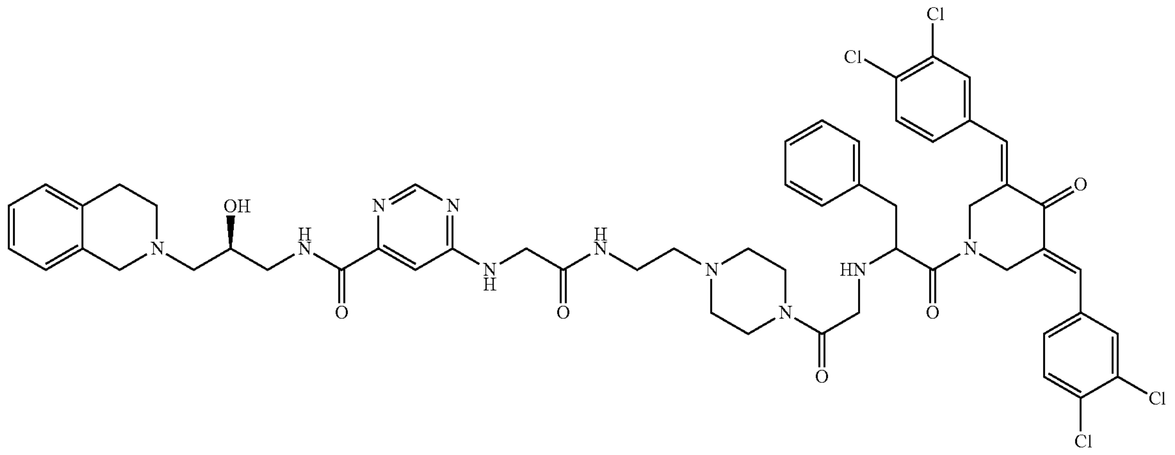

To a 25-mL round bottom flask containing a solution (S)-N-(3-(3,4-dihydroisoquinolin-2(1H)-yl)-2-hydroxypropyl)-6-((2-oxo-2-((2-(piperazin-1-yl)ethyl)amino)ethyl)amino)pyrimidine-4-carboxamide (4.3 mg, 8.1 μmol, 1.0 eq) and (1-(3,5-bis((E)-3,4-dichlorobenzylidene)-4-oxopiperidin-1-yl)-1-oxo-3-phenylpropan-2-yl)glycine (5.0 mg, 8.1 μmol, 1.0 eq) in DMF (100 μL), triethylamine (7.0 μL, 40 μmol, 5.0 eq) was added dropwise. The resulting mixture was stirred for 5 minutes before the addition of HATU (3.1 mg, 8.1 μmol, 1.0 eq). The resulting reaction mixture was directly purified by prep-HPLC to afford compound 11. (0.88 mg, 0.80 μmol, 9.8% yield).

Example 12: Synthesis of 6-((2-((7-(((S)-1-(3,5-bis((E)-4-nitrobenzylidene)-4-oxopiperidin-1-yl)-1-oxo-3-phenylpropan-2-yl)amino)-7-oxoheptyl)amino)-2-oxoethyl)amino)-N-((S)-3-(3,4-dihydroisoquinolin-2(1H)-yl)-2-hydroxypropyl)pyrimidine-4-carboxamide (13)

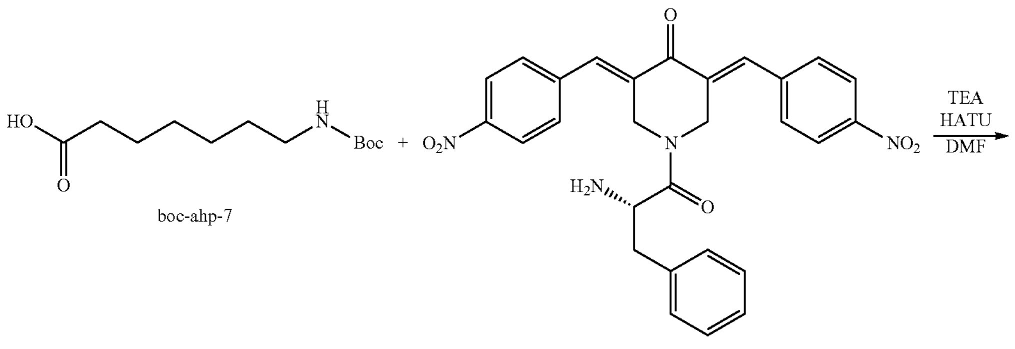

boc-ahp-7

RA183

-continued
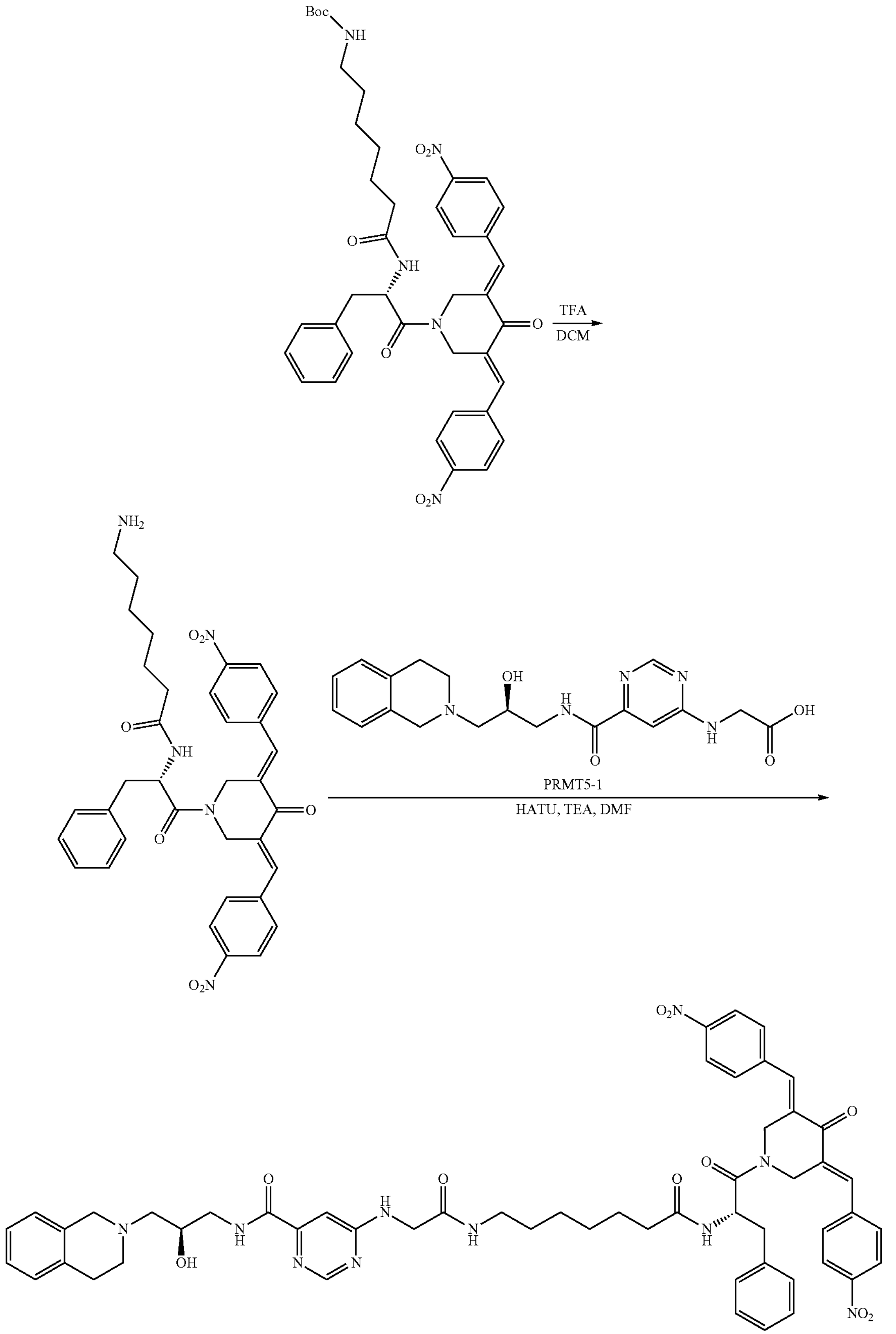

-continued

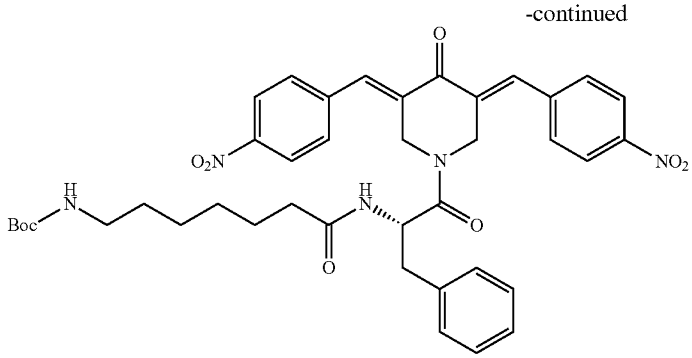

tert-Butyl(7-(((S)-1-(3,5-bis((E)-4-nitrobenzylidene)-4-oxopiperidin-1-yl)-1-oxo-3-phenylpropan-2-yl)amino)-7-oxoheptyl)carbamate To a 25-mL round bottom flask containing a solution of RA183 (50.0 mg, 97.6 μmol, 1.0 eq) and boc-ahp-7 (28.7 mg, 117.1 μmol, 1.2 eq) in DMF (300 μL), triethylamine (67.9 μL, 488.0 μmol, 5 eq) was added dropwise. The reaction mixture was stirred for 5 minutes before the addition of HATU (37.1 mg, 97.6 μmol, 1.0 eq). The resulting reaction mixture was stirred for 30 minutes (until the starting material was depleted as determined by MS). The reaction mixture was purified by prep-HPLC to afford tert-butyl (7-(((S)-1-(3,5-bis((E)-4-nitrobenzylidene)-4-oxopiperidin-1-yl)-1-oxo-3-phenylpropan-2-yl)amino)-7-oxoheptyl)carbamate (55.2 mg, 43.2 μmol, 76.4%).

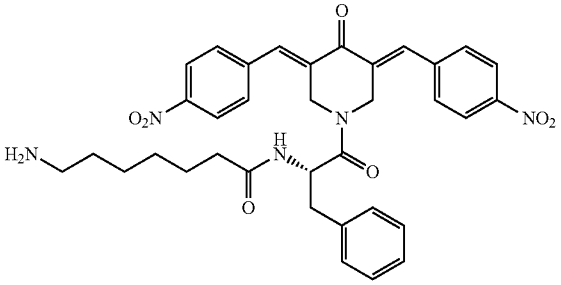 [SMILES: NCCCCCCC(=O)N[C@@H](Cc1ccccc1)C(=O)N1C/C(=C\c2ccc([N+](=O)[O-])cc2)C(=O)/C(=C/c2ccc([N+](=O)[O-])cc2)C1]

7-amino-N-((S)-1-(3,5-bis((E)-4-nitrobenzylidene)-4-oxopiperidin-1-yl)-1-oxo-3-phenylpropan-2-yl)heptanamide To a 25-mL round bottom flask containing a solution of tert-butyl (7-(((S)-1-(3,5-bis((E)-4-nitrobenzylidene)-4-oxopiperidin-1-yl)-1-oxo-3-phenylpropan-2-yl)amino)-7-oxoheptyl)carbamate (55.2 mg, 43.2 μmol, 1 eq) in DCM (4 mL) at 0° C., TFA (1 mL) was added dropwise, and the reaction mixture was stirred for 2 hours. The reaction mixture was then diluted with water and was lipolyzed to afford 7-amino-N-((S)-1-(3,5-bis((E)-4-nitrobenzylidene)-4-oxopiperidin-1-yl)-1-oxo-3-phenylpropan-2-yl)heptanamide, which was used directly in the next reaction.

(13)

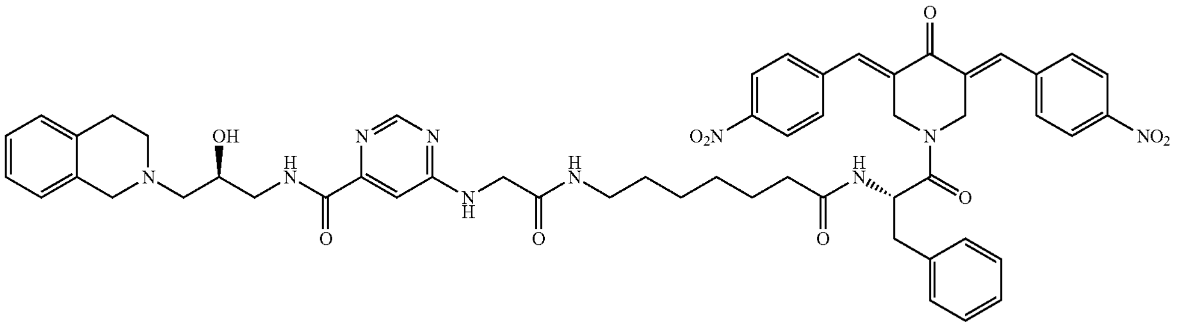

To a 25-mL round bottom flask containing a solution of PRMT5-1 (8.3 mg, 21.6 μmol, 1.0 eq) and 7-amino-N-((S)-1-(3,5-bis((E)-3-chloro-4-methoxybenzylidene)-4-oxopiperidin-1-yl)-1-oxo-3-phenylpropan-2-yl)heptanamide (21.6 μmol, 1.0 eq) in DMF (300 μL), triethylamine (15.0 μL, 108.1 μmol, 5 eq) was added dropwise. The reaction mixture was stirred for 5 minutes before the addition of HATU (9.2 mg, 24.1 μmol, 1.0 eq). The resulting reaction mixture was stirred for 30 minutes (until the starting material was depleted as determined by MS). The material was directly purified by Prep-HPLC to afford compound 13 (0.78 mg, 0.77 μmol, 3.6% yield).

Example 13: Synthesis of 6-((1-(5-(((S)-1-(3,5-bis((E)-3,4-dichlorobenzylidene)-4-oxopiperidin-1-yl)-1-oxo-3-phenylpropan-2-yl)amino)-5-oxopentanoyl)piperidin-4-yl)amino)-N-((R)-3-(3,4-dihydroisoquinolin-2(1H)-yl)-2-hydroxypropyl)pyrimidine-4-carboxamide (14)

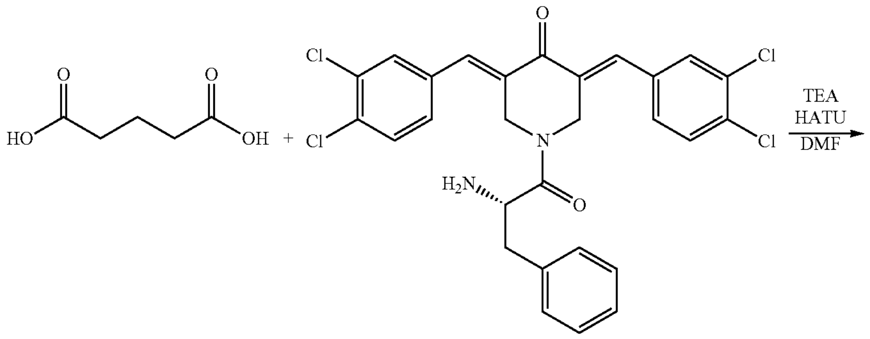

RA190

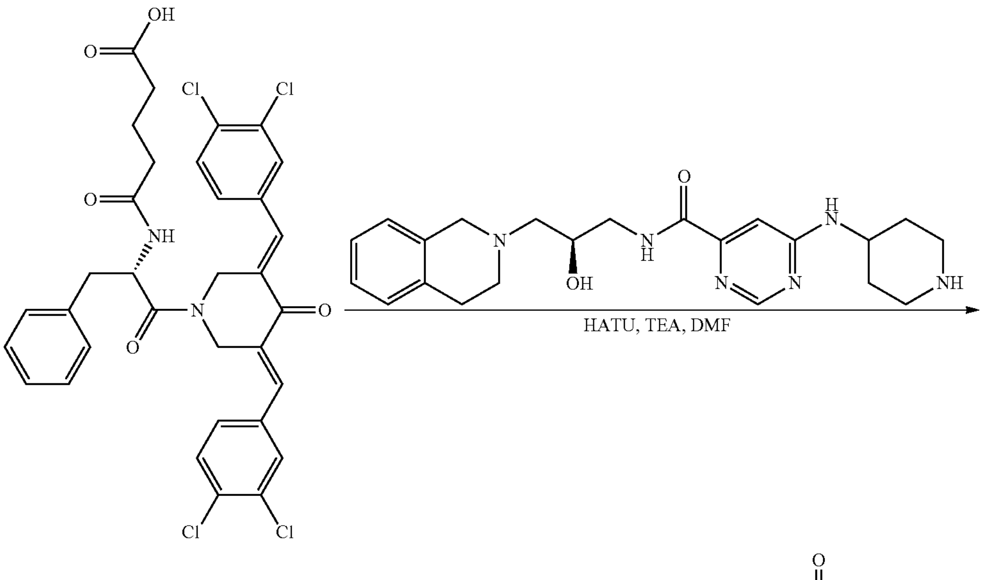

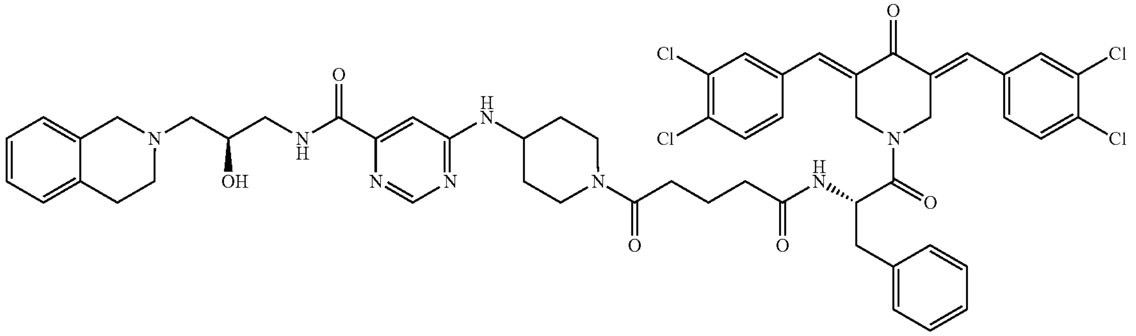

14

-continued

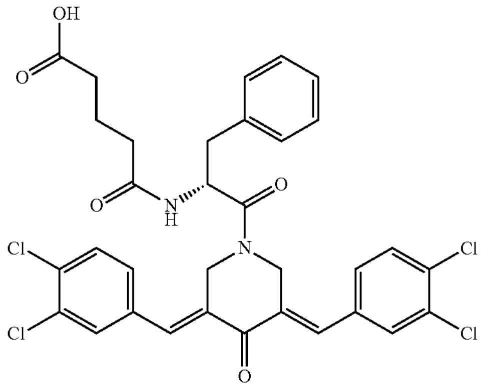

5-(((R)-1-(3,5-bis((E)-3,4-dichlorobenzylidene)-4-oxopiperidin-1-yl)-1-oxo-3-phenylpropan-2-yl)amino)-5-oxopentanoic Acid To a 25-mL round bottom flask containing a solution of RA190 (30 mg, 53.8 μmol, 1 eq) and glutaric anhydride (6.15 mg, 80.7 μmol, 1.5 eq) in MeCN (400 μL), triethylamine (29.9 μL, 215.2 μmol, 4 eq) was added. The resulting mixture was stirred for 3 hours and was concentrated under reduced pressure to afford. The reaction mixture was then diluted with water and was lipolyzed to afford 5-(((R)-1-(3,5-bis((E)-3,4-dichlorobenzylidene)-4-oxopiperidin-1-yl)-1-oxo-3-phenylpropan-2-yl)amino)-5-oxopentanoic acid, which was directly used in the next step.

(14)

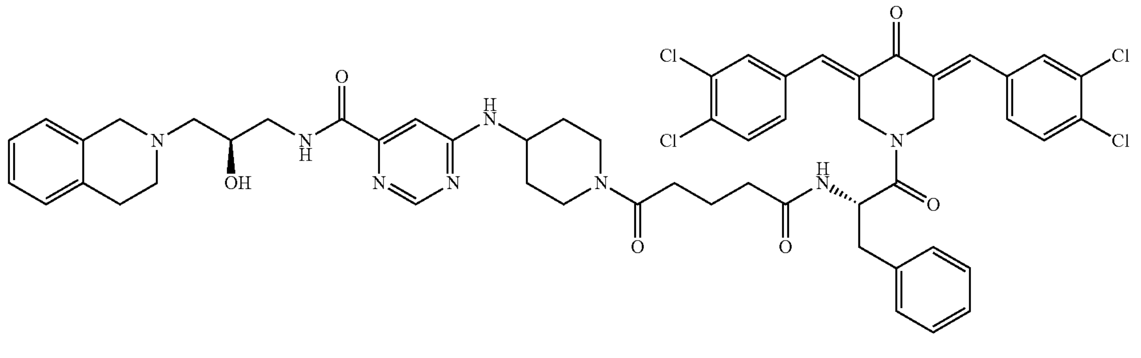

To a 25-mL round bottom flask containing a solution of (R)—N-(3-(3,4-dihydroisoquinolin-2(1H)-yl)-2-hydroxy-propyl)-6-(piperidin-4-ylamino)pyrimidine-4-carboxamide (3.66 mg, 8.9 μmol, 1.0 eq) and 5-(((R)-1-(3,5-bis((E)-3,4-dichlorobenzylidene)-4-oxopiperidin-1-yl)-1-oxo-3-phenyl-propan-2-yl)amino)-5-oxopentanoic acid (6.0 mg, 8.9 μmol, 1 eq) in DMF (100 μL), triethylamine (6.2 μL, 44.6 μmol, 5 eq) was added. The resulting mixture was stirred for 5 minutes before the addition of HATU (3.4 mg, 8.9 μmol, 1 eq). The reaction mixture was stirred for 1 hour (until completion). The crude product was then diluted to 300 μL total volume with DMF and purified by Prep-HPLC purified to afford compound 14 (0.84 mg, 0.79 μmol, 8.9% yield).

Example 14: Biochemical Profiling: PRMT5 Activity Inhibition in HEK 293 WT Cells with Inventive Bifunctional Compounds PMRT5 inhibition in HEK 293 WT cells was determined by AlphaLISA® assay (PerkinElmer®) according to manufacturer's instructions. The biotinylated Histone 4 Arginine 4 histone tail was incubated with PRMT5/MEP50 and inventive bifunctional compounds 1-9, cereblon-based bifunctional compound PRMT5-58, PRMT5 inhibitors EPZ15666 and LLY-283 and RPN13 inhibitor RA190. Then the H4R3symetric Me2 antibody coated beads together with streptavidin beads were incubated together. Assays were processed by EnVision® multimode plate reader (PerkinElmer®).

The structures of inhibitors EPZ15666, LL283 and RA190 and bifunctional compound PRMT5-58 are set forth below:

(EPZ15666)

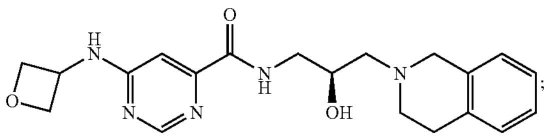

(LLY-283)

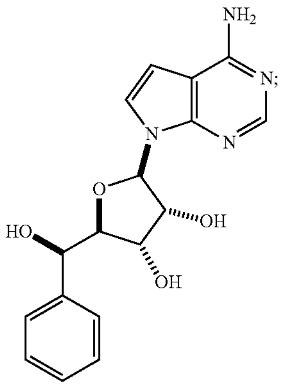

(RA190)

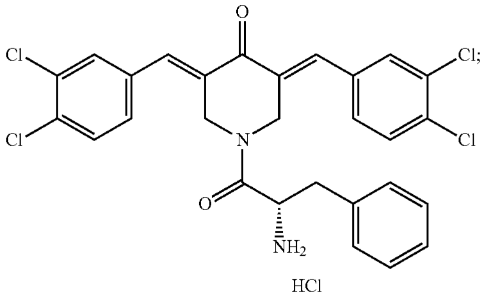

and (PRMT5-58)

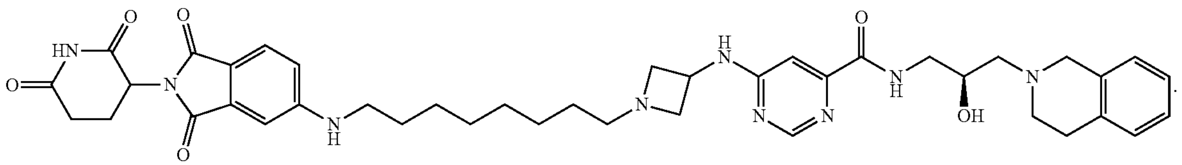

Figure 2A:
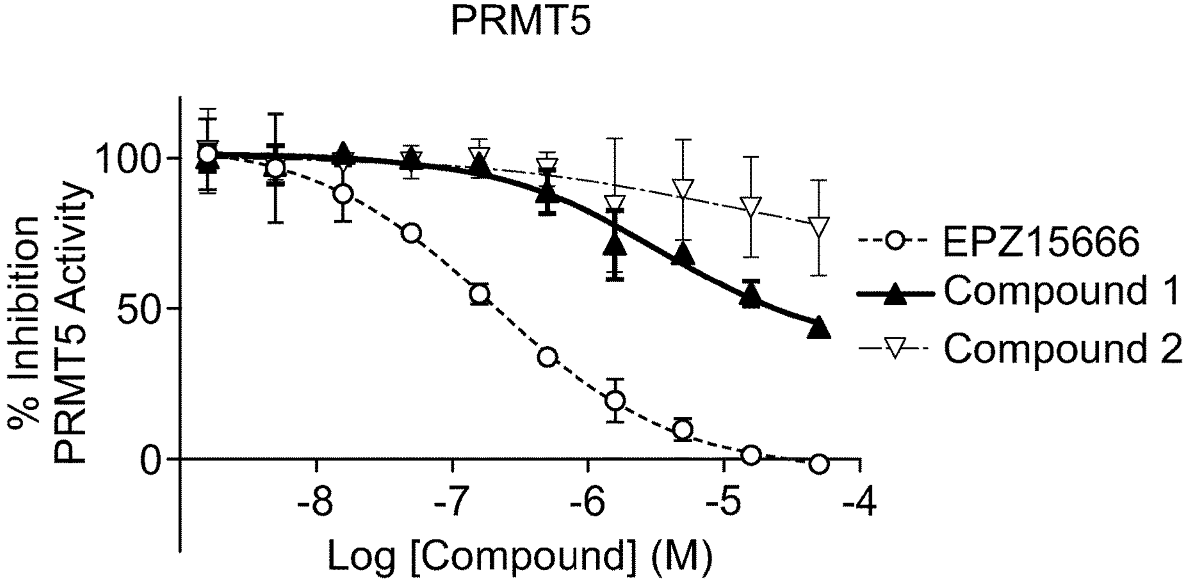
FIG. 2A is a plot of percent arginine methyltransferase 5 (PRMT5) activity inhibition versus log (concentration (M)) of inventive bifunctional compounds 1 and 2, and PRMT5 inhibitor EPZ15666.
Figure 2B:
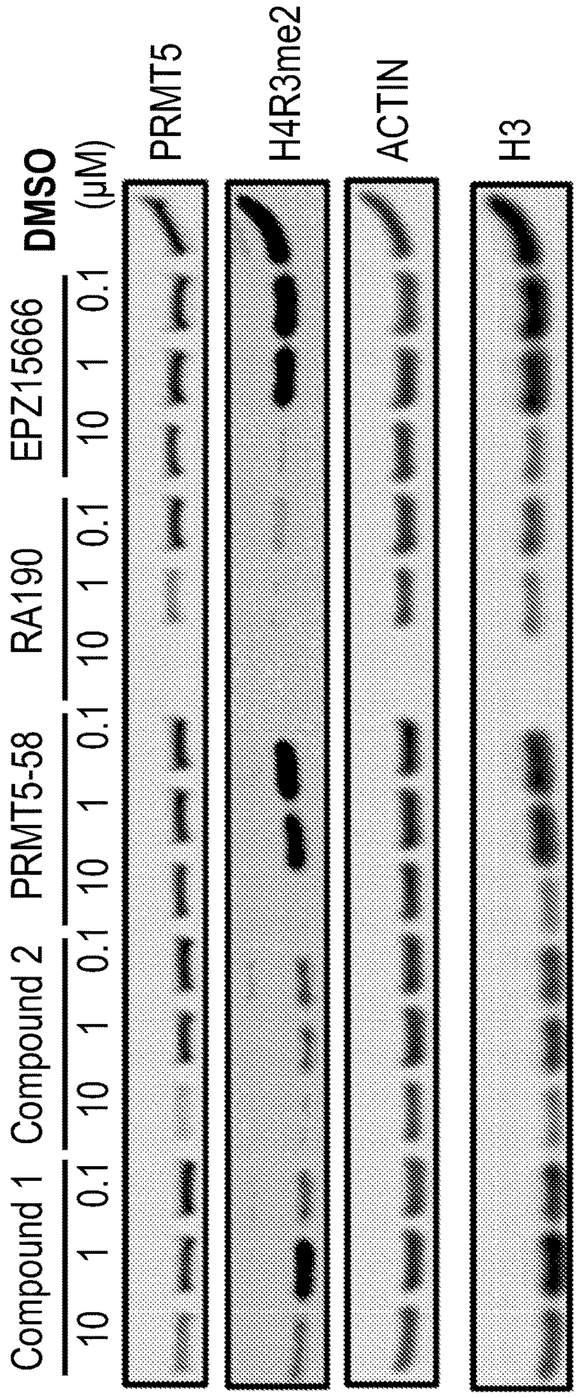
FIG. 2B is an image showing an immunoblot analysis of HEK 293T WT cells treated with different concentrations (μM) of inventive bifunctional compounds 1 and 2, bifunctional compound PRMT5-58 (positive control), PRMT5 inhibitor EPZ15666 and RPN13 inhibitor RA190 for 24 hours.
Figure 2C:
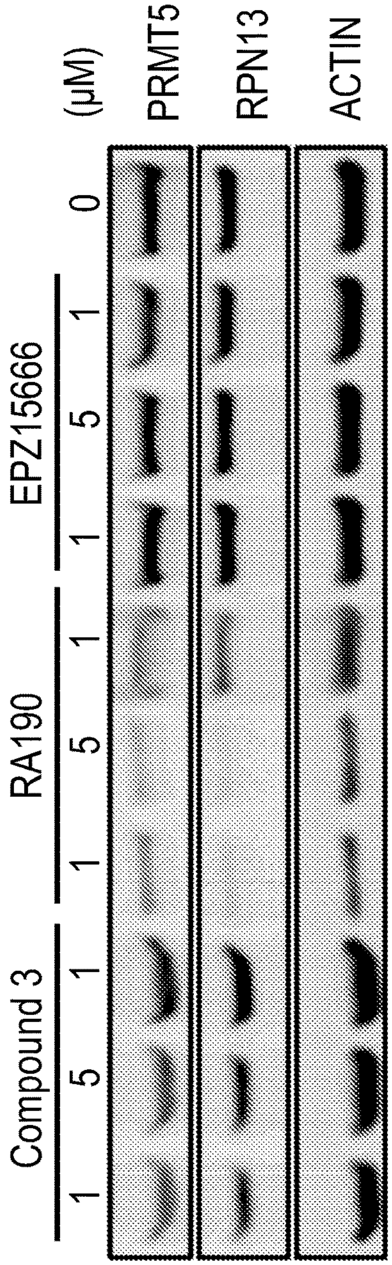
FIG. 2C is an image showing an immunoblot analysis of HEK 293T WT cells treated with different concentrations (μM) of inventive bifunctional compound 3, PRMT5 inhibitor EPZ15666 and RPN13 inhibitor RA190 for 24 hours.
Figure 2D:
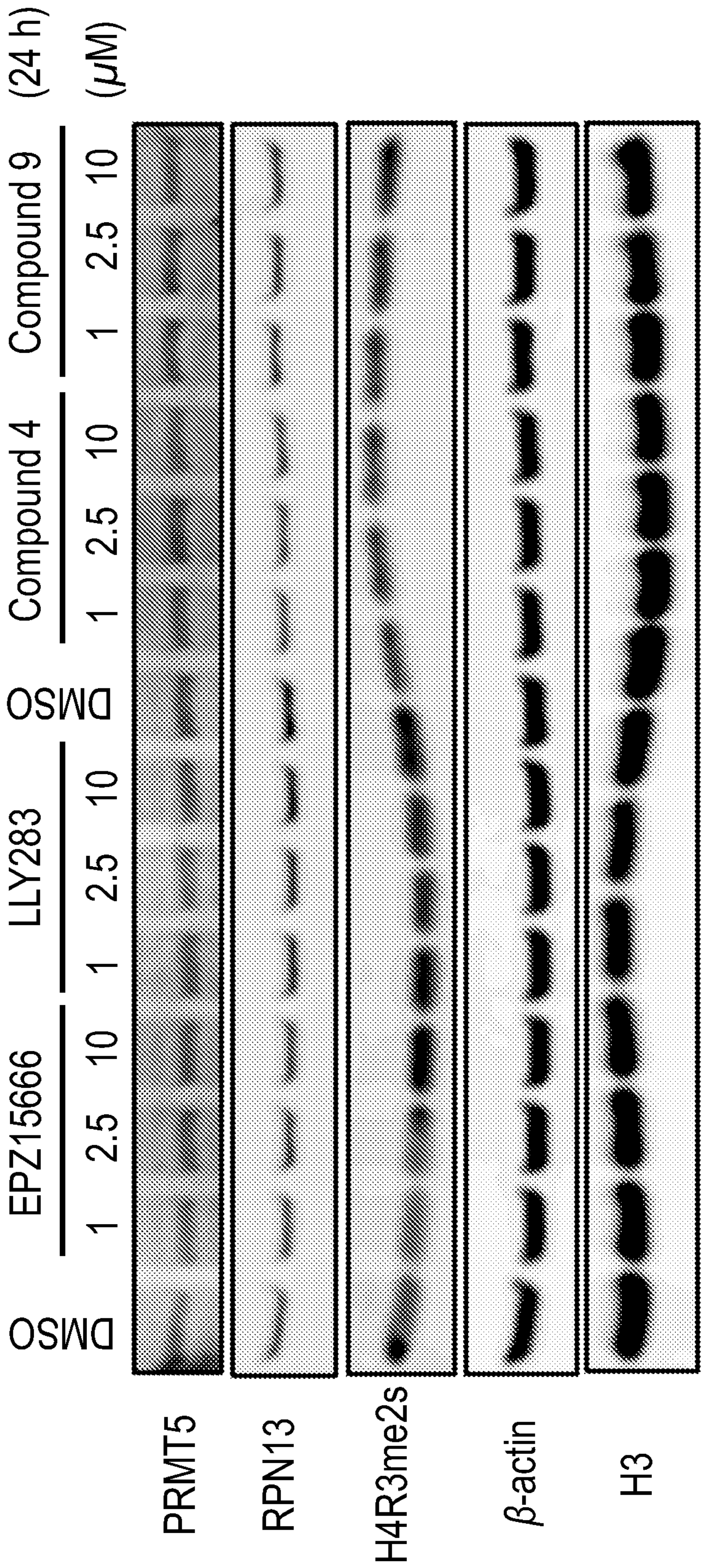
FIG. 2D is an image showing an immunoblot analysis of HEK 293T WT cells treated with different concentrations (μM) of inventive bifunctional compounds 4 and 9, PRMT5 inhibitors EPZ15666 and LLY-283 for 24 hours.
Figure 2E:
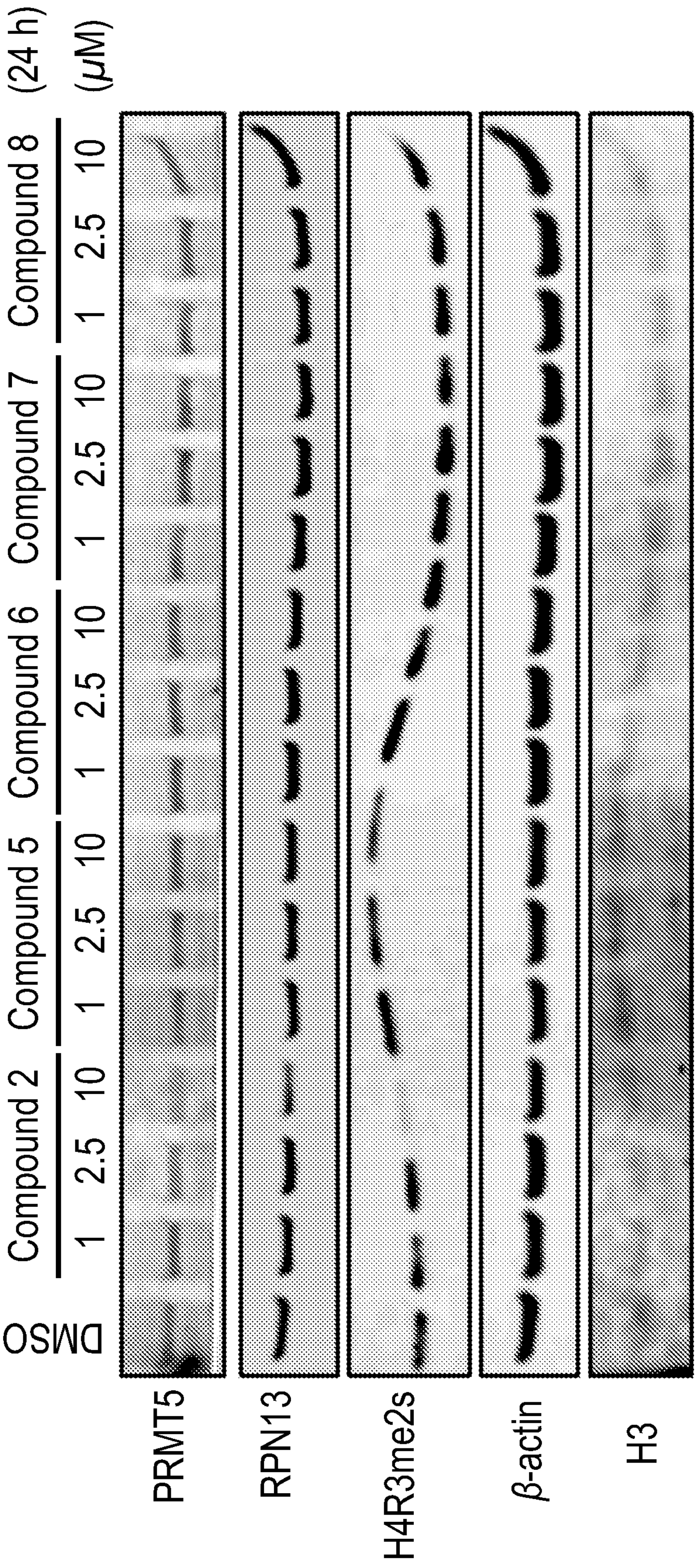
FIG. 2E is an image showing an immunoblot analysis of HEK 293T WT cells treated with different concentrations (μM) of inventive bifunctional compounds 2 and 5-8 for 24 hours.
Figure 2F:
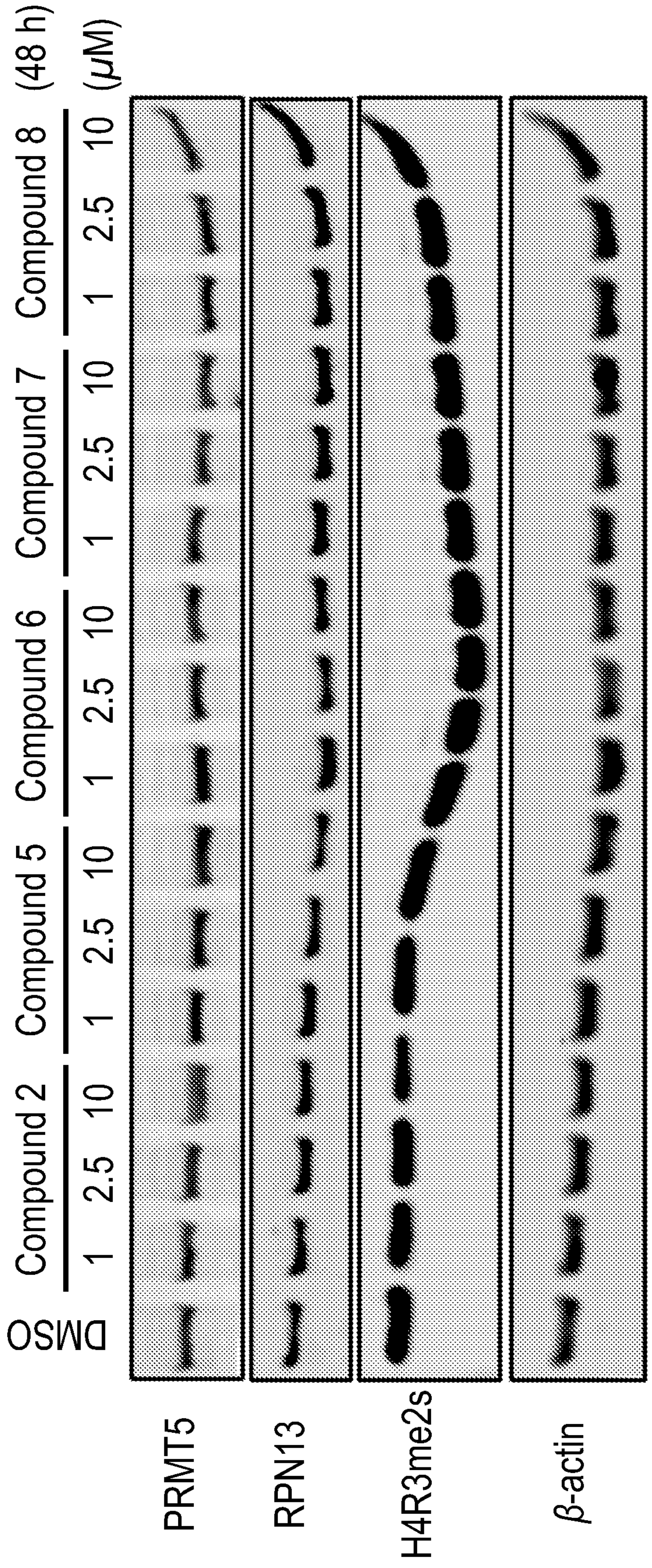
FIG. 2F is an image showing an immunoblot analysis of HEK 293T WT cells treated with different concentrations (μM) of inventive bifunctional compounds 2 and 5-8 for 48 hours.

The results illustrated in FIG. 2A show that the inventive bifunctional compounds 1 and 2 successfully inhibited PRMT5 function.

The results illustrated in FIG. 2B-FIG. 2F show that inventive bifunctional compounds 1-9 reduced PRMT5 protein level in 293T cells upon treatment with different concentrations of the bifunctional compounds at 24 or 48 hours.

Example 15: Cell-Proliferation Assay in A427 and H661 Cells

Inventive bifunctional compounds 1 and 2 were tested in the A427 (anon-small cell lung cancer (NSCLC) cell line) and H661(human lung large cell carcinoma) cells. CellTiter-Glo® 2.0 Cell Viability Assay (Promega™) was used to measure cell growth (proliferation) inhibition and to report the ATP level reduction in cells after treatment with the bifunctional compounds.

Figure 3A:
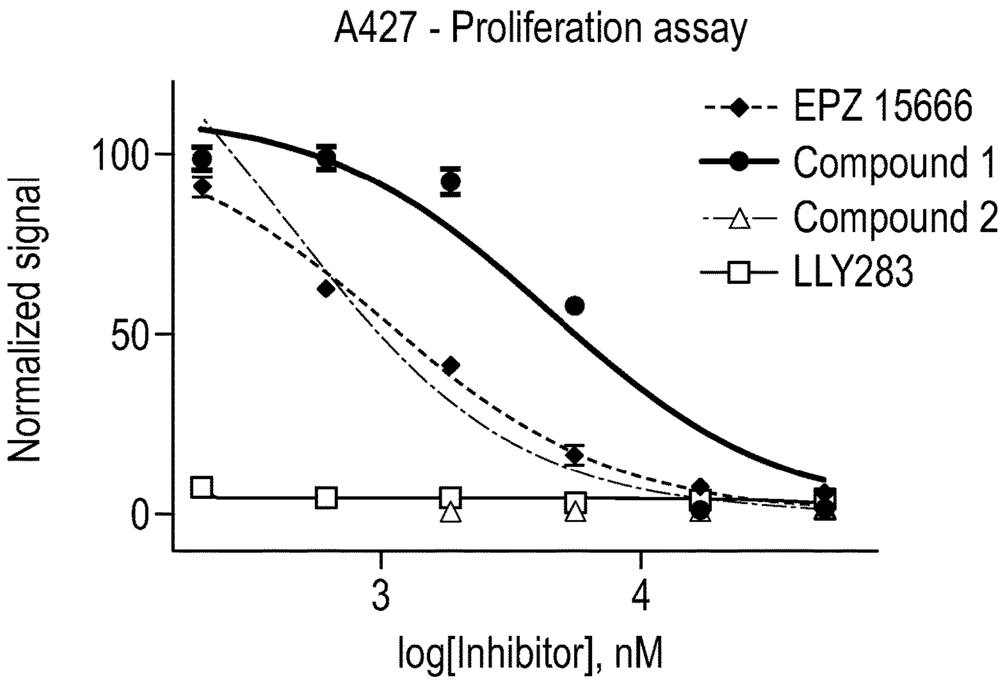
FIG. 3A is a plot of proliferation in A427 cells versus log (concentration (nM)) of inventive compounds 1 and 2, and PRMT5 inhibitors EPZ15666 and LLY-283.

The results illustrated in FIG. 3A show that inventive bifunctional compounds 1 and 2 effectively inhibited growth of A427 cells.

Figure 3B:
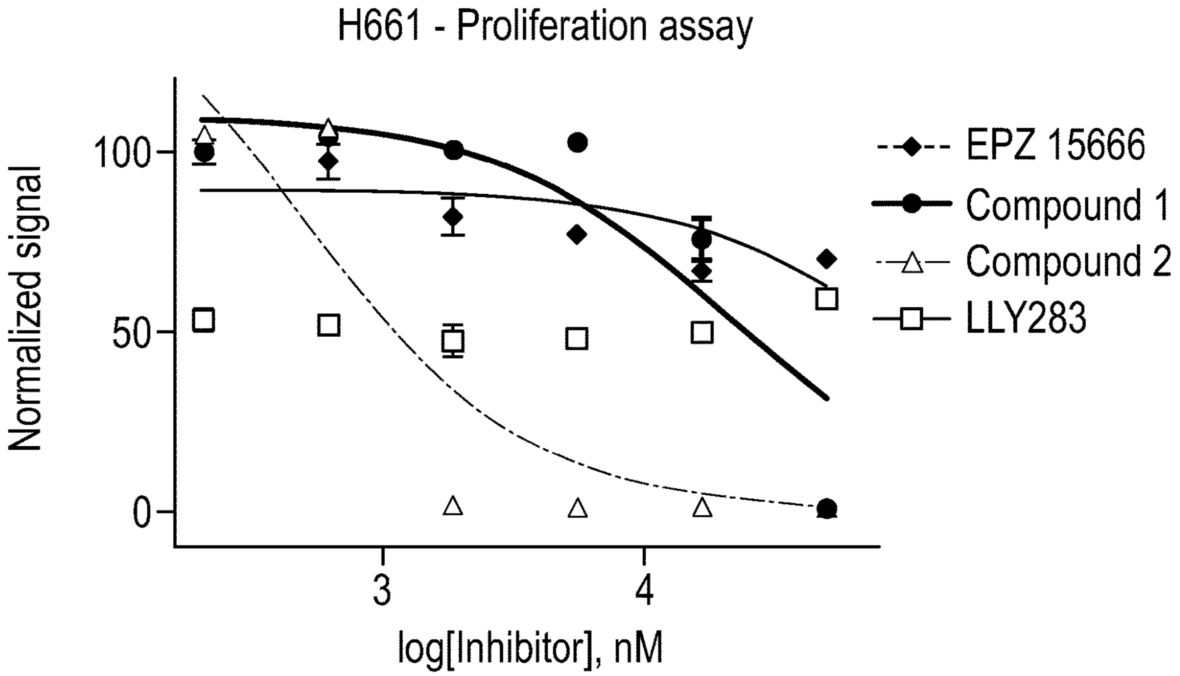
FIG. 3B is a plot of proliferation in H661 cells versus log (concentration (nM)) of inventive compounds 1 and 2, and PRMT5 inhibitors EPZ15666 and LLY-283.

The results illustrated in FIG. 3B show that inventive bifunctional compounds 1 and 2 effectively inhibited growth in H661 cells. Compound 2 showed improved inhibition of cell growth compared to PRMT5 inhibitors EPZ15666 and LLY283.

Example 16: Immunoblot Analysis of HL60 (Leukemia) Cells Treated with Different Concentrations (M) of Inventive Bifunctional Compound 13 and 14 at 24 Hours Protein lysates were subjected to immunoblot analysis using anti-Rpn13, anti-betaActin, anti-H4R3Me2s, anti-H3, anti-RPN1 and anti-RPN10.

Figure 4A:
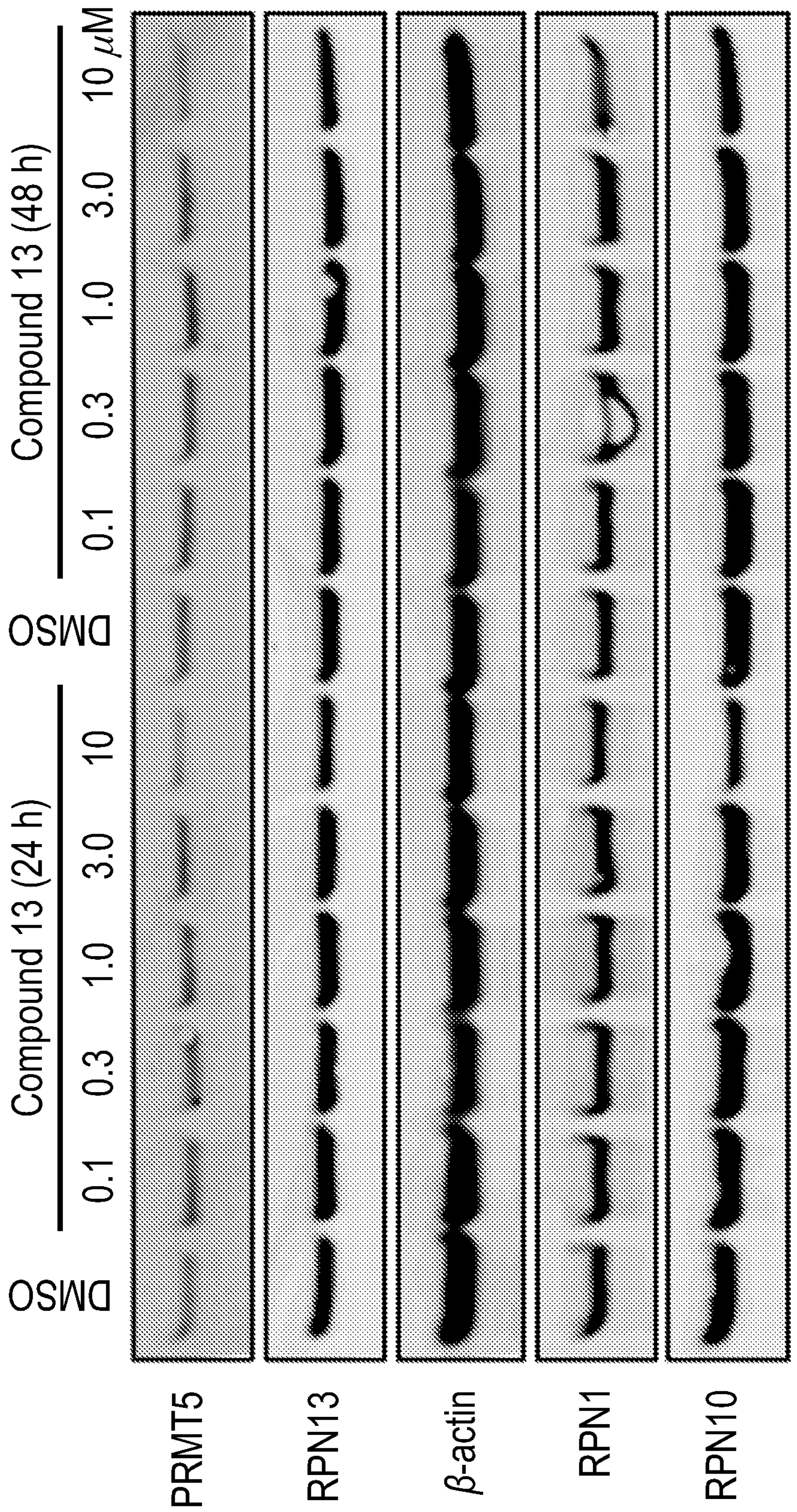
FIG. 4A is an image showing an immunoblot analysis of HL60 cells treated with different concentrations (μM) of inventive bifunctional compound 13 for 24 hours and 48 hours.
Figure 4B:
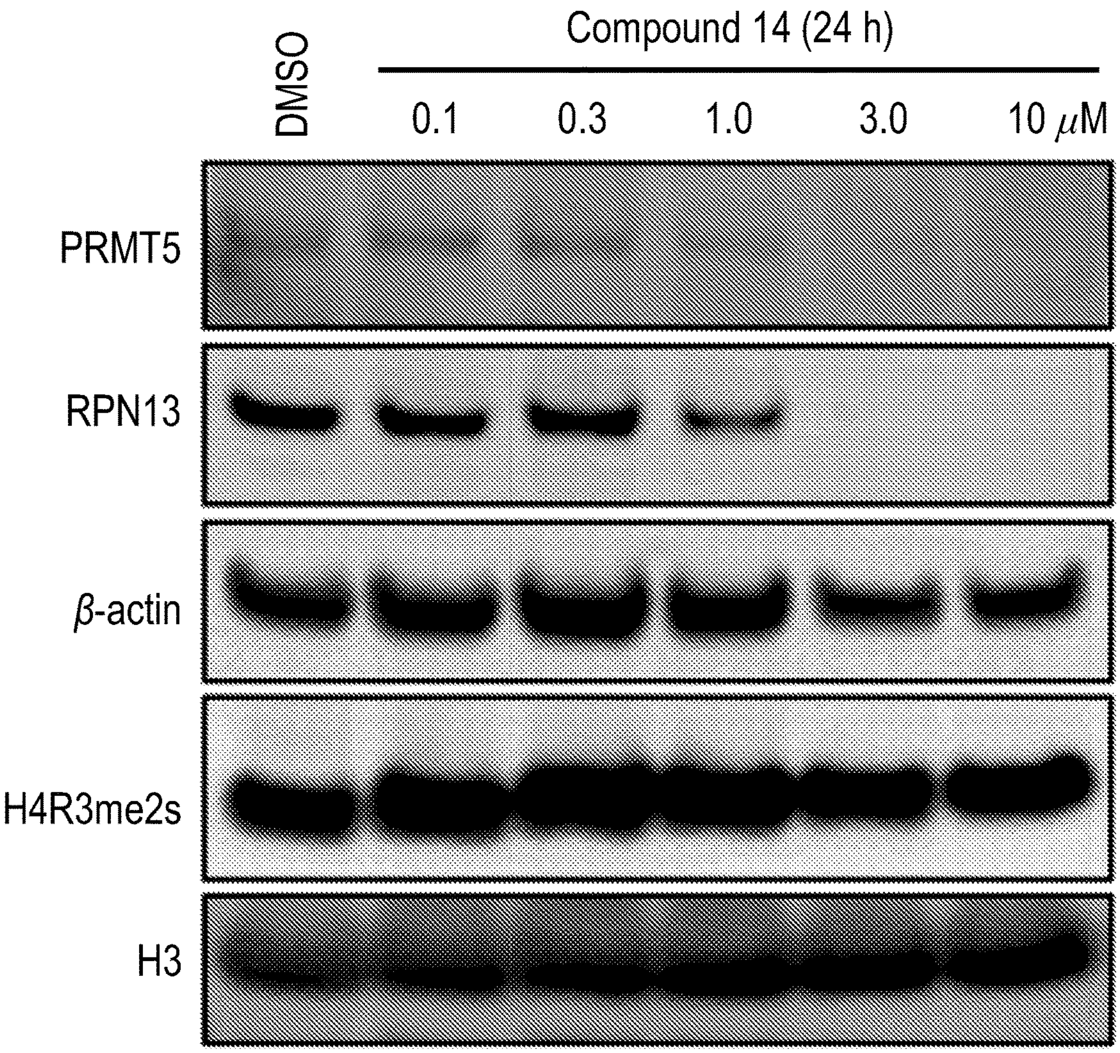
FIG. 4B is an image showing an immunoblot analysis of HL60 cells treated with different concentrations (μM) of inventive bifunctional compound 14 for 24 hours.

The results are illustrated in FIG. 4A-FIG. 4B. FIG. 4A shows minimum degradation of blotted targets, suggesting that these molecules were tolerated in the cell at up to 10 μM concentration. FIG. 4B shows that treatment of compound 14 resulted in degration of PRMT5 and RPN13 at a concentration of 1 μM, with complete loss of both proteins at 3 μM.

All patent publications and non-patent publications are indicative of the level of skill of those skilled in the art to which this invention pertains. All these publications (including any specific portions thereof that are referenced) are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A bifunctional compound having a structure represented by formula (I):

(I)

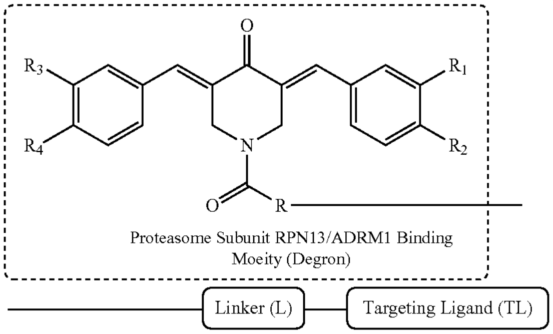

wherein

R represents

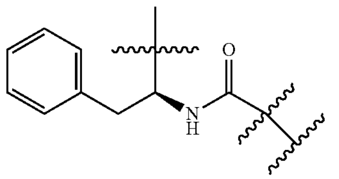

or

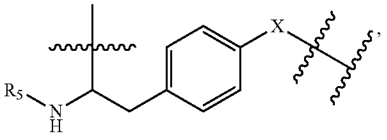

wherein the squiggle (  ) represents the attachment point to the carbonyl group (C(O)) and the double-squiggle (  ) represents the attachment point to

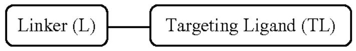

;

X represents $CH_2$, NH or O;

$R_1$ and $R_3$ each independently represents hydrogen, halo, methoxy, $NO_2$, CN, —C(O)OR'$_1$ or —C(O)NR'$_1$R'$_2$;

$R_2$ and $R_4$ each independently represents halo, methoxy, $NO_2$, CN, —C(O)OR'$_1$ or —C(O)NR'$_1$R'$_2$, wherein R'$_1$ and R'$_2$ are independently H or optionally substituted $C_1$-$C_6$ alkyl; $R_5$ represents H, biotinyl, or a solubility enhancing group;

the linker comprises an alkylene chain which may be interrupted by and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different, or comprises a polyethylene glycol chain which may terminate at either or both termini in at least one of —S—, —N(R')—, —C≡C—, —C(O)—, —C(O)O—, —OC(O)—, —OC(O)O—, —C(NOR')—, —C(O)N(R)—, —C(O)N(R)C(O)—, —C(O)N(R')C(O)N(R)—, —N(R')C(O)—, N(R')C(O)N(R')—, —N(R')C(O)O—, —OC(O)N(R'), —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different;

and the targeting ligand is represented by TL1 or TL2:

(TL1)

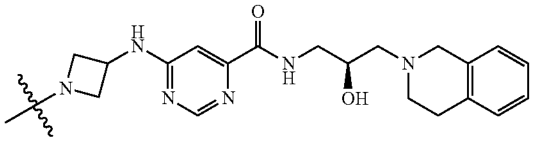

or

-continued (TL2)

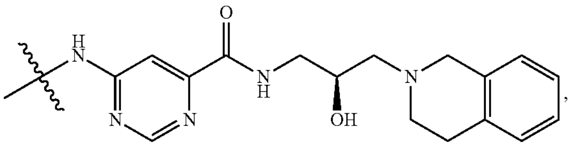

, or a pharmaceutically acceptable salt or stereoisomer thereof.

2. The bifunctional compound of claim 1, wherein the targeting ligand is represented by TL1:

(TL1)

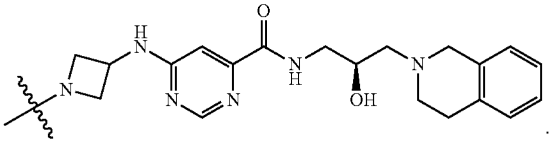

.

3. The bifunctional compound of claim 1, which is represented by any one of structures (I-1) to (I-4):

(I-1)

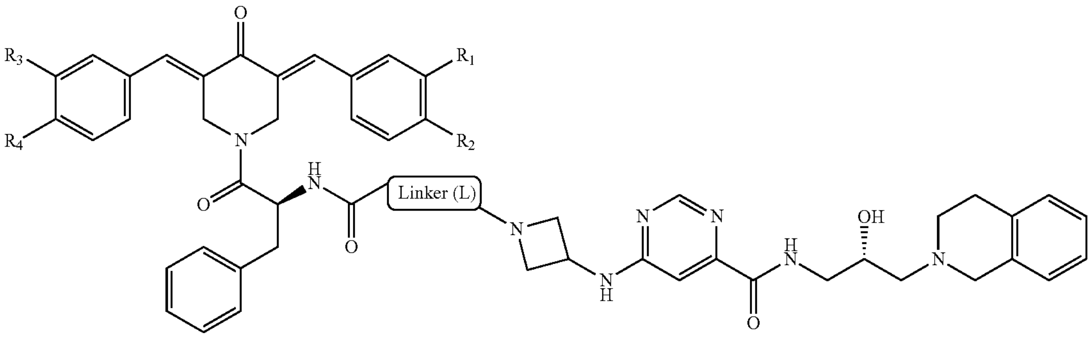

;

(I-2)

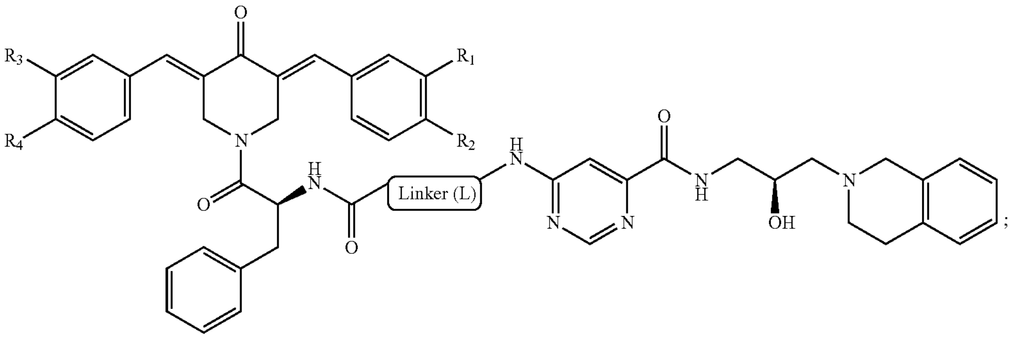

;

-continued (I-3)

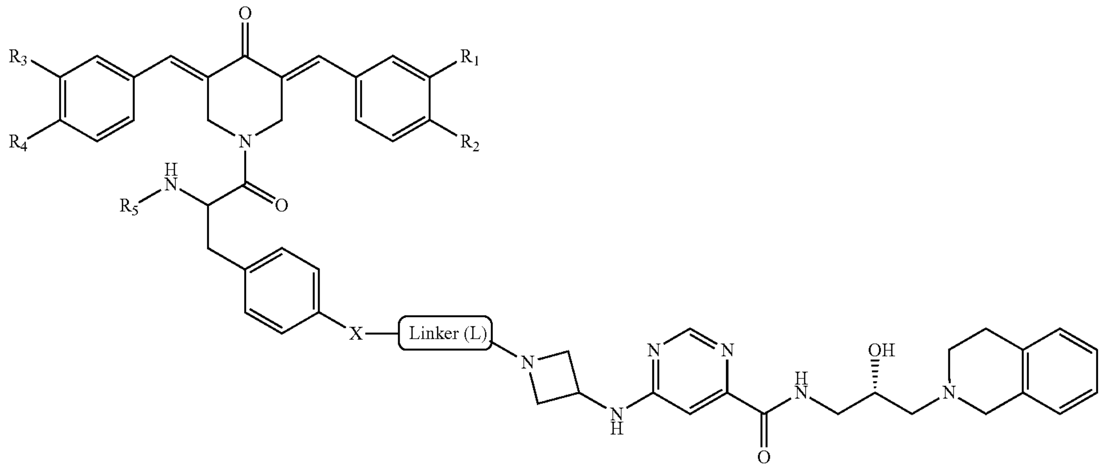

; and (I-4)

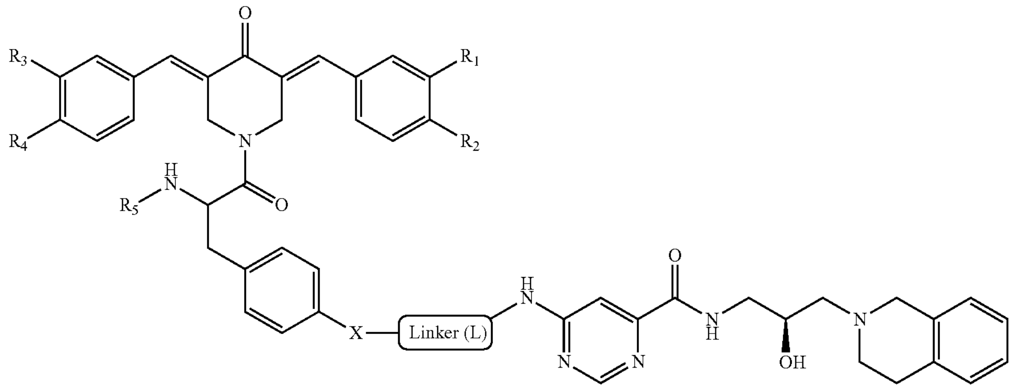

, or a pharmaceutically acceptable salt or stereoisomer thereof.

4. The bifunctional compound of claim 3, wherein each of $R_1$, $R_2$, $R_3$ and $R_4$ represents Cl.

5. The bifunctional compound of claim 3, wherein each of $R_1$ and $R_3$ represents CN, and each of $R_2$ and $R_4$ represents Cl.

6. The bifunctional compound of claim 3, wherein each of $R_1$ and $R_3$ represents Cl, and each of $R_2$ and $R_4$ represents methoxy.

7. The bifunctional compound of claim 3, wherein each of $R_1$ and $R_3$ represents H, and each of $R_2$ and $R_4$ represents $NO_2$.

8. The bifunctional compound of claim 3, which is represented by any one of structures (I-1a) to (I-5d):

(I-1a)

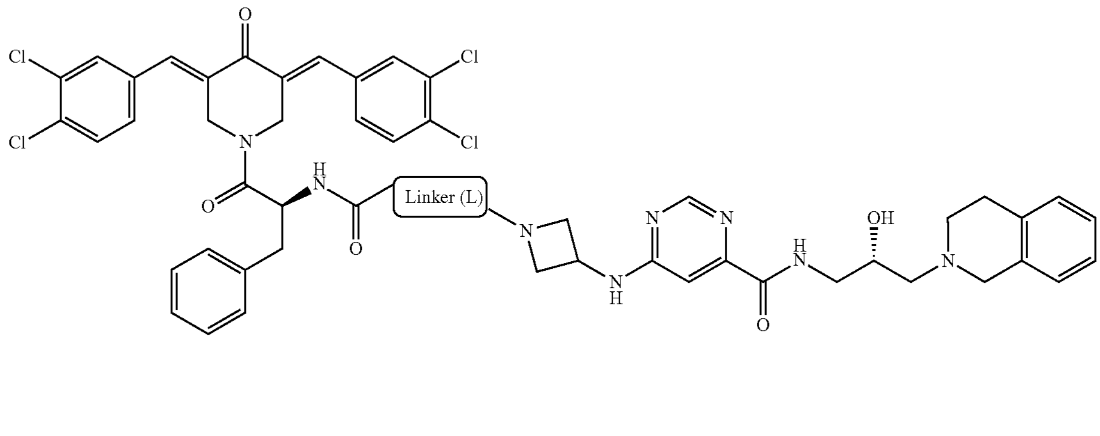

;

-continued
(I-1b)
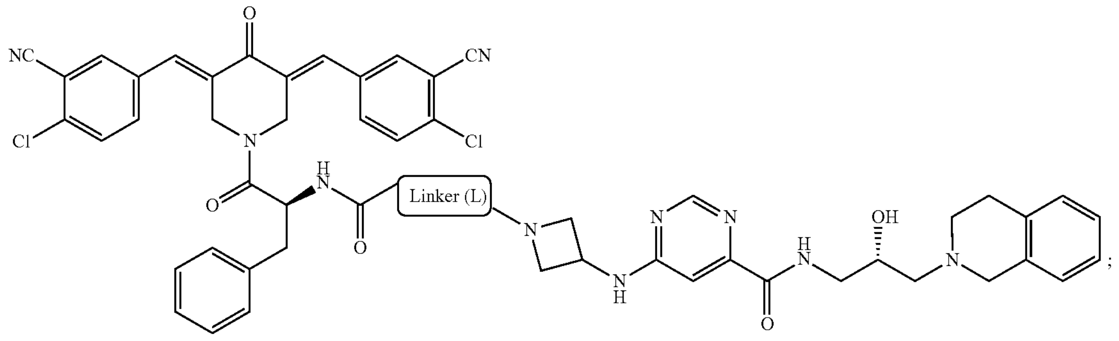
(I-1c)
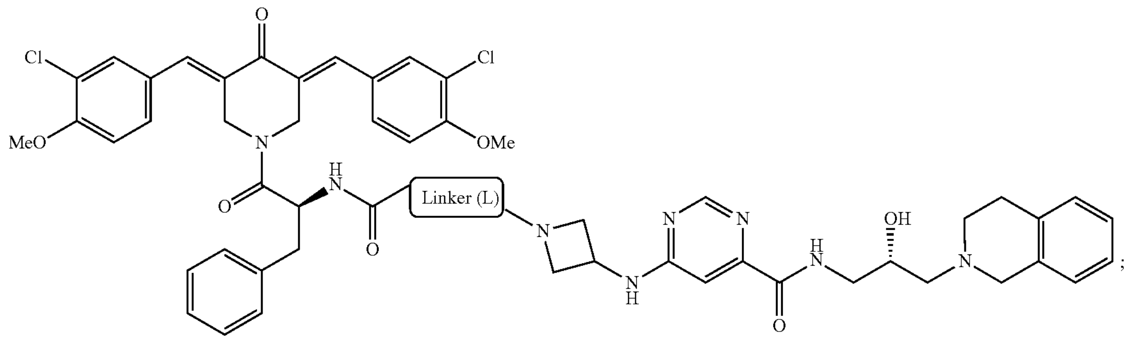
(I-2a)
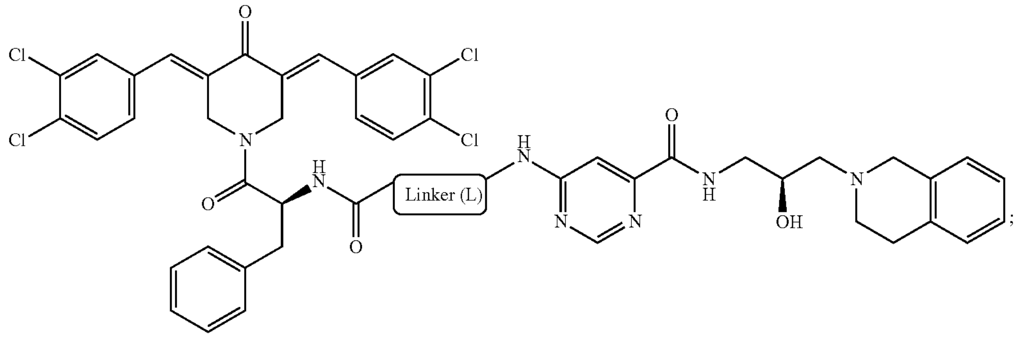
(I-2b)
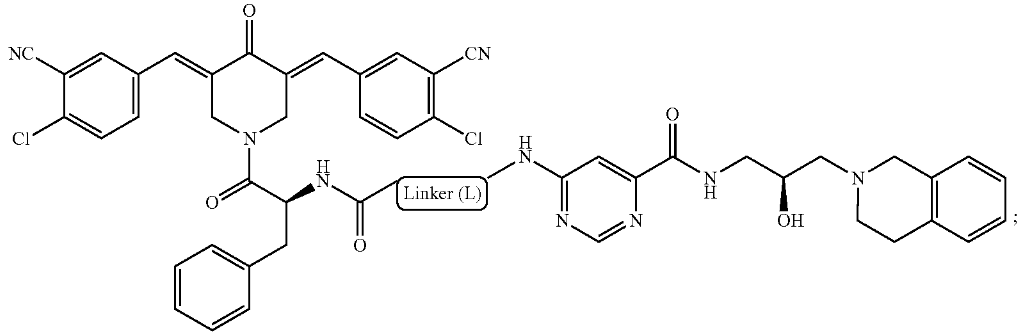

-continued
(I-2c)
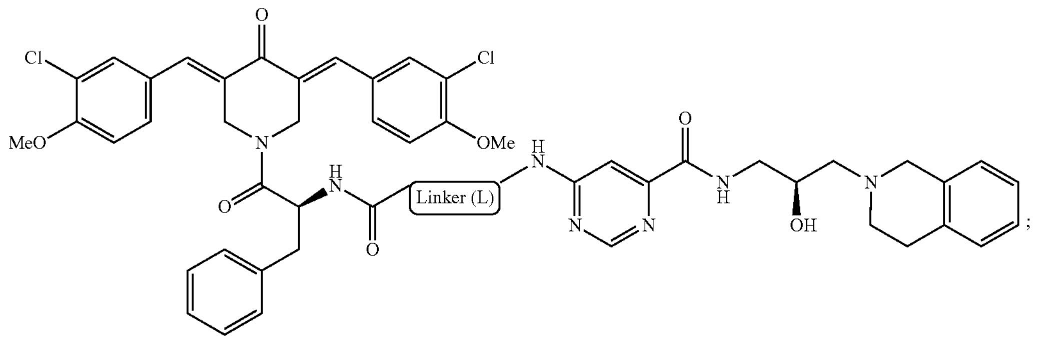
(I-3a)
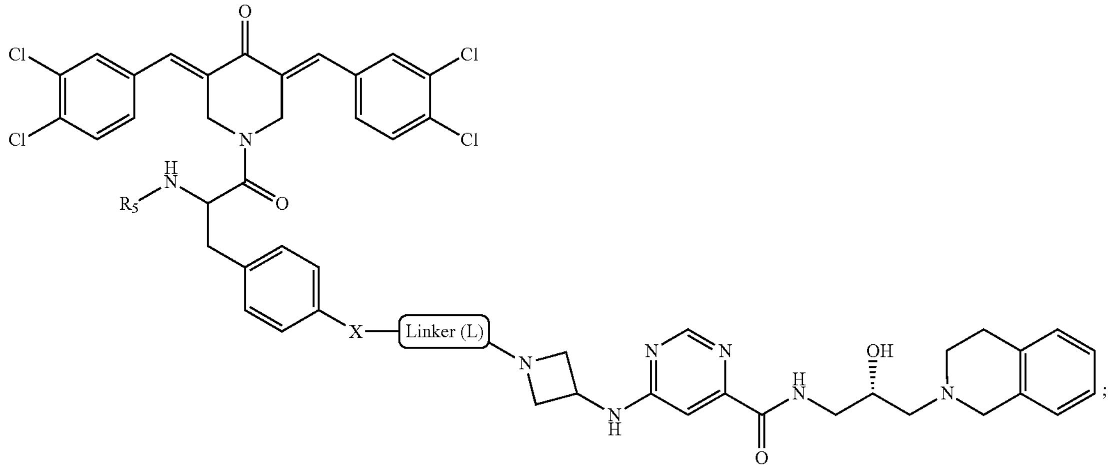
(I-3b)
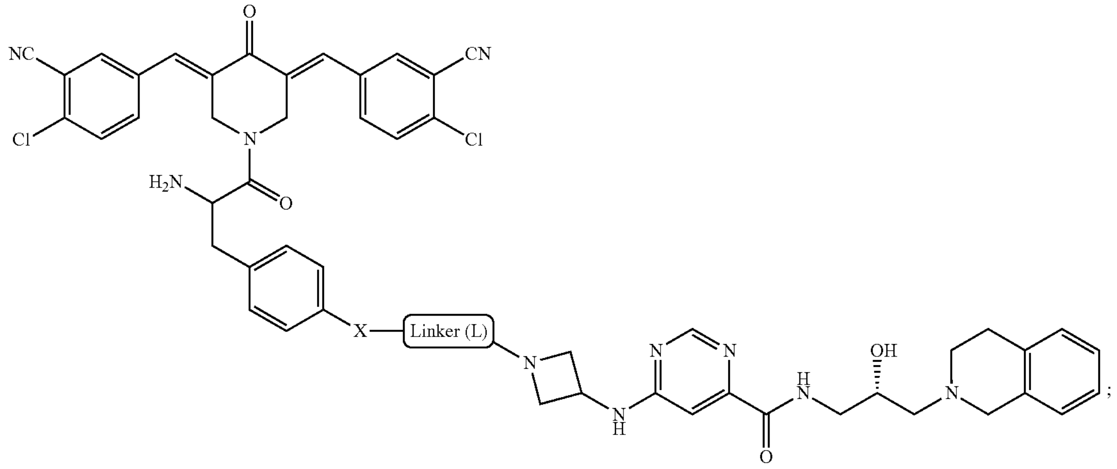

-continued
(I-3c)
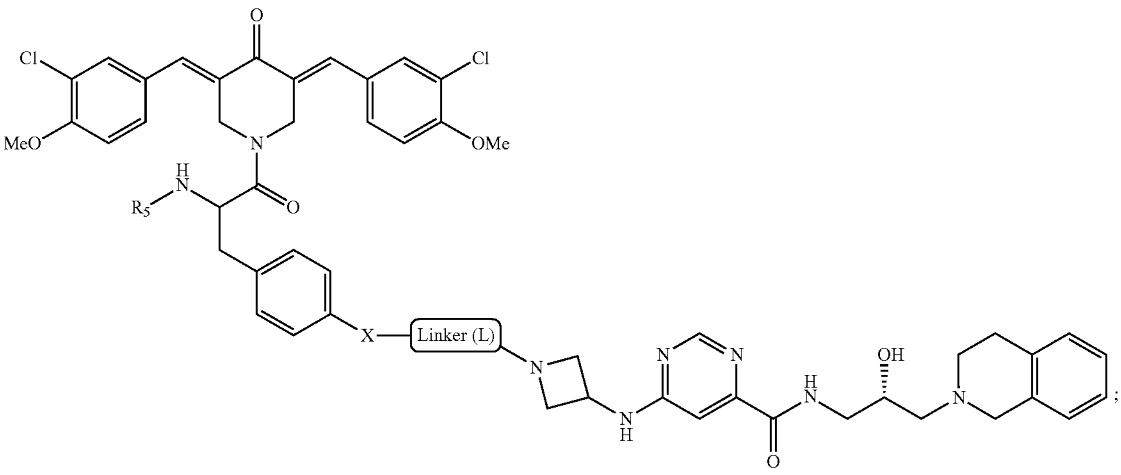
;
(I-4a)
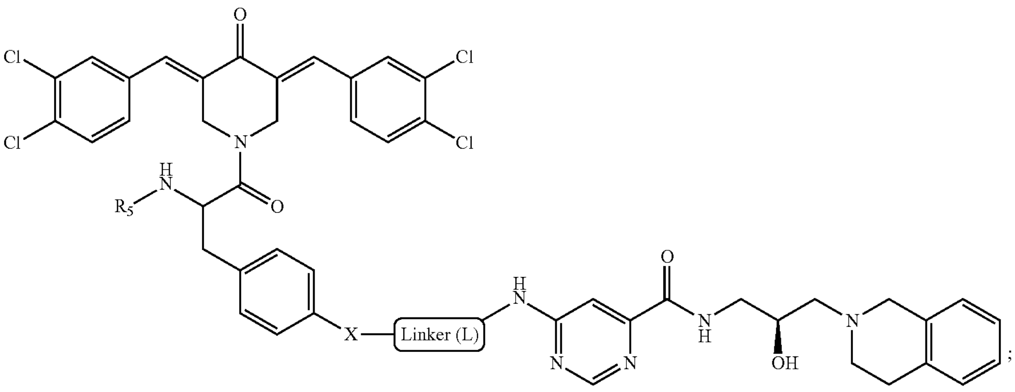
;
(I-4b)
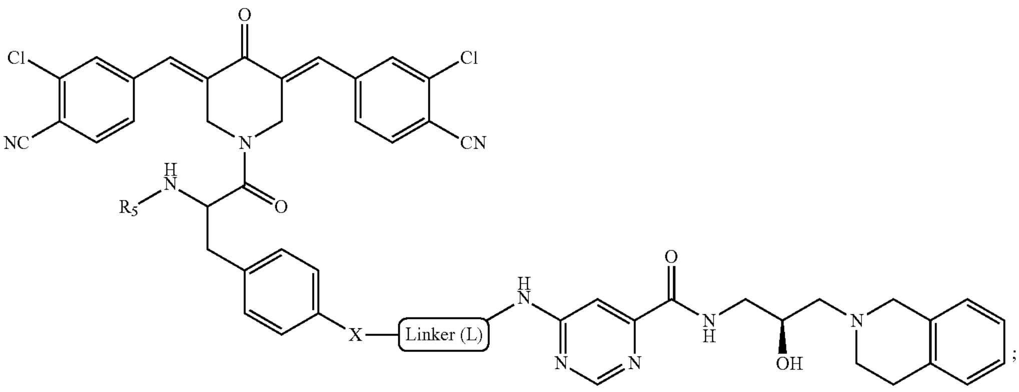
;

-continued
(I-4c)
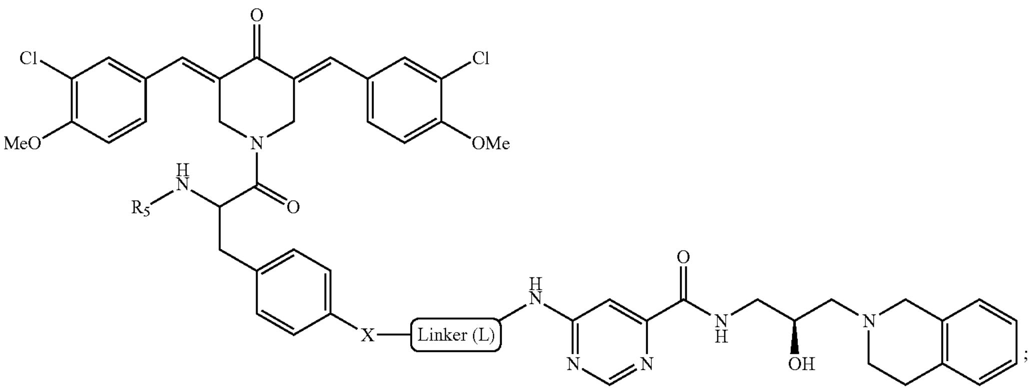
;
(I-5a)
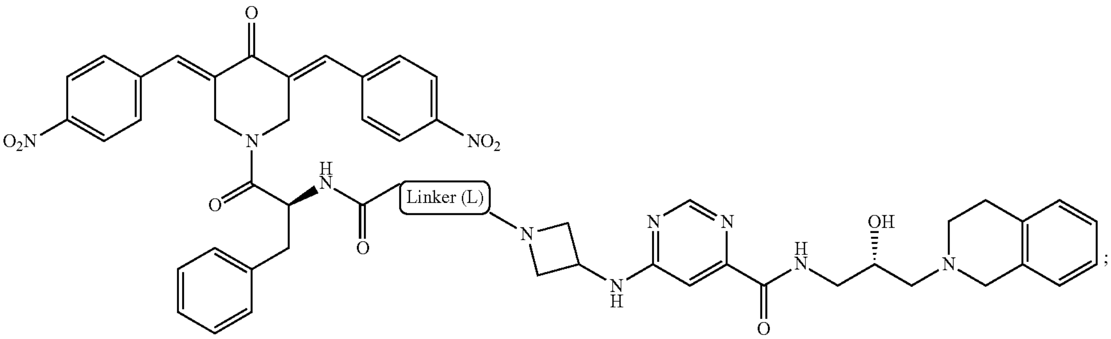
;
(I-5b)
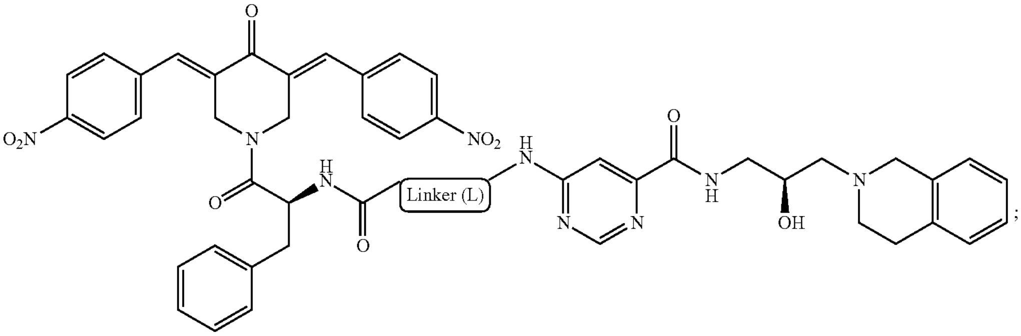
;
(I-5c)
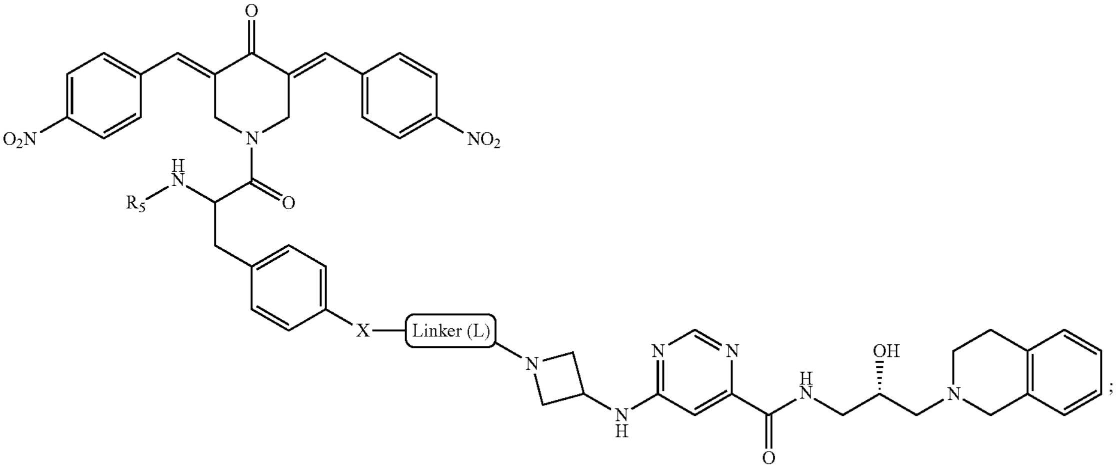
; and -continued (I-5d)

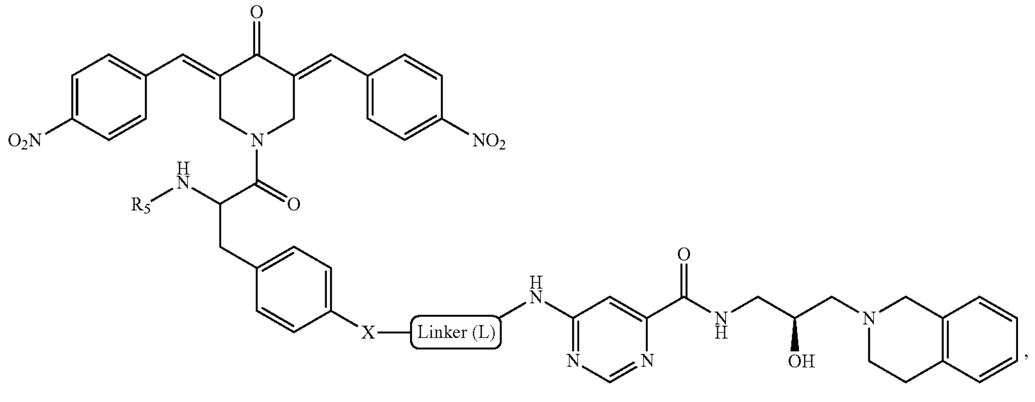

or a pharmaceutically acceptable salt or stereoisomer thereof.

9. The bifunctional compound of claim 8, wherein $R_5$ is H.

10. The bifunctional compound of claim 8, wherein $R_5$ is biotynyl or a solubility enhancing group.

11. The bifunctional compound of claim 10, wherein the solubility enhancing group is alpha-chloro acetyl.

12. The bifunctional compound of claim 1, wherein the linker comprises an alkylene chain which may be interrupted by and/or terminate at either or both termini in at least one of —O—, —S—, —N(R')—, —C≡C—, —C(O)—, —C(O)O—, —OC(O)—, —OC(O)O—, —C(NOR'), —C(O)N(R'), —C(O)N(R')C(O)—, —C(O)N(R')C(O)N(R')—, —N(R')C(O)—, —N(R')C(O)N(R'), —N(R')C(O)O—, —OC(O)N(R')—, —C(NR')—, —N(R')C(NR')—, —C(NR')N(R')—, —N(R')C(NR') N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

13. The bifunctional compound of claim 12, wherein the linker comprises an alkylene chain having 2-20 alkylene units.

14. The bifunctional compound of claim 1, wherein the linker comprises a polyethylene glycol chain which may terminate at either or both termini in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR)—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

15. The bifunctional compound of claim 14, wherein the linker comprises 1-6 polyethylene glycol units.

16. The bifunctional compound of claim 1, wherein the linker is represented by any one of structures:

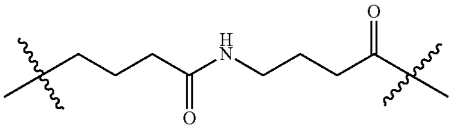
;
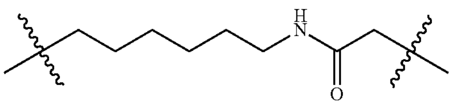
;

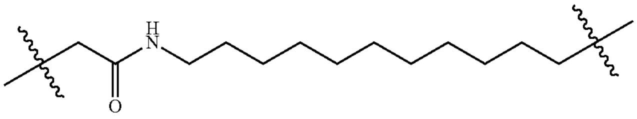
;
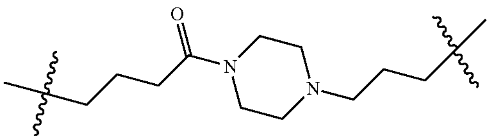
;

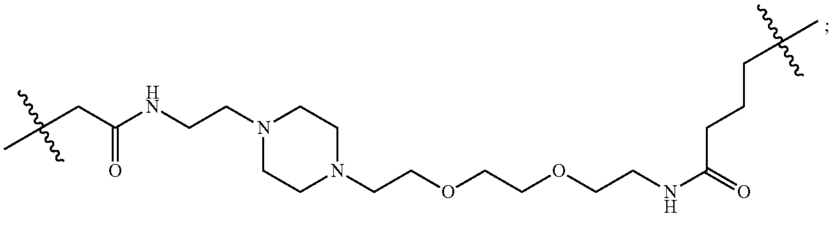
;

-continued
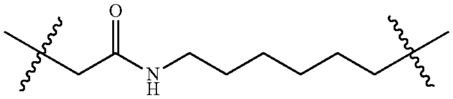
;
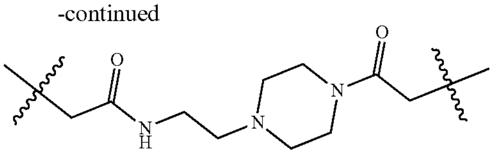
;
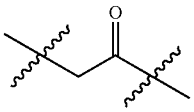
;
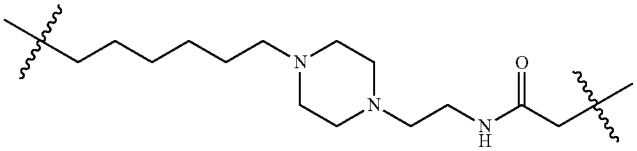
; and
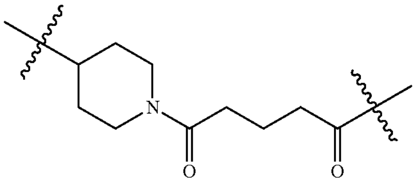
.
17. The bifunctional compound of claim 1, which is represented by any one of structures 1-14:
(1)
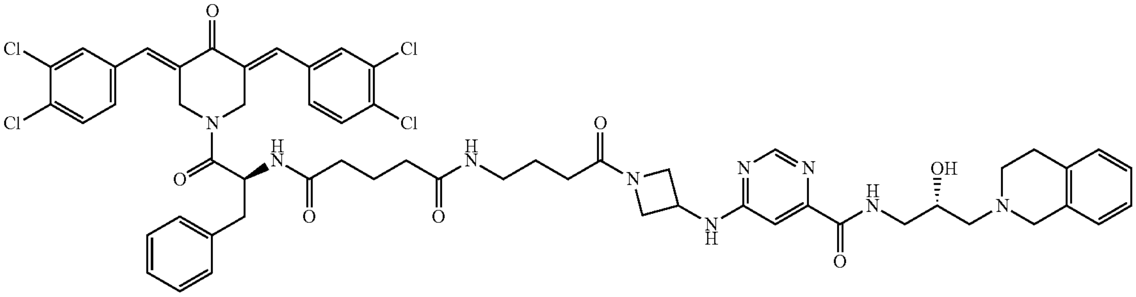
;
(2)
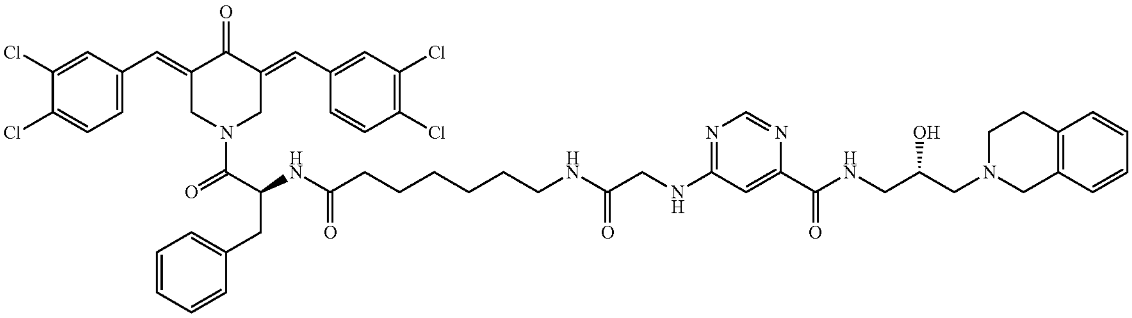
;

-continued
(3)
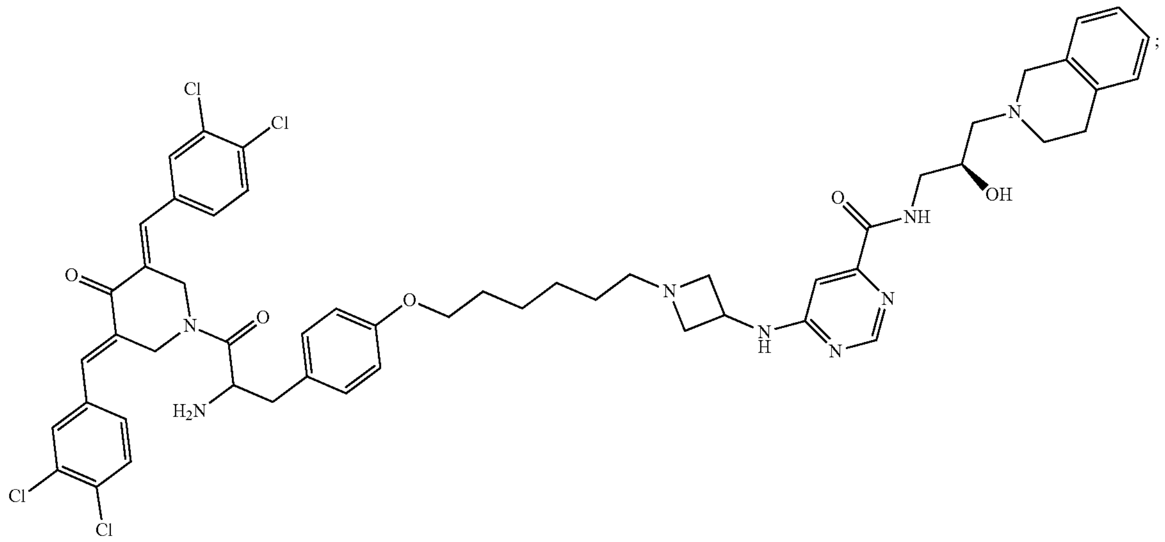
(4)
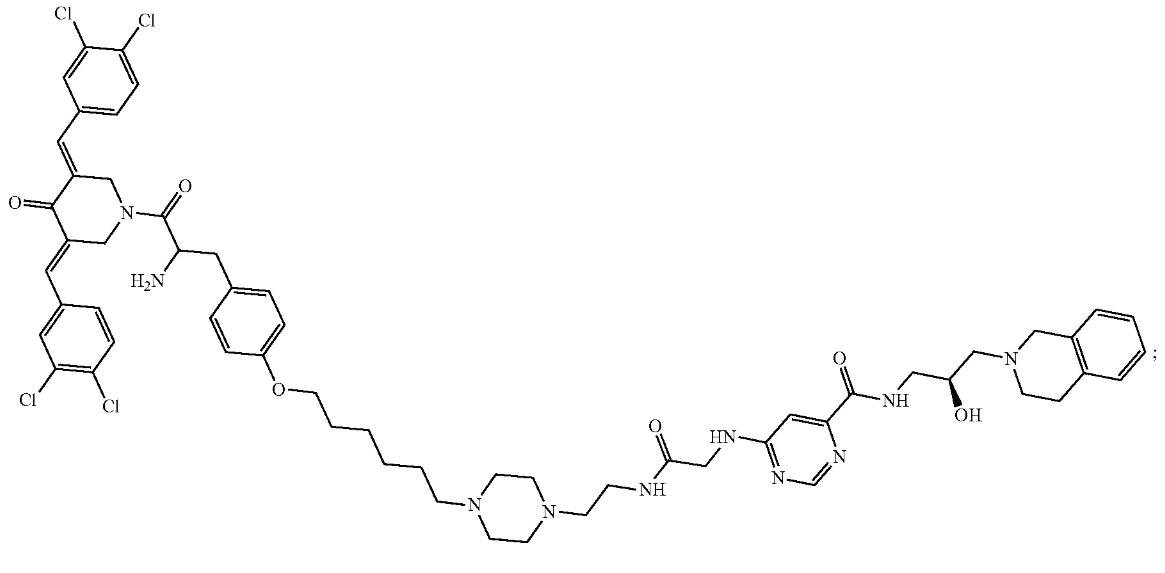
(5)
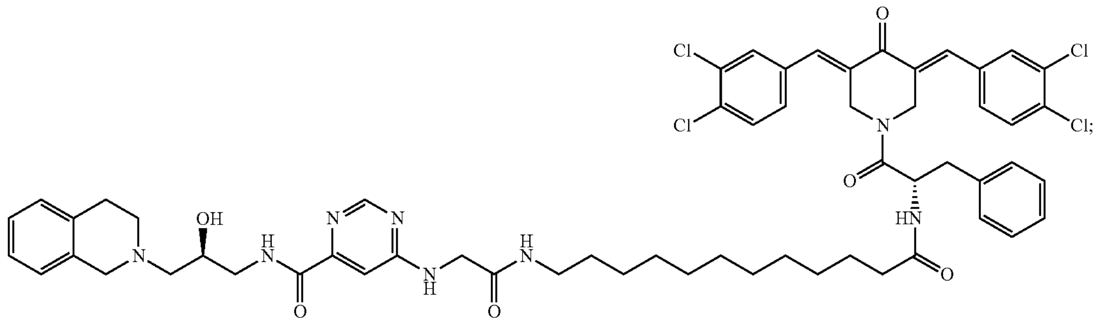

-continued
(6)
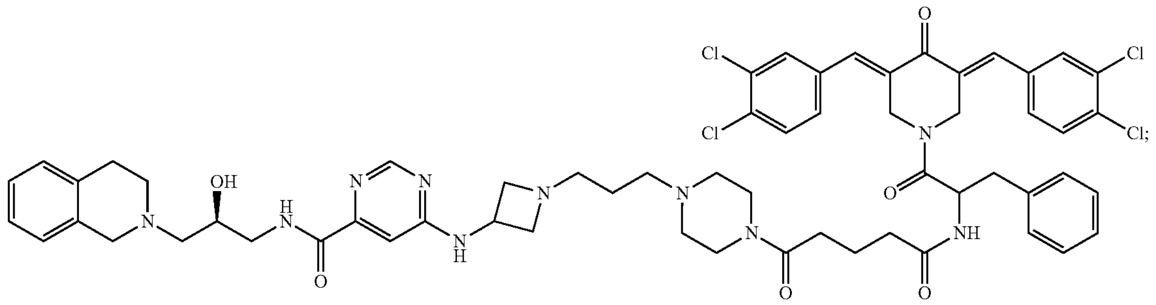
(7)
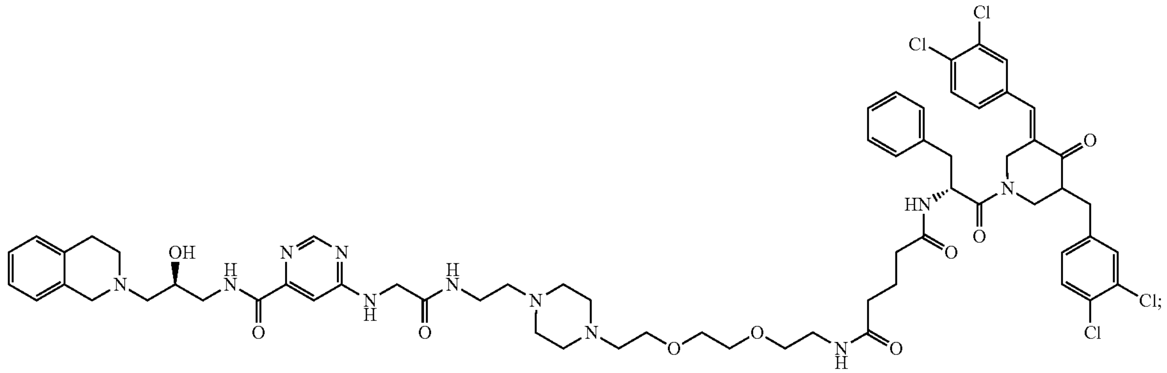
(8)
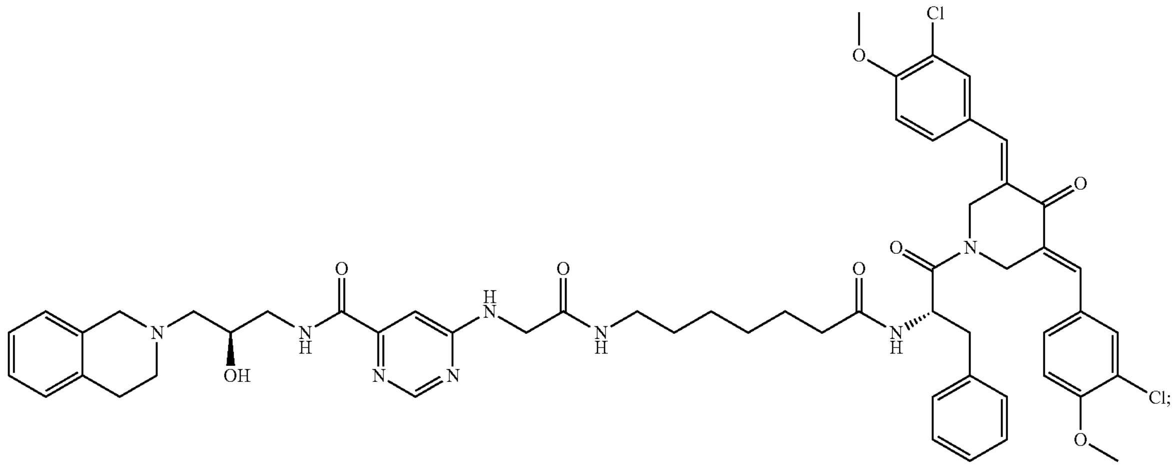
(9)
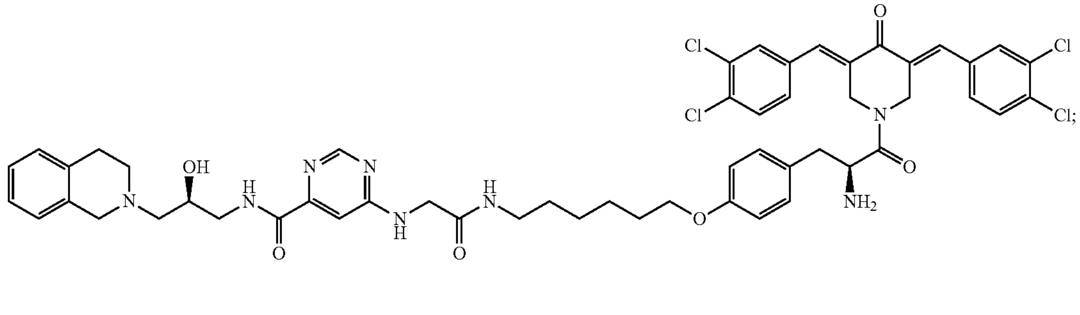

-continued
(10)
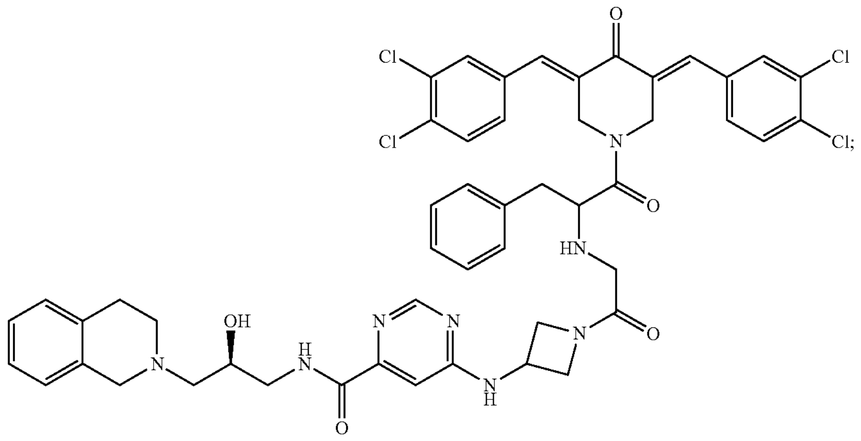
(11)
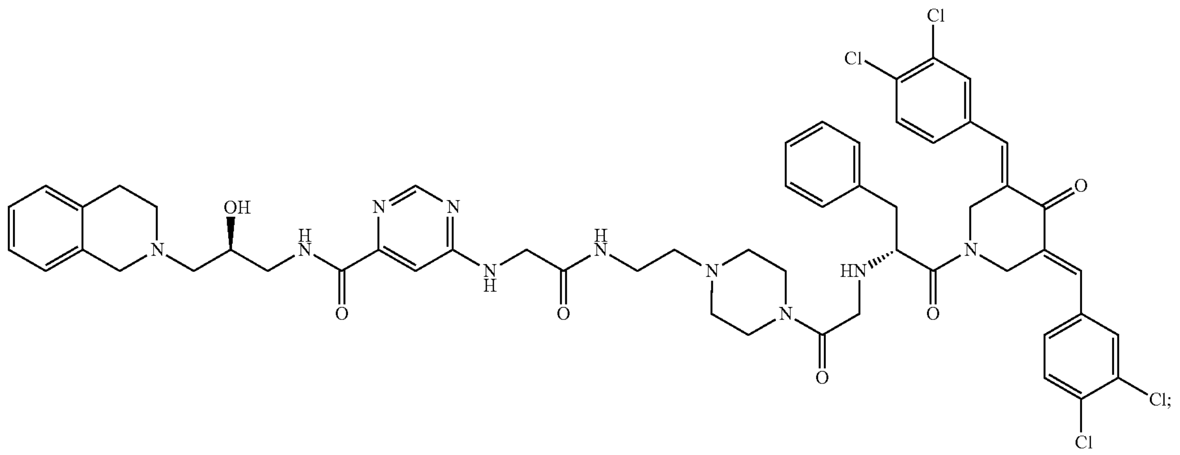
(12)
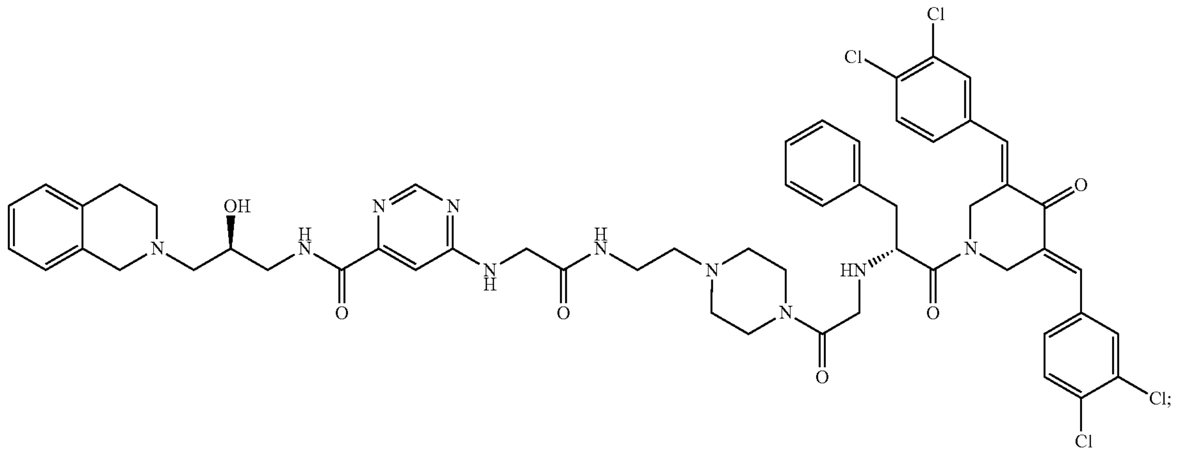

-continued (13)

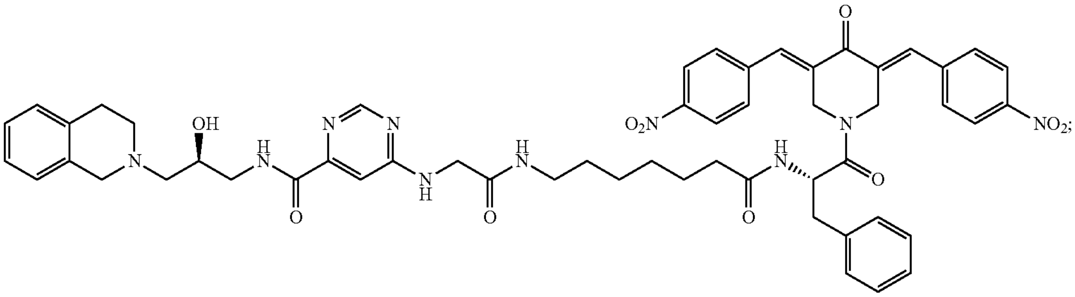

NO2; and (14)

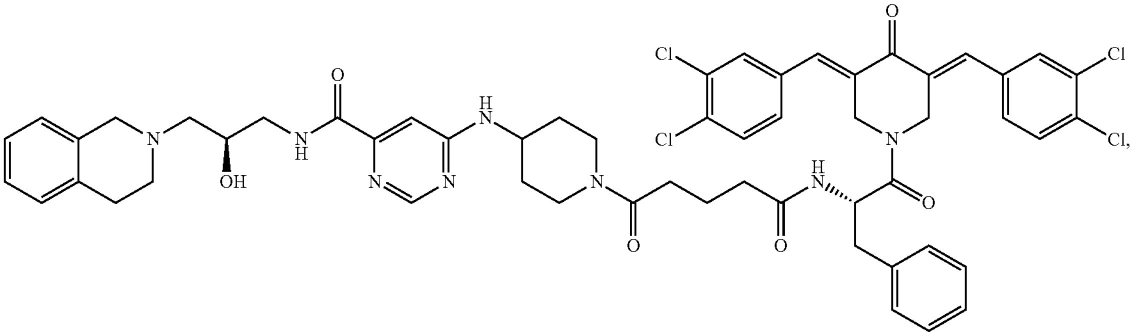

or a pharmaceutically acceptable salt or stereoisomer thereof.

18. A pharmaceutical composition, comprising a therapeutically effective amount of the compound or pharmaceutically acceptable salt or stereoisomer of claim 1, and a pharmaceutically acceptable carrier.

19. A method of treating a disease or disorder that is characterized or mediated by aberrant activity of PRMT5, comprising administering to a subject in need thereof a therapeutically effective amount of the compound or pharmaceutically acceptable salt or stereoisomer of claim 1.

20. The method of claim 19, wherein the disease or disorder is a cancer.

21. The method of claim 20, wherein the cancer is breast cancer, colorectal cancer, lung cancer, gastric cancer, nasopharyngeal cancer, ovarian cancer, germ cell tumors, B-cell lymphoma, T-cell lymphoma, metastatic melanoma, neuroblastoma or glioblastoma.

22. The method of claim 21, wherein the breast cancer is triple-negative breast cancer.

23. The method of claim 20, wherein the cancer is myelodysplastic syndrome (MDS) or acute myeloid leukemia (AML).

24. The bifunctional compound of claim 1, wherein the targeting ligand is represented by TL2:

(TL2)

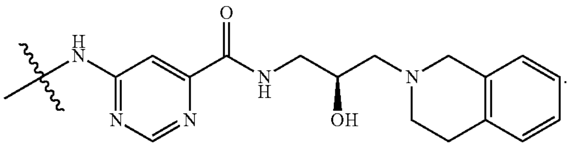

* * * * *